(12) United States Patent
Sava Gallis et al.

(10) Patent No.: US 11,007,516 B1
(45) Date of Patent: May 18, 2021

(54) TUNABLE METAL-ORGANIC FRAMEWORK COMPOSITIONS AND METHODS THEREOF

(71) Applicant: National Technology & Engineering Solutions of Sandia, LLC, Albuquerque, NM (US)

(72) Inventors: Dorina F. Sava Gallis, Albuquerque, NM (US); Darryl Y. Sasaki, Livermore, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 15/994,904

(22) Filed: May 31, 2018

Related U.S. Application Data

(60) Provisional application No. 62/522,006, filed on Jun. 19, 2017.

(51) Int. Cl.
| | | |
|---|---|---|
| *B01J 21/16* | (2006.01) | |
| *B01J 31/16* | (2006.01) | |
| *A61K 49/00* | (2006.01) | |

(52) U.S. Cl.
CPC ....... *B01J 31/1691* (2013.01); *A61K 49/0065* (2013.01); *A61K 49/0089* (2013.01); *A61K 2123/00* (2013.01); *B01J 2531/0211* (2013.01); *B01J 2531/0269* (2013.01); *B01J 2531/38* (2013.01)

(58) Field of Classification Search
None
See application file for complete search history.

(56) References Cited

U.S. PATENT DOCUMENTS

| | | |
|---|---|---|
| 5,616,790 A | 4/1997 | Arnold et al. |
| 5,837,202 A | 11/1998 | Arnold et al. |
| 6,022,748 A | 2/2000 | Charych et al. |
| 6,048,546 A | 4/2000 | Sasaki et al. |
| 6,057,377 A | 5/2000 | Sasaki et al. |
| 6,485,987 B1 | 11/2002 | Charych et al. |
| 6,962,747 B1 | 11/2005 | Sasaki et al. |
| 8,734,816 B2 | 5/2014 | Liu et al. |
| 8,992,984 B1 | 3/2015 | Brinker et al. |
| 9,117,560 B1 | 8/2015 | Garino et al. |
| 9,162,914 B1 | 10/2015 | Nenoff et al. |
| 9,266,907 B2 | 2/2016 | Xue et al. |
| 9,343,192 B2 | 5/2016 | Garino et al. |
| 9,480,653 B2 | 11/2016 | Brinker et al. |

(Continued)

FOREIGN PATENT DOCUMENTS

| | | |
|---|---|---|
| WO | WO 2013/115878 A2 | 8/2013 |
| WO | WO 2017/023407 A2 | 2/2017 |

(Continued)

OTHER PUBLICATIONS

Xue et al. J. Am. Chem. Soc. 2017, 137, 5034-5040.*

(Continued)

*Primary Examiner* — Clinton A Brooks
(74) *Attorney, Agent, or Firm* — Helen S. Baca

(57) ABSTRACT

The present invention relates to a metal-organic framework composition, as well as constructs and methods thereof. In one particular example, the composition provides a platform having an emission signal in the deep red to near-infrared (NIR) region.

20 Claims, 19 Drawing Sheets

(56) References Cited

U.S. PATENT DOCUMENTS

| | | | |
|---|---|---|---|
| 9,552,897 B2 | 1/2017 | Nenoff et al. | |
| 9,579,283 B2 | 2/2017 | Brinker et al. | |
| 9,741,945 B1 | 8/2017 | Nenoff et al. | |
| 9,855,217 B2 | 1/2018 | Brinker et al. | |
| 2008/0160313 A1 | 7/2008 | Lopez et al. | |
| 2011/0268791 A1 | 11/2011 | Liu et al. | |
| 2013/0121911 A1 | 5/2013 | Nenoff et al. | |
| 2014/0079774 A1 | 3/2014 | Brinker et al. | |
| 2014/0301951 A1 | 10/2014 | Liu et al. | |
| 2015/0010475 A1 | 1/2015 | Brinker et al. | |
| 2015/0164798 A1 | 6/2015 | Brinker et al. | |
| 2015/0272885 A1 | 10/2015 | Ashley et al. | |
| 2015/0320681 A1 | 11/2015 | Brinker et al. | |
| 2015/0332798 A1 | 11/2015 | Garino et al. | |
| 2016/0012927 A1 | 1/2016 | Nenoff et al. | |
| 2016/0090603 A1 | 3/2016 | Carnes et al. | |
| 2016/0102108 A1* | 4/2016 | Eddaoudi | C07C 51/418 556/1 |
| 2016/0106671 A1 | 4/2016 | Brinker et al. | |
| 2016/0151482 A1 | 6/2016 | Carnes et al. | |
| 2016/0287717 A1 | 10/2016 | Brinker et al. | |
| 2016/0338954 A1 | 11/2016 | Brinker et al. | |
| 2017/0165375 A1 | 6/2017 | Ashley et al. | |
| 2017/0232115 A1 | 8/2017 | Ashley et al. | |
| 2018/0028686 A1 | 2/2018 | Brinker et al. | |
| 2018/0049984 A1 | 2/2018 | Brinker et al. | |
| 2018/0053968 A1 | 2/2018 | Sava Gallis et al. | |
| 2018/0105430 A1 | 4/2018 | Carnes et al. | |
| 2018/0110831 A1 | 4/2018 | Brinker et al. | |

FOREIGN PATENT DOCUMENTS

| | | |
|---|---|---|
| WO | WO 2017/041032 A1 | 3/2017 |
| WO | WO 2017/041033 A1 | 3/2017 |
| WO | WO 2017/120504 A1 | 7/2017 |

OTHER PUBLICATIONS

U.S. Appl. No. 15/269,745, filed Sep. 19, 2016, Nenoff et al.

Aaron JS et al., "Advanced optical imaging reveals the dependence of particle geometry on interactions between CdSe quantum dots and immune cells," *Small* 2011;7:334-41.

Alezi D et al., "Quest for highly connected metal-organic framework platforms: rare-earth polynuclear clusters versatility meets net topology needs," *J. Am. Chem. Soc.* 2015;137:5421-30.

Allendorf MD et al., "Luminescent metal-organic frameworks," *Chem. Soc. Rev.* 2009;38:1330-52.

Antaris AL et al., "A small-molecule dye for NIR-II imaging," *Nat. Mater.* 2016;15:235-42.

Bruns OT et al., "Next-generation in vivo optical imaging with short-wave infrared quantum dots," *Nat. Biomed. Eng.* 2017;1:0056 (29 pp.).

Bruns OT et al., Supplementary Information for "Next-generation in vivo optical imaging with short-wave infrared quantum dots," *Nat. Biomed. Eng.* 2017;1:0056 (20 pp.).

Bünzli JC et al., "Taking advantage of luminescent lanthanide ions," *Chem. Soc. Rev.* 2005;34:1048-77.

Chapman KW, "Emerging operando and x-ray pair distribution function methods for energy materials development," *MRS Bull.* 2016;41:231-40.

Chen B et al., "Metal-organic frameworks with functional pores for recognition of small molecules," *Acc. Chem. Res.* 2010;43:1115-24.

Chen Z et al., "Near-infrared (NIR) luminescence from lanthanide(III) complexes," Chapter 12 in *Rare Earth Coordination Chemistry: Fundamentals and Applications* (C Huang, ed.), John Wiley & Sons Ltd. (Chichester, UK, 2010), pp. 473-527.

Chupas PJ et al., "Applications of an amorphous silicon-based area detector for high-resolution, high-sensitivity and fast time-resolved pair distribution function measurements," *J. Appl. Crystallogr.* 2007;40:463-70.

Chupas PJ et al., "Rapid-acquisition pair distribution function (RA-PDF) analysis," *J. Appl. Crystallogr.* 2003;36:1342-7.

Cravillon J et al., "Rapid room-temperature synthesis and characterization of nanocrystals of a prototypical zeolitic imidazolate framework," *Chem. Mater.* 2009;21:1410-2.

Cui Y et al., "Lanthanide metal-organic frameworks for luminescent sensing and light-emitting applications," *Coord. Chem. Rev.* 2014;273-274:76-86.

Cui Y et al., "Luminescent functional metal-organic frameworks," *Chem. Rev.* 2012;112:1126-62.

Eddaoudi M et al., "Zeolite-like metal-organic frameworks (ZMOFs): design, synthesis, and properties," *Chem. Soc. Rev.* 2015;44:228-49.

Escobedo JO et al., "NIR dyes for bioimaging applications," *Curr. Opin. Chem. Biol.* 2010;14:64-70.

Fissan H et al., "Comparison of different characterization methods for nanoparticle dispersions before and after aerosolization," *Anal. Methods* 2014;6:7324-34.

Foucault-Collet A et al., "Lanthanide near infrared imaging in living cells with Yb3+ nano metal organic frameworks," *Proc. Nat'l Acad. Sci. USA* 2013;110:17199-204.

Furukawa H et al., "The chemistry and applications of metal-organic frameworks," *Science* 2013;341:1230444 (12 pp.).

Giménez-Marqués M et al., "Nanostructured metal-organic frameworks and their bio-related applications," *Coord. Chem. Rev.* 2016;307, Part 2:342-60.

Guillerm V et al., "Discovery and introduction of a (3,18)-connected net as an ideal blueprint for the design of metal-organic frameworks," *Nat. Chem.* 2014;6:673-80.

Guo Z et al., "A robust near infrared luminescent ytterbium metal-organic framework for sensing of small molecules," *Chem. Commun.* 2011;47:5551-3.

Haaland DM et al., "Chapter 12—Experimental and Data Analytical Approaches to Automating Multivariate Curve Resolution in the Analysis of Hyperspectral Images," in *Data Handling in Science and Technology* (C Ruckebusch, ed.), Elsevier (Amsterdam, The Netherlands, 2016), vol. 30, pp. 381-408.

He C et al., "Nanomedicine applications of hybrid nanomaterials built from metal-ligand coordination bonds: nanoscale metal-organic frameworks and nanoscale coordination polymers," *Chem. Rev.* 2015;115:11079-108.

Hemmer E et al., "Exploiting the biological windows: current perspectives on fluorescent bioprobes emitting above 1000 nm," *Nanoscale Horizons* 2016;1:168-84.

Hirschle P et al., "Exploration of MOF nanoparticle sizes using various physical characterization methods—is what you measure what you get?," *Cryst Eng. Comm.* 2016;18:4359-68.

Hu Q et al., "A low cytotoxic cationic metal-organic framework carrier for controllable drug release," *J. Med. Chem.* 2014;57:5679-85.

Jones HDT et al., "Preprocessing strategies to improve MCR analyses of hyperspectral images," *Chemometrics Intell. Lab. Syst.* 2012;117:149-58.

Kim D et al., "Recent advances in inorganic nanoparticle-based NIR luminescence imaging: semiconductor nanoparticles and lanthanide nanoparticles," *Bioconjugate Chem.* 2017;28:115-23.

Lambris JD et al., "Complement evasion by human pathogens," *Nat. Rev. Microbiol.* 2008;6:132-42.

Luebke R et al., "Versatile rare earth hexanuclear clusters for the design and synthesis of highly-connected ftw-MOFs," *Chem. Sci.* 2015;6:4095-102.

Moore EG et al., "From antenna to assay: lessons learned in lanthanide luminescence," *Acc. Chem. Res.* 2009;42:542-52.

Nesmerak K, "Lanthanide/actinide toxicity," in *Encyclopedia of Metalloproteins* (RH Kretsinger, VN Uversky, EA Permyakov, eds.), Springer (New York, NY, 2013), pp. 1098-1103.

Orellana-Tavra C et al., "Drug delivery and controlled release from biocompatible metal-organic frameworks using mechanical amorphization," *J. Mater. Chem. B* 2016;4:7697-707.

Pansare VJ et al., "Review of long-wavelength optical and NIR imaging materials: contrast agents, fluorophores, and multifunctional nano carriers," *Chem. Mater.* 2012;24:812-27.

(56) References Cited

OTHER PUBLICATIONS

Park KS et al., "Exceptional chemical and thermal stability of zeolitic imidazolate frameworks," *Proc. Nat'l Acad. Sci. USA* 2006;103:10186-91.

Pichaandi J et al., "Near-infrared emitting quantum dots: recent progress on their synthesis and characterization," *Coord. Chem. Rev.* 2014;263-264:138-50.

Poon IK et al., "Molecular mechanisms of late apoptotic/necrotic cell clearance," *Cell Death Differ.* 2010;17:381-97.

Ruiz-Medina A et al., "Lanthanide-sensitized luminescence as a promising tool in clinical analysis," *Appl. Spectrosc. Rev.* 2011;46:561-80.

Sava DF et al., "Intrinsic broad-band white-light emission by a tuned, corrugated metal-organic framework," *J. Am. Chem. Soc.* 2012;134:3983-6.

Sava Gallis DF et al., "Efficient photoluminescence via metal-ligand alteration in a new MOFs family," *Chem. Mater.* 2014;26:2943-51.

Sava Gallis DF et al., "Multifunctional, tunable metal-organic framework materials platform for bioimaging applications," *ACS Appl. Mater. Interfaces* 2017;9:22268-77.

Sava Gallis DF et al., Supporting Information for "Multifunctional, tunable metal-organic framework materials platform for bioimaging applications," *ACS Appl. Mater. Interfaces* 2017;9:22268-77 (16 pp.).

Semisch A et al., "Copper ions interfere with the reduction of the water-soluble tetrazolium salt-8," *Chem. Res. Toxicol.* 2014;27:169-71.

Shen D et al., "Biphase stratification approach to three-dimensional dendritic biodegradable mesoporous silica nanospheres," *Nano Lett.* 2014;14:923-32.

Sinclair MB et al., "Hyperspectral confocal microscope," *Appl. Opt.* 2006;45:6283-91.

Smith AM et al., "Bioimaging: second window for in vivo imaging," *Nat. Nanotechnol.* 2009;4:710-1.

Sohaebuddin SK et al., "Nanomaterial cytotoxicity is composition, size, and cell type dependent," *Part. Fibre Toxicol.* 2010;7:22 (17 pp.).

Tamames-Tabar C et al., "Cytotoxicity of nanoscaled metal-organic frameworksm," *J. Mater. Chem. B* 2014;2:262-71.

Welsher K et al., "A route to brightly fluorescent carbon nanotubes for near-infrared imaging in mice," *Nat. Nanotechnol.* 2009;4:773-80.

White KA et al., "Near-infrared emitting ytterbium metal-organic frameworks with tunable excitation properties," *Chem. Commun.* 2009;30:4506-8.

White KA et al., "Near-infrared luminescent lanthanide MOF barcodes," *J. Am. Chem. Soc.* 2009;131:18069-71.

Xu LJ et al., "Recent advances in lanthanide luminescence with metal-organic chromophores as sensitizers," *Coord. Chem. Rev.* 2014;273-274:47-62.

Xue DX et al., "Tunable rare-earth fcu-MOFs: a platform for systematic enhancement of $CO_2$ adsorption energetics and uptake," *J. Am. Chem. Soc.* 2013;135:7660-7.

Yang J et al., "Structures, photoluminescence, up-conversion, and magnetism of 2d and 3d rare-earth coordination polymers with multicarboxylate linkages," *Inorg. Chem.* 2006;45:2857-65.

Zhang XD et al., "Traumatic brain injury imaging in the second near-infrared window with a molecular fluorophore," *Adv. Mater.* 2016;28:6872-9.

Zhao D et al., "A highly sensitive near-infrared luminescent metal-organic framework thermometer in the physiological range." *Chem. Commun.* 2016;52:8259-62.

\* cited by examiner

US 11,007,516 B1

TUNABLE METAL-ORGANIC FRAMEWORK COMPOSITIONS AND METHODS THEREOF

CROSS-REFERENCE TO RELATED APPLICATION

This application claims the benefit of U.S. Provisional Application No. 62/522,006, filed Jun. 19, 2017, which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to a metal-organic framework composition, as well as constructs and methods thereof. In one particular example, the composition provides a platform having an emission signal in the deep red to near-infrared (NIR) region.

BACKGROUND OF THE INVENTION

Biodistribution studies provide useful insight into the mechanism of delivery of therapeutic vehicles. Such studies generally employ bioimaging dyes. For deep tissue imaging, certain detection wavelengths are desired, e.g., the deep red to near-infrared (NIR) spectral region to avoid background autofluorescence from tissue and other biological components.

Identifying useful imaging dyes in the deep red to NIR region remain a challenge. Ideally, such dyes would have extended lifetimes to allow for long-term in vivo studies. Furthermore, the dyes should be minimally toxic for such animal studies. Thus, there is a need for additional materials having such characteristics.

SUMMARY OF THE INVENTION

The present invention provides a multifunctional metal-organic framework (MOF) material that displays both porosity and tunable emission properties. Such materials can be incorporated in any composition or construct, as described herein. In particular embodiments, the MOF material possess an emission signal (e.g., a maximal emission peak) in the deep red to NIR spectral region (e.g., of from about 600 nm to about 1500 nm, including of from about 614 nm to about 1350 nm).

In non-limiting embodiments, the MOF material has beneficial toxicity properties. In one instance, the MOF material is minimally toxic to living cells.

There is also an interest in providing MOF materials having beneficial structural properties. Exemplary properties include a tunable emission signal (e.g., based on the metal ion), enhanced structural integrity in aqueous solutions (e.g., water, a buffer, plasma, blood, etc.), ease of processability (e.g., removal of solvate molecules by heating, thereby providing uncoordinated metal sites useful for tuning guest-framework interactions, included but not limited to drug delivery, catalysis, gas sensing, gas adsorption, and gas separation), and/or controllable porosity (e.g., enabling loading of cargo(s) into the MOF itself).

In particular examples, we describe the synthesis and characterization of a MOF materials platform based on rare earth metal ions (e.g., RE=Eu, Nd, Yb, Y, Tb, as well as tuned compositions of including both Nd and Yb, e.g., Nd0.67/Yb0.33 or Nd0.46/Yb0.54) and a linear carboxylic acid/carboxylate ligand (e.g., a dicarboxylic acid, such 2,5-dihydroxyterephthalic acid). Importantly, these compositions can be easily extended to other RE metal ions, including but not limited to La, Ce, Pr, Sm, Gd, Dy, Ho, Er, Tm, and Lu.

In a first aspect, the present invention features a metal-organic framework composition including a plurality of metal clusters and a plurality of ligands coordinating with the plurality of metal clusters, wherein at least one metal cluster includes a metal ion, at least one ligand is a monodentate ligand, and at least one ligand is a bidentate ligand. In some embodiments, at least one metal cluster includes a hexanuclear cluster.

In some embodiments, the metal ion is a rare earth metal ion and wherein the rare earth metal ion is selected from the group consisting of Eu, Nd, Yb, Y, Tb, La, Ce, Pr, Sm, Gd, Dy, Ho, Er, Tm, and Lu.

In some embodiments, the plurality of metal clusters includes a first metal ion and a second metal ion that is different than the first metal ion. In particular embodiments, the plurality of metal clusters includes a first metal ion having a first coordination geometry and a second metal ion having a second coordination geometry that is different than the first coordinate geometry.

In some embodiments, the composition includes a plurality of monodentate ligands and a plurality of bidentate ligands. In some embodiments, each of the monodentate ligands and the each of the bidentate ligands includes a structure of $L^1$-$R^L$-$L^2$, wherein each of $L^1$ and $L^2$ is, independently, a reactive group, and wherein $R^L$ is a linker. In further embodiments, $R^L$ includes an optionally substituted aryl or an optionally substituted heteroaryl. In other embodiments, each of $L^1$ and $L^2$ includes, independently, carboxyl, heterocyclyl, hydroxyl, an anion thereof, a salt thereof, or an ester thereof (e.g., any described herein). In yet other embodiments, a linker of at least one of the plurality of monodentate ligand is the same as a linker of at least one of the plurality of bidentate ligands.

In some embodiments, the plurality of metal clusters and plurality of ligands form a periodic framework and/or are characterized by a tetragonal crystal structure.

In some embodiments, the plurality of metal clusters and the plurality of ligands is provided within a particle, a coated particle, a core-shell particle, or a lipid-coated particle. In other embodiments, the composition further includes one or more cargos (e.g., any described herein) disposed in proximity to and/or within the at least one metal cluster.

In a second aspect, the present invention features a construct including: a metal-organic framework (MOF) composition including a plurality of metal clusters and a plurality of ligands coordinating with the plurality of metal clusters, wherein at least one metal cluster includes a metal ion, at least one ligand is a monodentate ligand, and at least one ligand is a bidentate ligand; and an outer layer. In some embodiments, the outer layer includes a polymer, a lipid, a lipid layer, an organic matrix, an inorganic matrix, and/or a shell, wherein the outer layer is disposed directly or indirectly on a surface of the MOF composition.

In some embodiments, the construct includes one or more cargos (e.g., any described herein) disposed in proximity to and/or within the MOF composition and/or the outer layer.

In some embodiments, the MOF composition is provided as one or more cores, and wherein the outer layer is disposed on an external surface, or a portion thereof, of the one or more cores.

In some embodiments, the outer layer includes a lipid monolayer, a lipid bilayer, a lipid multilayer, a shell, and/or a shielding layer.

In a third aspect, the present invention features a formulation including a composition (e.g., any described herein), or a salt or an anhydrate or a solvate thereof, and a pharmaceutically acceptable excipient (e.g., any described herein).

In a fourth aspect, the present invention features a formulation including a construct (e.g., any described herein), or a salt or an anhydrate or a solvate thereof, and a pharmaceutically acceptable excipient (e.g., any described herein).

In a fifth aspect, the present invention features a method of treating a cell or a subject (e.g., a human subject), the method including: exposing the cell or the subject to a formulation (e.g., any described herein); and detecting an emission signal of the composition or the construct.

In a fifth aspect, the present invention features a method of delivering a cargo (e.g., any described herein), the method including: exposing the cell or a subject (e.g., a human subject) to a formulation (e.g., any described herein), wherein the composition or the construct further includes one or more cargos. In some embodiments, the composition or the construct or the formulation further includes one or more targeting ligands.

In a sixth aspect, the present invention features a method of treating (e.g., or treating prophylactically) a disease, the method including: exposing a cell or a subject (e.g., a human subject) to a formulation (e.g., any described herein), wherein the composition or the construct or the formulation further includes one or more cargos in an amount sufficient to treat the disease.

In a seventh aspect, the present invention features a method of forming a metal-organic framework composition, the method including: providing a mixture including a metal ion source and a ligand source; and reacting the mixture to provide a composition including a plurality of metal clusters and a plurality of ligands coordinating with the plurality of metal clusters. In some embodiments, at least one metal cluster includes a metal ion, at least one ligand is a monodentate ligand, and at least one ligand is a bidentate ligand.

In some embodiments, the mixture further includes a modulating agent (e.g., any described herein).

In some embodiments, the reacting step further includes exposing the mixture to microwaves or ultrasonic waves.

In some embodiments, the method further includes (e.g., after the reacting step): removing a solvent that is coordinated to at least one metal cluster, thereby providing a coordinatively unsaturated metal center.

In some embodiments, the method further includes (e.g., after the reacting step): loading the composition with one or more cargos; and optionally depositing one or more outer layers directly or indirectly on a surface of the composition, thereby providing a loaded construct.

In some embodiments, the method further includes (e.g., after the reacting step): depositing a first outer layer on a surface of the composition; and optionally depositing a second outer layer on a surface of the first outer layer, thereby providing a construct.

In some embodiments, each of the first and second outer layers, independently, includes a polymer, a lipid, a lipid layer, an organic matrix, an inorganic matrix, or a shell. In other embodiments, the first outer layer includes an inorganic matrix and the second outer layer includes a lipid.

In some embodiments, the method further includes (e.g., after the depositing step, such as of the first outer layer): loading the composition with one or more cargos.

In some embodiments, the method further includes (e.g., after the reacting step): depositing a first outer layer on a surface of the composition; loading the composition with one or more cargos; and depositing a second outer layer on a surface of the first outer layer, thereby providing a construct.

Additional details follow.

Definitions

As used herein, the term "about" means+/−10% of any recited value. As used herein, this term modifies any recited value, range of values, or endpoints of one or more ranges.

By "alkoxy" is meant —OR, where R is an optionally substituted alkyl group, as described herein. Exemplary alkoxy groups include methoxy, ethoxy, butoxy, trihaloalkoxy, such as trifluoromethoxy, etc. The alkoxy group can be substituted or unsubstituted. For example, the alkoxy group can be substituted with one or more substitution groups, as described herein for alkyl. Exemplary unsubstituted alkoxy groups include $C_{1-3}$, $C_{1-6}$, $C_{1-12}$, $C_{1-16}$, $C_{1-18}$, $C_{1-20}$, or $C_{1-24}$ alkoxy groups.

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{1-6}$ alkoxy (e.g., —OAk, in which Ak is an alkyl group, as defined herein); (2) $C_{1-6}$ alkylsulfinyl (e.g., —S(O)Ak, in which Ak is an alkyl group, as defined herein); (3) $C_{1-6}$ alkylsulfonyl (e.g., —SO$_2$Ak, in which Ak is an alkyl group, as defined herein); (4) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (5) aryl; (6) arylalkoxy (e.g., —OA$^L$Ar, in which A$^L$ is an alkylene group and Ar is an aryl group, as defined herein); (7) aryloyl (e.g., —C(O)Ar, in which Ar is an aryl group, as defined herein); (8) azido (e.g., an —N$_3$ group); (9) cyano (e.g., a —CN group); (10) carboxyaldehyde (e.g., a —C(O)H group); (11) $C_{3-8}$ cycloalkyl; (12) halo; (13) heterocyclyl (e.g., a 5-, 6- or 7-membered ring, unless otherwise specified, containing one, two, three, or four non-carbon heteroatoms (e.g., independently selected from the group consisting of nitrogen, oxygen, phosphorous, sulfur, or halo)); (14) heterocyclyloxy (e.g., —OHet, in which Het is a heterocyclyl group); (15) heterocyclyloyl (e.g., —C(O)Het, in which Het is a heterocyclyl group); (16) hydroxyl (e.g., a —OH group); (17) N-protected amino; (18) nitro (e.g., an —NO$_2$ group); (19) oxo (e.g., an =O group); (20) $C_{3-8}$ spirocyclyl (e.g., an alkylene diradical, both ends of which are bonded to the same carbon atom of the parent group to form a spirocyclyl group); (21) $C_{1-6}$ thioalkoxy (e.g., —SAk, in which Ak is an alkyl group, as defined herein); (22) thiol (e.g., an —SH group); (23) —CO$_2$R$^A$, where R$^A$ is selected from the group consisting of (a) hydrogen, (b) C$_{1-6}$ alkyl, (c) C$_{4-18}$ aryl, and (d) C$_{1-6}$ alk-C$_{4-18}$ aryl; (24) —C(O)NR$^B$R$^C$, where each of R$^B$ and R$^C$ is, independently, selected from the group consisting of (a) hydrogen, (b) C$_{1-6}$ alkyl, (c) C$_{4-18}$ aryl, and (d) C$_{1-6}$ alk-C$_{4-18}$ aryl; (25) —SO$_2$R$^D$, where R$^D$ is selected from the group consisting of (a) C$_{1-6}$ alkyl, (b) C$_{4-18}$ aryl, and (c) C$_{1-6}$ alk-C$_{4-18}$ aryl; (26) —SO$_2$NR$^E$R$^F$, where each of R$^E$ and R$^F$ is, independently, selected from the group consisting of (a) hydrogen, (b) C$_{1-6}$ alkyl, (c) C$_{4-18}$ aryl, and (d) C$_{1-6}$ alk-C$_{4-18}$ aryl; and (27) —NR$^G$R$^H$, where each of R$^G$ and R$^H$ is, independently, selected from the group consisting of (a) hydrogen, (b) an N-protecting group, (c) C$_{1-6}$ alkyl, (d) C$_{2-6}$ alkenyl, (e) C$_{2-6}$ alkynyl, (f) C$_{4-18}$ aryl, (g) C$_{1-6}$ alk-C$_{4-18}$ aryl, (h) C$_{3-8}$ cycloalkyl, and (i) C$_{1-6}$ alk-C$_{3-8}$ cycloalkyl, wherein in one embodiment no two groups are bound to the nitrogen atom through a carbonyl group or a sulfonyl group. The alkyl group can be a primary, secondary, or tertiary alkyl group substituted with one or more substituents (e.g., one or more halo or alkoxy). In some embodiments, the unsubstituted alkyl group is a C$_{1-3}$, C$_{1-6}$, C$_{1-12}$, C$_{1-16}$, C$_{1-18}$, C$_{1-20}$, or C$_{1-24}$ alkyl group.

By "alkylene" is meant a multivalent (e.g., bivalent, trivalent, tetravalent, etc.) form of an alkyl group, as described herein. Exemplary alkylene groups include methylene, ethylene, propylene, butylene, etc. In some embodiments, the alkylene group is a C$_{1-3}$, C$_{1-6}$, C$_{1-12}$, C$_{1-16}$, C$_{1-18}$, C$_{1-20}$, C$_{1-24}$, C$_{2-3}$, C$_{2-6}$, C$_{2-12}$, C$_{2-16}$, C$_{2-18}$, C$_{2-20}$, or C$_{2-24}$ alkylene group. The alkylene group can be branched or unbranched. The alkylene group can also be substituted or unsubstituted. For example, the alkylene group can be substituted with one or more substitution groups, as described herein for alkyl.

By "amino" is meant —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group, as defined herein.

By "aminoalkyl" is meant an alkyl group, as defined herein, substituted by an amino group, as defined herein.

By "aryl" is meant a group that contains any carbon-based aromatic group including, but not limited to, benzyl, naphthalene, phenyl, biphenyl, phenoxybenzene, anthracene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one, two, three, four, or five substituents independently selected from the group consisting of: (1) C$_{1-6}$ alkanoyl (e.g., —C(O)Ak, in which Ak is an alkyl group, as defined herein); (2) C$_{1-6}$ alkyl; (3) C$_{1-6}$ alkoxy (e.g., —OAk, in which Ak is an alkyl group, as defined herein); (4) C$_{1-6}$ alkoxy-C$_{1-6}$ alkyl (e.g., an alkyl group, which is substituted with an alkoxy group —OAk, in which Ak is an alkyl group, as defined herein); (5) C$_{1-6}$ alkylsulfinyl (e.g., —S(O)Ak, in which Ak is an alkyl group, as defined herein); (6) C$_{1-6}$ alkylsulfinyl-C$_{1-6}$ alkyl (e.g., an alkyl group, which is substituted by an alkylsulfinyl group —S(O)Ak, in which Ak is an alkyl group, as defined herein); (7) C$_{1-6}$ alkylsulfonyl (e.g., —SO$_2$Ak, in which Ak is an alkyl group, as defined herein); (8) C$_{1-6}$ alkylsulfonyl-C$_{1-6}$ alkyl (e.g., an alkyl group, which is substituted by an alkylsulfonyl group —SO$_2$Ak, in which Ak is an alkyl group, as defined herein); (9) aryl; (10) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (11) C$_{1-6}$ aminoalkyl (e.g., meant an alkyl group, as defined herein, substituted by an amino group); (12) heteroaryl; (13) C$_{1-6}$ alk-C$_{4-18}$ aryl (e.g., -A$^L$Ar, in which A$^L$ is an alkylene group and Ar is an aryl group, as defined herein); (14) aryloyl (e.g., —C(O)Ar, in which Ar is an aryl group, as defined herein); (15) azido (e.g., an —N$_3$ group); (16) cyano (e.g., a —CN group); (17) C$_{1-6}$ azidoalkyl (e.g., a —N$_3$ azido group attached to the parent molecular group through an alkyl group, as defined herein); (18) carboxyaldehyde (e.g., a —C(O)H group); (19) carboxyaldehyde-C$_{1-6}$ alkyl (e.g., -A$^L$C(O)H, in which A$^L$ is an alkylene group, as defined herein); (20) C$_{3-8}$ cycloalkyl; (21) C$_{1-6}$ alk-C$_{3-8}$ cycloalkyl (e.g., -A$^L$Cy, in which A$^L$ is an alkylene group and Cy is a cycloalkyl group, as defined herein); (22) halo (e.g., F, Cl, Br, or I); (23) C$_{1-6}$haloalkyl (e.g., an alkyl group, as defined herein, substituted with one or more halo); (24) heterocyclyl; (25) heterocyclyloxy (e.g., —OHet, in which Het is a heterocyclyl group); (26) heterocyclyloyl (e.g., —C(O)Het, in which Het is a heterocyclyl group); (16) hydroxyl (e.g., a —OH group); (27) hydroxyl (e.g., a —OH group); (28) C$_{1-6}$hydroxyalkyl (e.g., an alkyl group, as defined herein, substituted by one to three hydroxyl groups, with the proviso that no more than one hydroxyl group may be attached to a single carbon atom of the alkyl group); (29) nitro (e.g., an —NO$_2$ group); (30) C$_{1-6}$nitroalkyl (e.g., an alkyl group, as defined herein, substituted by one to three nitro groups); (31) N-protected amino; (32) N-protected amino-C$_{1-6}$ alkyl; (33) oxo (e.g., an =O group); (34) C$_{1-6}$ thioalkoxy (e.g., —SAk, in which Ak is an alkyl group, as defined herein); (35) thio-C$_{1-6}$ alkoxy-C$_{1-6}$ alkyl (e.g., an alkyl group, which is substituted by an thioalkoxy group —SAk, in which Ak is an alkyl group, as defined herein); (36) —(CH$_2$)$_r$CO$_2$R$^A$, where r is an integer of from zero to four, and R$^A$ is selected from the group consisting of (a) hydrogen, (b) C$_{1-6}$ alkyl, (c) C$_{4-18}$ aryl, and (d) C$_{1-6}$ alk-C$_{4-18}$ aryl; (37) —(CH$_2$)$_r$CONR$^B$R$^C$, where r is an integer of from zero to four and where each R$^B$ and R$^C$ is independently selected from the group consisting of (a) hydrogen, (b) C$_{1-6}$ alkyl, (c) C$_{4-18}$ aryl, and (d) C$_{1-6}$ alk-C$_{4-18}$ aryl; (38) —(CH$_2$)$_r$SO$_2$R$^D$, where r is an integer of from zero to four and where R$^D$ is selected from the group consisting of (a) C$_{1-6}$ alkyl, (b) C$_{4-18}$ aryl, and (c) C$_{1-6}$ alk-C$_{4-18}$ aryl; (39) —(CH$_2$)$_r$SO$_2$NR$^E$R$^F$, where r is an integer of from zero to four and where each of R$^E$ and R$^F$ is, independently, selected from the group consisting of (a) hydrogen, (b) C$_{1-6}$ alkyl, (c) C$_{4-18}$ aryl, and (d) C$_{1-6}$ alk-C$_{4-18}$ aryl; (40) —(CH$_2$)$_r$NR$^G$R$^H$, where r is an integer of from zero to four and where each of R$^G$ and R$^H$ is, independently, selected from the group consisting of (a) hydrogen, (b) an N-protecting group, (c) C$_{1-6}$ alkyl, (d) C$_{2-6}$ alkenyl, (e) C$_{2-6}$ alkynyl, (f) C$_{4-18}$ aryl, (g) C$_{1-6}$ alk-C$_{4-18}$ aryl, (h) C$_{3-8}$ cycloalkyl, and (i) C$_{1-6}$ alk-C$_{3-8}$ cycloalkyl, wherein in one embodiment no two groups are bound to the nitrogen atom through a carbonyl group or a sulfonyl group; (41) thiol; (42) perfluoroalkyl (e.g., an alkyl group, as defined herein, having each hydrogen atom substituted with a fluorine atom); (43) perfluoroalkoxy (e.g., —ORf, in which Rf is an alkyl group, as defined herein, having each hydrogen atom substituted with a fluorine atom); (44) aryloxy (e.g., —OAr, where Ar is an optionally substituted aryl group, as described herein); (45)

cycloalkoxy (e.g., —OCy, in which Cy is a cycloalkyl group, as defined herein); (46) cycloalkylalkoxy (e.g., —OA$^L$Cy, in which A$^L$ is an alkylene group and Cy is a cycloalkyl group, as defined herein); and (47) arylalkoxy (e.g., —OA$^L$Ar, in which A$^L$ is an alkylene group and Ar is an aryl group, as defined herein). In particular embodiments, an unsubstituted aryl group is a $C_{4-18}$, $C_{4-14}$, $C_{4-12}$, $C_{4-10}$, $C_{6-18}$, $C_{6-14}$, $C_{6-12}$, or $C_{6-10}$ aryl group.

By "arylene" is meant a multivalent (e.g., bivalent, trivalent, tetravalent, etc.) form of an aryl group, as described herein. Exemplary arylene groups include phenylene, naphthylene, biphenylene, triphenylene, diphenyl ether, acenaphthenylene, anthrylene, or phenanthrylene. In some embodiments, the arylene group is a $C_{4-18}$, $C_{4-14}$, $C_{4-12}$, $C_{4-10}$, $C_{6-18}$, $C_{6-14}$, $C_{6-12}$, or $C_{6-10}$ arylene group. The arylene group can be branched or unbranched. The arylene group can also be substituted or unsubstituted. For example, the arylene group can be substituted with one or more substitution groups, as described herein for aryl.

By "aryloxy" is meant —OR, where R is an optionally substituted aryl group, as described herein. In some embodiments, an unsubstituted aryloxy group is a $C_{4-18}$ or $C_{6-18}$ aryloxy group.

By "aryloxycarbonyl" is meant an aryloxy group, as defined herein, that is attached to the parent molecular group through a carbonyl group. In some embodiments, an unsubstituted aryloxycarbonyl group is a $C_{5-19}$ aryloxycarbonyl group.

By "aryloyl" is meant an aryl group that is attached to the parent molecular group through a carbonyl group. In some embodiments, an unsubstituted aryloyl group is a $C_{7-11}$ aryloyl group.

By "azido" is meant an —$N_3$ group.

By "azo" is meant an —N=N— group.

By "carbonyl" is meant a —C(O)— group, which can also be represented as >C=O.

By "carboxyaldehyde" is meant a —C(O)H group.

By "carboxyl" is meant a —$CO_2$H group.

By "cyano" is meant a —CN group.

By "cycloalkyl" is meant a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1.]heptyl and the like. The cycloalkyl group can also be substituted or unsubstituted. For example, the cycloalkyl group can be substituted with one or more groups including those described herein for alkyl.

By "cycloalkoxy" is meant a cycloalkyl group, as defined herein, attached to the parent molecular group through an oxygen atom.

By "halo" is meant F, Cl, Br, or I.

By "haloalkyl" is meant an alkyl group, as defined herein, substituted with one or more halo.

By "heteroalkyl" is meant an alkyl group, as defined herein, containing one, two, three, or four non-carbon heteroatoms (e.g., independently selected from the group consisting of nitrogen, oxygen, phosphorous, sulfur, or halo).

By "heteroalkylene" is meant a divalent form of an alkylene group, as defined herein, containing one, two, three, or four non-carbon heteroatoms (e.g., independently selected from the group consisting of nitrogen, oxygen, phosphorous, sulfur, or halo).

By "heteroaryl" is meant a subset of heterocyclyl groups, as defined herein, which are aromatic, i.e., they contain 4n+2 pi electrons within the mono- or multicyclic ring system.

By "heterocyclyl" is meant a 5-, 6- or 7-membered ring, unless otherwise specified, containing one, two, three, or four non-carbon heteroatoms (e.g., independently selected from the group consisting of nitrogen, oxygen, phosphorous, sulfur, or halo). The 5-membered ring has zero to two double bonds and the 6- and 7-membered rings have zero to three double bonds. The term "heterocyclyl" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring, and another monocyclic heterocyclic ring, such as indolyl, quinolyl, isoquinolyl, tetrahydroquinolyl, benzofuryl, benzothienyl and the like. Heterocyclics include thiiranyl, thietanyl, tetrahydrothienyl, thianyl, thiepanyl, aziridinyl, azetidinyl, pyrrolidinyl, piperidinyl, azepanyl, pyrrolyl, pyrrolinyl, pyrazolyl, pyrazolinyl, pyrazolidinyl, imidazolyl, imidazolinyl, imidazolidinyl, pyridyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazolyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl, and the like.

By "hydroxyl" is meant —OH.

By "hydroxyalkyl" is meant an alkyl group, as defined herein, substituted by one to three hydroxyl groups, with the proviso that no more than one hydroxyl group may be attached to a single carbon atom of the alkyl group and is exemplified by hydroxymethyl, dihydroxypropyl, and the like.

By "nitro" is meant an —$NO_2$ group.

By "nitroalkyl" is meant an alkyl group, as defined herein, substituted by one to three nitro groups.

By "nitroso" is meant an —NO group.

By "oxo" is meant an =O group.

By "oxy" is meant —O—.

By "perfluoroalkyl" is meant an alkyl group, as defined herein, having each hydrogen atom substituted with a fluorine atom. Exemplary perfluoroalkyl groups include trifluoromethyl, pentafluoroethyl, etc.

By "perfluoroalkylene" is meant an alkylene group, as defined herein, having each hydrogen atom substituted with a fluorine atom. Exemplary perfluoroalkylene groups include difluoromethylene, tetrafluoroethylene, etc.

By "perfluoroalkyleneoxy" is meant a perfluoroalkylene group, as defined herein, having an oxy group attached to either end of the perfluoroalkylene group. Exemplary perfluoroalkylene groups include, e.g., —$OC_fF_{2f}$— or —$C_fF_{2f}O$—, where f is an integer from about 1 to 5, and 2f is an integer that is 2 times f (e.g., difluoromethyleneoxy, tetrafluoroethyleneoxy, etc.).

By "perfluoroalkoxy" is meant an alkoxy group, as defined herein, having each hydrogen atom substituted with a fluorine atom.

By "phosphono" is meant a —P(O)(OH)$_2$ group.

By "phosphonoyl" is meant a —P(O)H— group.

By "phosphoric ester" is meant a —O—PO(OH)$_2$ group.

By "phosphoryl" is meant a —P(O)< group.

By "protecting group" is meant any group intended to protect a reactive group against undesirable synthetic reactions. Commonly used protecting groups are disclosed in "Greene's Protective Groups in Organic Synthesis," John Wiley & Sons, New York, 2007 (4th ed., eds. P. G. M. Wuts and T. W. Greene), which is incorporated herein by reference. O-protecting groups include an optionally substituted alkyl group (e.g., forming an ether with reactive group O), such as methyl, methoxymethyl, methylthiomethyl, benzoyloxymethyl, t-butoxymethyl, etc.; an optionally substituted alkanoyl group (e.g., forming an ester with the reactive group O), such as formyl, acetyl, chloroacetyl, fluoroacetyl (e.g., perfluoroacetyl), methoxyacetyl, pivaloyl, t-butylacetyl, phenoxyacetyl, etc.; an optionally substituted aryloyl group (e.g., forming an ester with the reactive group O), such as —C(O)—Ar, including benzoyl; an optionally substituted alkylsulfonyl group (e.g., forming an alkylsulfonate with reactive group O), such as —SO$_2$—R$^{S1}$, where R$^{S1}$ is optionally substituted C$_{1-12}$ alkyl, such as mesyl or benzylsulfonyl; an optionally substituted arylsulfonyl group (e.g., forming an arylsulfonate with reactive group O), such as —SO$_2$—R$^{S4}$, where R$^{S4}$ is optionally substituted C$_{4-18}$ aryl, such as tosyl or phenylsulfonyl; an optionally substituted alkoxycarbonyl or aryloxycarbonyl group (e.g., forming a carbonate with reactive group O), such as —C(O)—OR$^{T1}$, where R$^{T1}$ is optionally substituted C$_{1-12}$ alkyl or optionally substituted C$_{4-18}$ aryl, such as methoxycarbonyl, methoxymethylcarbonyl, t-butyloxycarbonyl (Boc), or benzyloxycarbonyl (Cbz); or an optionally substituted silyl group (e.g., forming a silyl ether with reactive group O), such as —Si—(R$^{T2}$)$_3$, where each R$^{T2}$ is, independently, optionally substituted C$_{1-12}$ alkyl or optionally substituted C$_{4-18}$ aryl, such as trimethylsilyl, t-butyldimethylsilyl, or t-butyldiphenylsilyl. N-protecting groups include, e.g., formyl, acetyl, benzoyl, pivaloyl, t-butylacetyl, alanyl, phenylsulfonyl, benzyl, Boc, and Cbz. Such protecting groups can employ any useful agent to cleave the protecting group, thereby restoring the reactivity of the unprotected reactive group.

By "salt" is meant an ionic form of a compound or structure (e.g., any formulas, compounds, or compositions described herein), which includes a cation or anion compound to form an electrically neutral compound or structure. Salts are well known in the art. For example, non-toxic salts are described in Berge S M et al., "Pharmaceutical salts," *J. Pharm. Sci.* 1977 January; 66(1):1-19; and in "Handbook of Pharmaceutical Salts: Properties, Selection, and Use," Wiley-VCH, April 2011 (2nd rev. ed., eds. P. H. Stahl and C. G. Wermuth. The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine. Yet other salts include pharmaceutically acceptable salts, as described herein.

By "solvate" is meant a stabilized form of a compound or structure (e.g., any formulas, compounds, or compositions described herein, including anionic or cationic forms thereof) with one or more solvent molecules. Such forms can be stabilized by any useful interaction, such as electrostatic forces, van der Waals forces, or hydrogen bond formation. Exemplary solvates include hydrates (including one or more water molecules).

By "sulfinyl" is meant an —S(O)— group.

By "sulfo" is meant an —S(O)$_2$OH group.

By "sulfonyl" is meant an —S(O)$_2$— group.

By "anhydrate" is meant a form of a compound or structure (e.g., any formulas, compounds, or compositions described herein) generally lacking solvent molecules.

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

By "pharmaceutically acceptable excipient" is meant any ingredient other than a compound or structure (e.g., any formulas, compounds, or compositions described herein) and having the properties of being nontoxic and non-inflammatory in a subject. Exemplary, non-limiting excipients include adjuvants, antiadherents, antioxidants, binders, carriers, coatings, compression aids, diluents, disintegrants, dispersing agents, dyes (colors), emollients, emulsifiers, fillers (diluents), film formers or coatings, flavors, fragrances, glidants (flow enhancers), isotonic carriers, lubricants, preservatives, printing inks, solvents, sorbents, stabilizers, suspending or dispersing agents, surfactants, sweeteners, waters of hydration, or wetting agents. Any of the excipients can be selected from those approved, for example, by the United States Food and Drug Administration or other governmental agency as being acceptable for use in humans or domestic animals. Exemplary excipients include, but are not limited to alcohol, butylated hydroxytoluene (BHT), calcium carbonate, calcium phosphate (dibasic), calcium stearate, cellulose, croscarmellose, cross-linked polyvinyl pyrrolidone, citric acid, crospovidone, cysteine, ethylcellulose, gelatin, glucose, glycerol, hydroxypropyl cellulose, hydroxypropyl methylcellulose, lactated Ringer's solution, lactose, magnesium carbonate, magnesium stearate, maltitol, maltose, mannitol, methionine, methylcellulose, methyl paraben, microcrystalline cellulose, polyethylene glycol, polyol, polyvinyl pyrrolidone, povidone, pregelatinized starch, propyl paraben, retinyl palmitate, Ringer's solution, shellac, silicon dioxide, sodium carboxymethyl cellulose, sodium chloride injection, sodium citrate, sodium saccharine, sodium starch glycolate, sorbitol, starch (corn), stearic acid, stearic acid, sucrose, talc, talcum, titanium dioxide, vegetable oil, vitamin A, vitamin E, vitamin C, water, and xylitol.

By "pharmaceutically acceptable salt" is meant a salt that is, within the scope of sound medical judgment, suitable for use in contact with the tissues of humans and animals without undue toxicity, irritation, allergic response and the like and are commensurate with a reasonable benefit/risk ratio.

By "isomer" is meant a molecule having the same molecular formula as the reference molecule. Exemplary isomers include stereoisomers, diastereomers, enantiomers, geometric isomers, tautomers, as well as mixtures thereof.

By an "effective amount" or a "sufficient amount" of an agent (e.g., a composition, a construct, a formulation, and/or a cargo), as used herein, is that amount sufficient to effect beneficial or desired results, such as clinical results, and, as such, an "effective amount" depends upon the context in which it is being applied. For example, in the context of administering an agent that is an inhibitor of an enzyme, an effective amount of an agent is, for example, an amount sufficient to achieve a reduction in that enzyme or its activity, as compared to the response obtained without administration of the agent.

By "subject" is meant a human or non-human animal (e.g., a mammal).

By "treating" a disease, disorder, or condition in a subject is meant reducing at least one symptom of the disease, disorder, or condition by administrating a therapeutic agent to the subject. By "treating prophylactically" a disease, disorder, or condition in a subject is meant reducing the frequency of occurrence of or reducing the severity of a disease, disorder or condition by administering a therapeutic agent to the subject prior to the onset of disease symptoms. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable.

Other features and advantages of the invention will be apparent from the following description and the claims.

DETAILED DESCRIPTION OF THE INVENTION

The present invention relates to composition containing a MOF composition including a plurality of metal clusters and a plurality of ligands coordinating with the plurality of metal clusters (e.g., as described herein). In particular embodiments, the MOF composition exhibits minimal toxicity, as determined by in vitro or in vivo assays. In yet other embodiments, the MOF composition is characterized by an emission signal (e.g., a peak emission signal, including a maximum signal or a local maximum signal) that is in the range of deep red to NIR wavelengths.

FIG. 1A-1D provides an exemplary MOF composition. As can be seen, the exemplary MOF composition has a periodic framework (FIG. 1C) having a general formula of EuDOBDC $(Eu_6(\mu_3\text{-}OH)_8(C_8H_4O_6)_5(C_8H_6O_6)_1(H_2O)_6 \cdot 24H_2O)$. Other metal clusters were synthesized and characterized, as described herein.

Figure 2A:
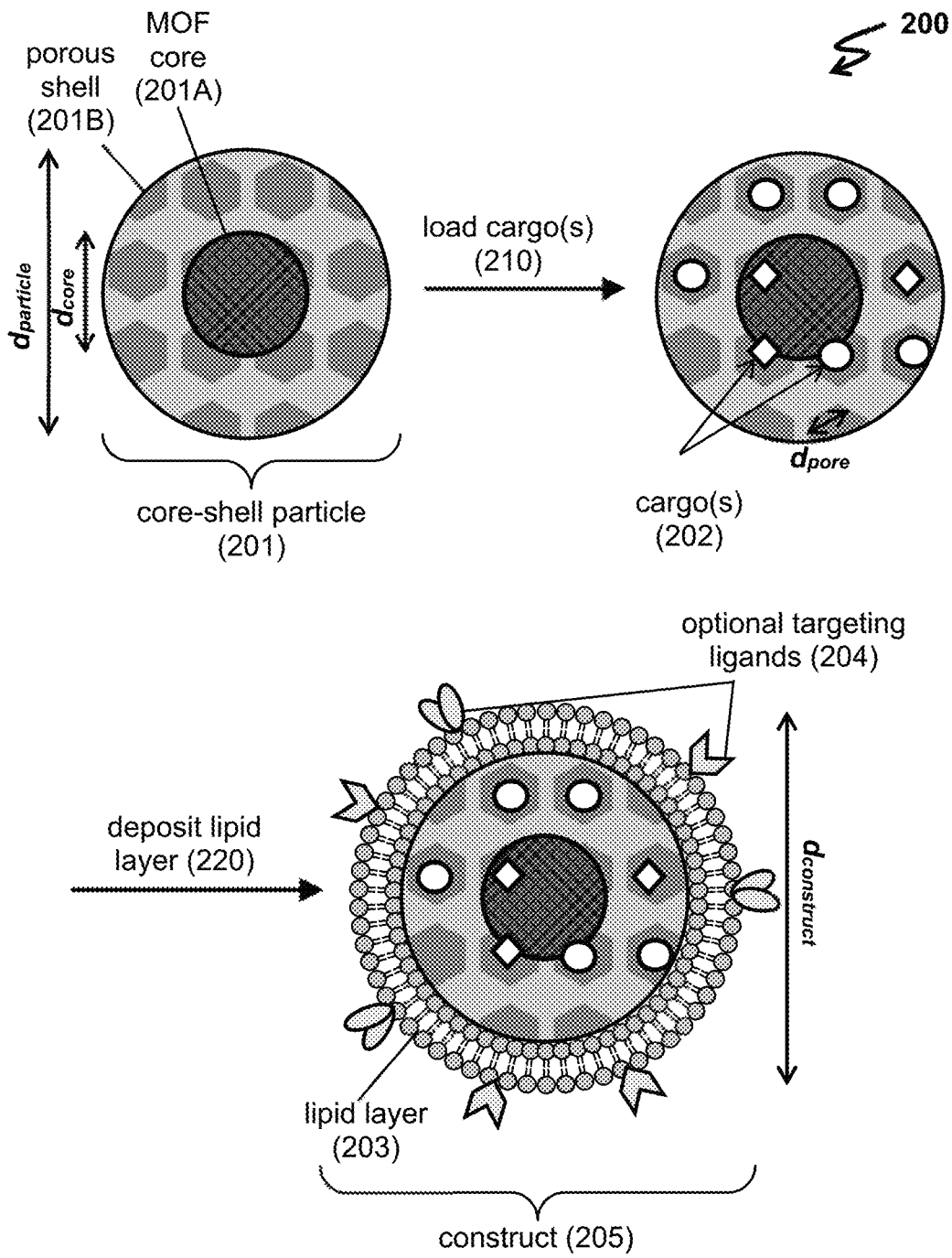
FIG. 2A-2B shows exemplary constructs. Provided are an exemplary method 200 for making a construct (FIG. 2A) and a schematic of other exemplary constructs 2100-2700 (FIG. 2B).

The MOF composition can be provided in any useful construct, such as a particle. FIG. 2A provides exemplary particles, including an exemplary core-shell particle 201 and an exemplary construct 205.

The construct can be formed in any useful manner. As seen in the method 200 of FIG. 2A, a MOF core 201A having a dimension $d_{core}$ is first provided. Exemplary values for dimension $d_{core}$ include, without limitation, greater than about 10 nm (e.g., greater than about 20 nm, 30 nm, 40 nm, 50 nm, 60 nm, 70 nm, 80 nm, 90 nm, 100 nm, 125 nm, 150 nm, 200 nm, 300 nm, 500 nm, 750 nm, 1 µm, 2 µm, 5 µm, 10 µm, 20 µm, or more) or of from about 10 nm to about 100 nm (e.g., from 10 nm to 50 nm, 20 nm to 50 nm, 20 nm to 100 nm, 30 nm to 100 nm, etc.). The MOF core can optionally include one or more components (e.g., one or more nucleic acid sequences, drugs, proteins, labels, etc., such as any agent described herein).

Then, the MOF core 201A is encapsulated with a shell 201B (e.g., a porous shell) having a thickness $t_s$, thereby providing a particle of dimension $d_{particle}$, thereby forming a core-shell particle 201. The shell can have any useful thickness that allows for controlled biodegradation in vivo, targeted biodistribution, stability in a formulation, and/or consistent fabrication of the construct (or a population of constructs). Exemplary values for dimension $t_s$ include, without limitation, less than about 100 nm (e.g., less than about 0.1 nm, 0.5 nm, 1 nm, 2 nm, 3 nm, 5 nm, 8 nm, 10 nm, 15 nm, 20 nm, 30 nm, 40 nm, 50 nm, 60 nm, 70 nm, 80 nm, 90 nm). Exemplary values for dimension $d_{particle}$ include, without limitation, greater than about 10 nm (e.g., greater than about 20 nm, 30 nm, 40 nm, 50 nm, 60 nm, 70 nm, 80 nm, 90 nm, 100 nm, 125 nm, 150 nm, 200 nm, 300 nm, 500 nm, 750 nm, 1 µm, 2 µm, 5 µm, 10 µm, 20 µm, or more).

Optionally, the method can be adapted to include any other useful component(s) or cargo(s). As seen in the method 200 of FIG. 2A, one or more cargos 202 can be loaded 210 into the MOF core (e.g., if the core is porous) and/or into the shell (if the shell is porous) and/or onto the outer surface of the shell (e.g., if the shell is not porous).

Finally, an optional lipid layer 203 can be deposited 220 on an outer surface of the shell (e.g., thereby forming a construct 205). Furthermore, one or more optional targeting ligands 204 (e.g., any described herein) can be combined and/or co-extruded with the lipid and then deposited as a lipid layer (e.g., a lipid bilayer or a lipid multilayer). The final construct 205 can have any useful dimension $d_{construct}$. Exemplary values for dimension $d_{construct}$ include, without limitation, greater than about 10 nm (e.g., greater than about 20 nm, 30 nm, 40 nm, 50 nm, 60 nm, 70 nm, 80 nm, 90 nm, 100 nm, 125 nm, 150 nm, 200 nm, 300 nm, 500 nm, 750 nm, 1 µm, 2 µm, 5 µm, 10 µm, 20 µm, or more).

Figure 2B:
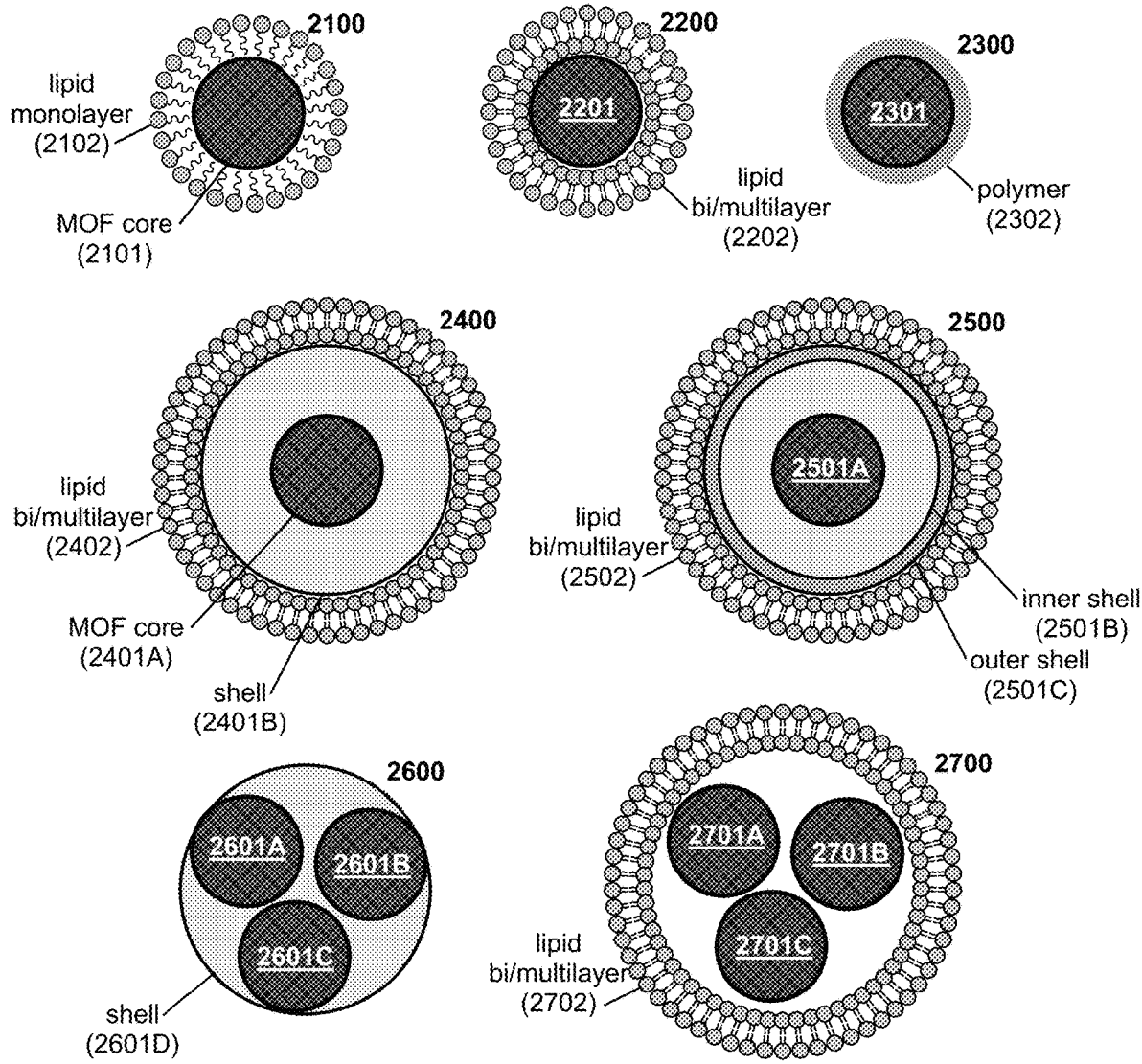

Other constructs can be employed. FIG. 2B provides exemplary constructs including a MOF composition. Provided are a micelle construct 2100 including a MOF core 2101 and a lipid layer (e.g., a lipid monolayer 2102); a liposome construct 2200 including a MOF core 2201 and a lipid layer (e.g., a lipid bilayer or a lipid multilayer 2202); a polymeric construct 2300 including a MOF core 2301 and a polymer layer 2302 (e.g., a conformal polymer layer); a construct 2400 including a MOF core 2401A, a shell 2401B (e.g., a silica shell), and a lipid layer (e.g., a lipid monolayer, bilayer, or multilayer 2402); a core-shell construct 2500 including a MOF core 2501A, an inner shell 2501B (e.g., a silica inner shell, another inorganic inner shell, an organic inner shell, or a polymeric inner shell), an outer shell 2501C (e.g., a silica outer shell, another inorganic outer shell, an organic outer shell, or a polymeric outer shell), and a lipid layer (e.g., a lipid monolayer, bilayer, or multilayer 2502); a multicore construct including a plurality of MOF cores 2601A, 2601B, 2601C and a shell 2601B (e.g., including a matrix of any useful compound, such as an organic, inorganic, and/or polymeric component); and a multicore lipid construct including a plurality of MOF cores 2701A, 2701B, 2701C and a lipid layer (e.g., a lipid monolayer, bilayer, or multilayer 2702). For any of these constructs, a single MOF core can be replaced with a plurality of MOF cores, thereby forming a multicore construct. Furthermore, any construct can include a plurality of shells (e.g., two, three, four, or more shells surrounding the core or plurality of cores). In addition, any construct can include any useful outer layer (e.g., a lipid layer, a polymer layer, etc.).

For any construct, the MOF core can include any useful MOF composition (e.g., any herein) in any useful form (e.g., particle form). In addition, the lipid layer can have any useful form (e.g., lipid monolayer, bilayer, multilayer, etc.) with any useful component (e.g., a lipid component, a mixture of lipids (e.g., any herein), a polymer, a peptide, a targeting ligand, etc.).

Metal Ions and Metal Clusters

The compositions herein can include any useful metal (e.g., a metal ion). The composition can include one metal or a combination of two or more different metals. In addition, the composition can include the same metal having different coordination geometries. Exemplary metals include a rare earth metal, e.g., cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y).

Furthermore, the composition can include one or more metal clusters. Each cluster, in turn, can include a metal ion with one or more ligands. Within a cluster, if a plurality of metal ions is present within the same cluster, each metal ion can be the same or different. Between clusters, the metal ion of a first cluster can be the same or different than the metal ion of a second cluster. Each metal cluster can be the same or different. Exemplary differences can be a different element, a different coordination geometry, a different combination of ligand bridging or chelating, a different ligand, etc.

In one non-limiting embodiment, the cluster includes a plurality of metal ions, in which each metal ion is coordinated to one or more ligands (e.g., a bridging ligand, a chelating ligand, a bridging/chelating ligand). Exemplary ligands include hydroxyl (e.g., $\mu_n$-OH, in which n is 1, 2, 3, etc.), a monodentate ligand, a bidentate ligand (e.g., a bidentate bridging ligand, a bis-bidentate bridging ligand, a bidentate chelating ligand, or a bis-bidentate chelating ligand), a tridentate ligand (e.g., a tridentate bridging ligand or a tridentate chelating ligand), a tetradentate ligand (e.g., a tetradentate bridging ligand or a tetradentate chelating ligand), etc.

In some embodiments, the cluster coordinates with both a monodentate ligand and a bidentate ligand. In other embodiments, the cluster coordinates with a plurality of monodentate ligands and a plurality of bidentate ligands. The clusters and ligands can form any useful network (e.g., a periodic network, in one instance characterized by a tetragonal crystal structure).

Ligands can have any useful structure. In one non-limiting embodiment, the ligand has the structure of $(L^1)_m$-$R^L$-$(L^2)_n$, where each of $L^1$ and $L^2$ is, independently, a reactive group; where $R^L$ is a linker; and where each of m and n is, independently, 1, 2, 3, 4, 5, 6, or one of m or n is 0. For instance, if m and n are both one, then the ligand is a bivalent ligand (e.g., $L^1$-$R^L$-$L^2$). In another instance, if m is 1 and n is 2, then the ligand is a trivalent ligand (e.g., $L^1$-$R^L$-$(L^2)_2$ or $L^1$-$R^L$<$L^{2a}L_{2b}$, in which each $L^2$ is the same or different or in which $L^{2a}$ and $L^{2b}$ are the same or different).

$L^1$ and $L^2$ can be any useful reactive group, such as any useful for forming a metal bond (e.g., a coordinate bond, a covalent bond, etc.). Exemplary reactive groups can include carboxyl, heterocyclyl, amino, phosphoryl, sulfonyl, as well as anionic forms thereof (e.g., carboxylate, azolate (e.g., such as imidazolate, pyrazolate, triazolate, tetrazolate), phosphate, sulfonate, sulfate, etc.), salts thereof, or esters thereof.

The ligand can have any useful linker (e.g., $R^L$). Exemplary linkers can include an optionally substituted aryl (e.g., optionally substituted arylene), optionally substituted heteroaryl (e.g., optionally substituted heteroarylene), an optionally substituted alkyl (e.g., optionally substituted alkylene), or an optionally substituted heteroalkyl (e.g., optionally substituted heteroalkylene). Optional substitutions can include one or more of the following on a backbone (e.g., an arylene or alkylene backbone): hydroxyl, optionally substituted alkyl, haloalkyl, hydroxyalkyl, optionally substituted alkoxy (e.g., methoxy, ethoxy, benzyloxy, etc.), optionally substituted cycloalkyl, optionally substituted cycloalkoxy, optionally substituted aryl, optionally substituted aryloxy, halo, carboxyl, azido, cyano, nitro, amino, aminoalkyl, or carboxyaldehyde, as well as any optional substituents described herein for alkyl and aryl.

Exemplary linkers can include an optionally substituted phenylene, optionally substituted dithieno[3,2-b; 2',3'-d]-thiophene, optionally substituted 2,2'-bipyridyl, optionally substituted terphenylene (in ortho, meta, or para forms), and an optionally substituted biphenylene.

Further non-limiting, exemplary ligands include 3,3',5,5'-azobenzenetetracarboxylate ($ADB^{4-}$); 5,5'-(9,10-anthracenediyl)di-isophthalate ($ADIP^{4-}$); adamantane-1,3,5,7-tetracarboxylate ($ATC^{4-}$); 4,4',4''-(benzene-1,3,5-triyl-tris(benzene-4,1-diyl))tribenzoate ($BBC^{3-}$ or $TCBB^{3-}$); 1,4-benzenedicarboxylate ($BDC^{2-}$); $BDC-(X)^{2-}$ or $BDC-(X)_2^{2-}$, where each X is, independently, alkyl, halo, hydroxyl, nitro, amino, carboxyl, alkoxy, cycloalkoxy, aryloxy, benzyloxy (e.g., 2-amino-1,4-benzenedicarboxylate ($BDC-NH_2^{2-}$) or 2,5-diamino-1,4-benzenedicarboxylate ($BDC-(NH_2)_2^{2-}$); 5,5',5''-(((benzene-1,3,5-triyltris(benzene-4,1-diyl))tris(ethyne-2,1-diyl))-tris(benzene-4,1-diyl))tris(ethyne-2,1-diyl)) triisophthalate]($BHEHPI^{6-}$); 5,5',5''-(benzene-1,3,5-triyl-tris(buta-1,3-diyne-4,1-diyl))triisophthalate ($BHEI^{6-}$); 5,5',5''-((benzene-1,3,5-triyl-tris(ethyne-2,1-diyl))tris(benzene-4,1-diyl))tris(buta-1,3-diyne-4,1-diyl))triisophthalate (BNE-$TPI^{6-}$); 4,4'-biphenyl dicarboxylate ($BPDC^{2-}$); 2,2'-bipyridine-5,5'-dicarboxylate ($BPYDC^{2-}$); 4,4',4''-benzene-1,3,5-triyl-tribenzoate ($BTB^{3-}$); 1,3,5-benzenetricarboxylate or 1,2,4-benzenetricarboxylate ($BTC^{3-}$); 4,4',4''-(benzene-1,3, 5-triyl-tris(ethyne-2,1-diyl))tribenzoate ($BTE^{3-}$); 5,5',5''-(benzene-1,3,5-triyl-tris(ethyne-2,1-diyl))triisophthalate ($BTEI^{6-}$); 5',5'''',5''''''-(benzene-1,3,5-triyl-tris(ethyne-2,1-diyl))tris(([1,1':3',1''-terphenyl]-4,4''-dicarboxylate)) (BTE-$TCA^{3-}$); 4,4',4''-(benzene-1,3,5-triyl)tris(pyrazol-1-ide) (B-$TP^{6-}$); 5,5',5''-(benzene-1,3,5-triyl-tris(benzene-4,1-diyl)) triisophthalate ($BTPI^{6-}$); 5,5',5''-(benzene-1,3,5-triyl-tris(biphenyl-4,4'-diyl))triisophthalate ($BTTI^{6-}$); 3,3'-difluoro-biphenyl-4,4'-dicarboxylate ($DFBPDC^{2-}$); 2,5-dioxido-1,4-benzenedicarboxylate ($DOBDC^{4-}$); 4,6-dioxido-1,3-benzenedicarboxylate (m-$DOBDC^{4-}$); 4,4'-dioxidobiphenyl-3, 3'-dicarboxylate ($DOBPDC^{4-}$); dioxidoterephthalate (D-$OT^{2-}$); 4,4'-([2,2'-bipyridine]-5,5'-diyl)dibenzoate (DPBPy-$DC^{2-}$); 3-fluoro-biphenyl-4,4'-dicarboxylate ($FBPDC^{2-}$); 2-fluoro-4-(1H-tetrazol-5-yl)benzoate ($FTZB^{2-}$); 3-fluoro-4'-(1H-tetrazol-5-yl)biphenyl-4-carboxylate ($FTZBP^{2-}$); imidazoledicarboxylate ($HImDC^{3-}$); 1,4-naphthalenedicarboxylate ($NDC^{2-}$); 5,5',5''-((benzene-1,3,5-triyl-tris(benzene-4,1-diyl))tris(ethyne-2,1-diyl))triisophthalate (PT-$EI^{6-}$); 3,5-pyridinedicarboxylate or 2,5-pyridinedicarboxylate ($PyDC^{2-}$); 4,4',4''(1,3,5-triazine-2,4,6-triyl)tribenzoate ($TATB^{3-}$); 2,4,6-trihydroxy-1,3,5-benzenetrisulfonate (TH-$BTS^{3-}$); tris(4-(1H-imidazol-1-yl)phenyl)amine ($TIPA^{3-}$); 5,5',5''-((benzene-1,3,5-tricarbonyl) tris(azanediyl))triisophthalate ($TPBTM^{6-}$); 5,5',5''-(((benzene-1,3,5-triyl-tris (ethyne-2,1-diyl)) tris(benzene-4,1-diyl))tris(ethyne-2,1-diyl))triisophthalate ($TTEI^{6-}$); and 4-(1H-tetrazol-5-yl) benzoate ($TZB^{2-}$); each of which may optionally include one or more counterions (e.g., one or more counteranions or countercations), as well as a cation thereof, an anion thereof, a protonated form thereof, a salt thereof, or an ester thereof.

Exemplary reagents to install a ligand include, e.g., oxalic acid; fumaric acid; adamantanetetracarboxylic acid ($H_4ATC$); adamantanetetrabenzoic acid ($H_4ATB$); 9,10-anthracenedicarboxylic acid ($H_4ADB$); acetylene dicarboxylic acid ($H_2ADC$); 1,3,5-tris(4'-carboxy[1,1'-biphenyl]-4-yl) benzene ($H_3BBC$); terephthalic acid and optionally substituted forms thereof (e.g., $H_2BDC$ or $H_2BDC-(X)$ or $H_2BDC-(X)_2$, in which X can be optionally substituted alkyl, halo, hydroxyl, nitro, amino, carboxyl, optionally substituted alkoxy, optionally substituted cycloalkoxy, or optionally substituted aryloxy); biphenyl-3,4',5-tricarboxylic acid ($H_3BHTC$); biphenyl-3,3',5,5'-tetracarboxylic acid ($H_4BPTC$); 1,3,5-tris(4-carboxyphenyl)benzene ($H_3BTB$); trimesic acid ($H_3BTC$); 1,3,5-triscarboxyphenylethynylbenzene ($H_3BTE$); 2,5-dihydroxyterephthalic acid ($H_4DOBDC$); 2,5-dihydroxy-1,4-benzenedicarboxylic acid ($H_4$DOT); glycine-alanine (Gly-Ala); imidazole (Im); methylimidazole (mIm); 3,3',5,5'-tetracarboxydiphenylmethane ($H_4$MDIP); 2-methylimidazole (HMIM); methane tetrabenzoic acid ($H_4$MTB); 2,6-naphthalenedicarboxylic acid (2,6-$H_2$NDC); 5'-(4-carboxyphenyl)-[1,1':3',1"-terphenyl]-3,3", 5,5"-tetracarboxylic acid ($H_5$PTPCA); 4,4',4"-s-triazine-2,4,6-triyl-tribenzoic acid ($H_3$TATB); 1,2,4,5-tetrakis(4-carboxyphenyl)benzene ($H_4$TCPB); [1,1':4',1"]terphenyl-3,3',5,5'-tetracarboxylic acid ($H_4$TPTC), as well as optionally substituted forms of any of these (e.g., optional substitutions as provided for alkyl or aryl herein).

The composition and construct can have any useful property. In one non-limiting instance, the composition has an emission signal (e.g., an emission peak signal) within a range from deep red to near-infrared wavelengths (e.g., of from about 600 nm to about 1500 nm, including from about 610 nm to about 1450 nm or from about 610 nm to about 1350 nm).

Particles and Constructs

The MOF compositions herein can be provided in any useful form (e.g., a particle or a crystal, such as a nanocrystal). In one non-limiting embodiment, the composition is provided as a particle (e.g., a nanoparticle, a microparticle, a nanorod, a nanocube, etc.). Exemplary particles include coated particles, core-shell particles, lipid-coated particles, etc. The MOF particle can be porous, thus can be loaded with one or more cargos (e.g., any described herein). In some instance, the MOF composition or MOF particle itself can be used as a label or a cargo for another construct.

The MOF composition can be employed as a core for other constructs. In one embodiment, the construct includes a MOF composition surrounded by one or more outer layers. Optionally, the MOF composition is provided as a particle (e.g., a core particle). In another embodiment, the construct includes a plurality of MOF particles (e.g., a multicore particle including a plurality of MOF core particles). The particles in turn can be surrounded by one or more outer layers (e.g., as in a liposome or embedded in a matrix).

The outer layer can include any useful material. In one instance, the outer layer can be a matrix within which a MOF composition can be embedded. In another instance, the outer layer can be a shielding agent which protects the MOF composition from possible degradation in vivo. In yet another instance, the outer layer includes a plurality of layers, and each layer can be the same or different. For example, a construct can include a MOF core, a first outer layer that is disposed on a surface of a core (e.g., a first outer layer including a matrix, such as an inorganic silica matrix), and a second outer layer that is disposed on a surface of the first outer layer (e.g., a second outer layer including a lipid layer, including a lipid monolayer, a lipid bilayer, a lipid multilayer, etc.).

Exemplary materials for the outer layer include a polymer (e.g., a brush polymer), an organic matrix (e.g., a polymeric matrix, lignin, a sugar, a polysaccharide, a monosaccharide, etc.), an inorganic matrix (e.g., silica, alumina, etc.), graphite, graphene, a lipid, a triglyceride, or a lipid layer (e.g., a lipid monolayer, a lipid bilayer, a lipid multilayer), a shielding layer (e.g., including a polymer or a lipid), a colloid, in any useful form (e.g., a shell, such as a porous shell or a combination of an inner shell and an outer shell, wherein the material for each of the inner and outer shells can be the same or different).

The outer layer can further include any other useful component, such as a biocompatible polymer (e.g., poly(ethylene glycol), a targeting ligand (e.g., any herein), a cluster of differentiation (e.g., CD 47), a lipid (e.g., a lipid layer, a PEGylated lipid, or any other described herein), a lipid component (e.g., cholesterol), etc. Exemplary lipids and lipid components include 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-oleoyl-2-[12-[(7-nitro-2-1,3-benzoxadiazol-4-yl)amino]lauroyl]-sn-glycero-3-phosphocholine (18:1-12:0 NBD PC), 1-palmitoyl-2-{12-[(7-nitro-2-1,3-benzoxadiazol-4-yl)amino]lauroyl}-sn-glycero-3-phosphocholine (16:0-12:0 NBD PC), cholesterol, and mixtures/combinations thereof, as well as PEGylated forms of any of these (e.g., PEGs having a variety of lengths and molecular weights and include, but are not limited to, PEG 200, PEG 1000, PEG 1500, PEG 4600, PEG 10,000, PEG-peptide conjugates or combinations thereof).

The MOF composition can be provided as any useful construct. Exemplary constructs include particles, lipid-coated particles, emulsions (e.g., including reverse emulsions), micelles, liposomes (e.g., a nanosome), composite particles, polymerosomes, core-shell particles (e.g., in which the shell can be any useful material, such as silica, etc.), multicore-shell particles, thin films, membranes, beads, composites (e.g., MOF in any form, such as particle form, within a matrix), etc.

Constructs can be formed in any useful manner. In one instance, the MOF composition is processed to form a particle. Exemplary processes include hydrosolvothermal synthesis, microemulsion synthesis, room temperature synthesis, electrochemical synthesis, microwave-assisted hydro/solvothermal synthesis, and sonochemical synthesis (e.g., using ultrasound).

Constructs can be characterized by any useful dimension. Constructs can range, e.g., from around 1 nm to around 500 nm in size, including all integers and ranges there between. The size is measured as the longest axis of the construct. In various embodiments, the constructs are from around 5 nm to around 500 nm and from around 10 nm to around 100 nm in size.

Constructs may be characterized by an effective average particle size, in which at least 50% of the particles therein are of a specified size. Accordingly, "effective average particle size of less than about 2,000 nm in diameter" means that at least 50% of the particles therein are less than about 2,000 nm in diameter. In certain embodiments, particles have an effective average particle size of less than about 2,000 nm (i.e., 2 microns) (e.g., less than about 1,900 nm, 1,800 nm, 1,700 nm, 1,600 nm, 1,500 nm, 1,400 nm, 1,300 nm, 1,200 nm, 1,100 nm, 1,000 nm, 900 nm, 800 nm, 700 nm, 600 nm, 500 nm, 400 nm, 300 nm, 250 nm, 200 nm, 150 nm, 100 nm, 75 nm, or 50 nm, as measured by light-scattering methods, microscopy, or other appropriate methods. In certain aspects, where administration via intravenous, intramuscular, intraperitoneal, retro-orbital and subcutaneous injection routes produces long residence times (on the order of at least 12 hours to 2 weeks or more) and greater biodistribution and/or bioavailability, the constructs are monodisperse and generally no greater than about 50 nm in average diameter (e.g., less than about 30 nm in average diameter).

Particles, or a portion thereof, may optionally have a porous structure. The pores can be from around 0.5 nm to about 25 nm in diameter, often about 1 to around 20 nm in diameter, including all integers and ranges there between. In one embodiment, the pores are from around 1 to around 10 nm in diameter. In one embodiment, around 90% of the pores are from around 1 to around 20 nm in diameter. In another embodiment, around 95% of the pores are around 1 to around 20 nm in diameter.

Constructs may optionally be functionalized with a targeting ligand configured to target a certain cell type or organ. Such targeting ligands generally bind to a moiety on the surface of a cell to be targeted so that the construct may selectively bind to the surface of the targeted cell and deposit their contents into the cell. Exemplary targeting ligands include a targeting peptide, a receptor binding peptide, a polypeptide including an antibody or antibody fragment (including monoclonal and/or polyclonal antibodies, such as IgG), an affibody, an aptamer, a carbohydrate, a cluster of differentiation (CD) protein, or a self-associated molecular pattern (SAMP) (e.g., as described in Lambris J D et al., *Nat. Rev. Microbial.* 2008; 6(2):132; and Poon I K H, *Cell Death Differ.* 2010; 17:381-97, each of which is incorporated herein by reference in its entirety). Exemplary CD proteins include CD47 (OMIM Entry No. 601028, a marker of self that allows RBC to avoid phagocytosis), CD59 (OMIM Entry No. 107271, a marker that prevents lysis by complement), C1 inhibitor (C1INH, OMIM Entry No. 606860, a marker that suppresses activation of the host's complement system), CD200 (OMIM Entry No. 155970, an immunosuppressive factor), CD55 (OMIM Entry No. 125240, a marker that inhibits the complement cascade), CD46 (OMIM Entry No. 120920, a marker that inhibits the complement cascade), and CD31 (OMIM Entry No. 173445, an adhesion regulator and a negative regulator of platelet-collagen interactions). Each recited OMIM Entry is incorporated herein by reference in its entirety.

Optionally, the construct can include a cell penetration peptide, a fusogenic peptide, a peptide zip code, or an endosomolytic peptide (e.g., disposed on an external surface of the construct). The cell penetration peptide can aid in translocation across a lipid bilayer, such as a cellular membrane or endosome lipid bilayer.

Cargos

The MOF compositions and constructs herein can include any useful cargo. Cargos can be loaded into the MOF composition or other portions of the construct (e.g., the outer layer, including the matrix, the shell, etc.).

Exemplary cargos include a nucleic acid sequence, including ribonucleic acid (RNA), deoxyribonucleic acid (DNA, including double stranded or linear DNA), a CRISPR component or a nucleic acid sequence encoding a CRISPR component, messenger RNA (mRNA), small interfering RNA (siRNA), small hairpin RNA (shRNA), microRNA, DNA, complementary DNA (cDNA), minicircle DNA (mcDNA), naked DNA, plasmid DNA (especially CRISPR ds plasmid DNA which is optionally modified to express RNA and/or a protein such as a reporter, e.g., green fluorescent protein, especially siRNA which causes apoptosis of cancer cells), as well as supercoiled and/or packaged (e.g., with histones) forms of any of these, which may be optionally modified with a nuclear localization sequence. Yet other exemplary nucleic acids or polynucleotides include, but are not limited to, threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids, chimeras, or other modified forms thereof. Polynucleotides can have any useful two-dimensional or three-dimensional structure or motif, such as regions including one or more duplex, triplex, quadruplex, hairpin, and/or pseudoknot structures or motifs.

Another exemplary cargo includes a CRISPR component (e.g., a guiding component and/or a nuclease, as well as chimeras, fusions, or modified forms thereof). In general, the guiding component includes a nucleic acid sequence (e.g., a single polynucleotide) that includes at least two portions: (1) a targeting portion, which is a nucleic acid sequence that imparts specific targeting to the target genomic locus (e.g., a guide RNA or gRNA); and an interacting portion, which is another nucleic acid sequence that binds to a nuclease (e.g., a Cas endonuclease). The guiding component can include any useful sequence, e.g., a tracrRNA sequence, a consensus sequence derived from known tracrRNA sequences, a modified tracrRNA sequence, an entirely synthetic sequence known to bind a Cas nuclease or determined to competitively bind a Cas nuclease when compared to a known tracrRNA sequence, a crRNA sequence, a consensus sequence derived from known crRNA sequences, a modified crRNA sequence, an entirely synthetic sequence known to bind a Cas nuclease or determined to competitively bind a Cas nuclease when compared to a known crRNA sequence, a 'protospacer adjacent motif' (PAM), a PAM-presenting oligonucleotide (PAMmer), as well as any useful transcriptional repressor domains transcriptional activation domains transcriptional effectors, activators, or repressors.

The nuclease generally binds a targeting nucleic acid sequence, in which the nuclease CRISPR component can either be an enzyme, or a nucleic acid sequence that encodes for that enzyme. The nuclease can include a mutated CRISPR enzyme (e.g., which lacks the ability to cleave one or both strands of a target polynucleotide containing a target sequence).

Yet other exemplary cargos include an acidic, basic, and hydrophobic drug (e.g., antiviral agents, antibiotic agents, etc.); a protein (e.g., antibodies, carbohydrates, etc.); a nucleic acid (e.g., DNA, RNA, siRNA, mcDNA vectors, e.g., that encode shRNA, cDNA, naked DNA, and plasmid DNA, as well as chimeras, single-stranded forms, duplex forms, and multiplex forms thereof); a protein (e.g., an enzyme, an initiation factor, or fragments thereof); a diagnostic/contrast agent, like quantum dots, iron oxide nanoparticles, gadolinium, and indium-111; a small molecule, such as a small molecule bioactive agent; a drug, a pro-drug, a vitamin, an antibody, a hormone, a growth factor, a cytokine, a steroid, an anticancer agent, a fungicide, an antimicrobial, an antibiotic, an antiviral agent, etc.; a morphogen; a toxin, e.g., a protein toxin, such as ricin toxin A-chain or diphtheria toxin A-chain; a peptide, e.g., an antimicrobial peptide; an antigen; an antibody; a detection agent (e.g., a particle, such as a conductive particle, a microparticle, a nanoparticle, a quantum dot, a latex bead, a colloidal particle, a magnetic particle, a fluorescent particle, etc.; a dye, such as a fluorescent dye, a luminescent dye, a chemiluminescent dye, a colorimetric dye, a radioactive agent, an electroactive detection agent, etc.); a label (e.g., a quantum dot, a nanoparticle, a microparticle, a barcode, a fluorescent label, a colorimetric label, a radio label (e.g., an RF label or barcode), avidin, biotin, a tag, a dye, a marker, an electroactive label, an electrocatalytic label, and/or an enzyme that can optionally include one or more linking agents and/or one or more dyes); a capture agent (e.g., such as a protein that binds to or detects one or more markers (e.g., an antibody or an enzyme), a globulin protein (e.g., bovine serum albumin), a nanoparticle, a microparticle, a sandwich assay reagent, a catalyst (e.g., that reacts with one or more markers), and/or an enzyme (e.g., that reacts with one or more markers, such as any described herein)); as well as combinations thereof.

Formulations

The present invention also relates to MOF compositions or constructs provided in any useful formulation. Exemplary formulations can include any useful pharmaceutically acceptable salt (e.g., any described herein) and/or pharmaceutically acceptable excipient (e.g., any described herein).

The present compositions and constructs can be formulated in any useful manner. For instance, the formulation can be optimized for subcutaneous (SC), intranasal (IN), aerosol, intravenous (IV), intramuscular (IM), intraperitoneal (IP), oral, topical, transdermal, or retro-orbital delivery. Any useful dosages can be employed within the formulations. Formulations may take the form of liquid, solid, semi-solid, or lyophilized powder forms, such as, for example, solutions (e.g., a sterile physiological salt solution, aqueous saline, aqueous dextrose, glycerol, or ethanol), suspensions, emulsions, sustained-release formulations, tablets, capsules, powders, suppositories, creams, ointments, lotions, aerosols, patches, dehydrated forms (e.g., suitable for hydration in water or saline), or the like, preferably in unit dosage forms suitable for simple administration of precise dosages.

Methods Thereof

The MOF compositions and constructs herein can be useful for any useful imaging method, delivery method, targeting method, treatment method, or diagnostic method. In addition, the present invention also relates to methods of making any MOF composition or construct described herein.

In one non-limiting instance, methods of treating (e.g., a cell or a subject) can include exposing the cell (e.g., within a subject) or the subject to a MOF composition or construct or formulation herein. The composition or construct can be provided in any useful form (e.g., as a particle, salt, anhydrate, solvate, etc.). In another non-limiting instance, methods of delivering a cargo can include exposing the cell (e.g., within a subject) or the subject to a MOF composition or construct or formulation herein, in which the composition or construct includes a cargo and can optionally include a targeting ligand. In yet another non-limiting instance, method of treating a disease (e.g., in a subject) can include exposing a cell or a subject to a composition or construct or formulation herein. In some instances, the composition or construct or formulation further includes one or more cargos in an amount sufficient to treat the disease.

Diagnostic methods include those useful for providing the composition or construct to a cell or a subject and then detecting the presence or absence of that composition or construct. The providing step can include any useful way of delivering the composition or construct (e.g., any particle, construct, etc., described herein), and the detecting step can include measuring a detectable signal of the particle or construct.

Other exemplary methods can include those for forming a composition or a construct. In one instance, the method includes providing a mixture, which includes a metal ion source and a ligand source; and reacting the mixture to provide a MOF composition (e.g., any herein). The method can further include a modulating agent (e.g., a formamide, such as N,N-diethylformamide (DEF) or N,N-dimethylformamide (DMF); an acid (e.g., nitric acid, formic acid, oxalic acid, acetic acid, trifluoroacetic acid, dodecanoic acid, a monocarboxylic acid, hydrochloric acid, sulfuric acid, etc.); water, etc.). In other embodiments, the reacting step includes any useful synthetic process (e.g., exposure to microwaves or ultrasound). To provide an anhydrate, solvent can be removed in any useful manner (e.g., by heating, thereby providing a coordinatively unsaturated metal center).

Cargo can be loaded into the composition or construct in any useful manner and at any point during the synthetic process. In one instance, the MOF composition is loaded with one or more cargos (e.g., by soaking the MOF composition within a solution containing the cargo(s)), and then one or more outer layers are directly or indirectly deposited on a surface of the composition, thereby providing a loaded construct. In another instance, the one or more outer layers are first deposited upon the MOF composition, and then the cargo is loaded. In further instance, a second outer layer is deposited (e.g., in which the second outer layer includes a lipid or a polymer). In any of these methods, loading can be achieved by introducing the cargo during MOF or shell synthesis.

EXAMPLES

Example 1: A Multifunctional, Tunable MOF Materials Platform for Bio-Imaging Applications Herein we describe a multifunctional metal-organic framework (MOF) materials platform that displays both porosity and tunable emission properties as a function of the metal identity (e.g., Eu, Nd, and tuned compositions of Nd/Yb). Their emission collectively spans the deep red to near-infrared (NIR) spectral region (e.g., about 614-1350 nm), which is highly relevant for in vivo bio-imaging. These new materials meet important prerequisites as relevant to biological processes: they are minimally toxic to living cells, and retain structural integrity in water and phosphate buffered saline.

In order to assess their viability as optical bio-imaging agents, we successfully synthesized the nanoscale Eu analog, as a proof-of-concept system in this series. In vitro studies show that it is cell-permeable in individual RAW 264.7 mouse macrophage and HeLa human cervical cancer tissue culture cells. The efficient discrimination between the Eu emission and cell autofluorescence was achieved with hyperspectral confocal fluorescence microscopy, used here for the first time to characterize MOF materials. Importantly, we documented the long-term conservation of the intrinsic emission in live cells of a fluorophore-based MOF to date (up to 48 hours). This finding, in conjunction with the materials' very low toxicity, validates the biocompatibility in these systems and qualifies them as promising for use in long-term tracking/biodistribution studies.

The quest to develop novel fluorescent probes for clinical diagnostics and to monitor biological processes in vivo has accelerated in recent years.[1] Deep tissue imaging requires probes whose excitation and emission wavelengths have low optical attenuation in and do not excite fluorescence from the tissue. It is generally accepted that deep-red to near-infrared (NIR) wavelengths (e.g., from about 650 nm to about 1450 nm) satisfy these requirements.[2] There is significant interest to develop novel materials whose excitation and emission wavelengths fall within the so-called second NIR window (e.g., from about 1000 nm to about 1350 nm),[3] where absorption by blood and water are minimal, and damage-free deep tissue penetration is possible.[4] The use of the second NIR window allows for enhanced resolution of vasculature in both normal limbs and tumors,[5] imaging of lymphatic systems,[6] and brain imaging of both tumors[6] and traumatic brain injury through the intact skull.[7]

Known NIR-emitting fluorophores include organic dyes,[6,8] quantum dots[9], and single wall carbon nanotubes.[10] Some of the main limitations associated with these systems include broad and/or weak emissions, and short lifetimes, which preclude their use in in vivo long-term tracking experiments.

Alternatively, probes based on lanthanide fluorescence offer significant advantages over the state-of-the-art materials to improve both the spectral and time-resolved signal discrimination from background autofluorescence, due to: (i) sharp and stable emissions; (ii) large effective Stokes shifts; and (iii) long-lived luminescent lifetimes.[11,12] Also, they are generally regarded as nontoxic and have been shown to only mildly render histological changes when used in high concentrations.[13] Importantly, the luminescence of the lanthanide ions can be dramatically enhanced when sensitized by an organic chromophore, via the antenna effect.[14,15]

In this context, hybrid organic-inorganic materials, such as metal-organic frameworks (MOFs)[16] can offer unique solutions to overcome the limitations of existing NIR emitting materials via: (i) rational material design strategies through predetermined metal and ligand selection; (ii) emission tunability; (iii) permanent porosity, which enables their use as advanced theranostic agents for imaging—cargo delivery tandem or sensing of reactive species.

The luminescent properties of MOFs have been investigated, primarily for sensing and light-emitting devices.[17-19] Some of us have previously reported on their potential use in devices that operate at elevated temperatures, such as white light-emitting diodes for solid-state lighting.[20,21] However, only a very limited number of studies have demonstrated their relevance as optical bio-imaging agents.[22] In fact, luminescence in the NIR has rarely been observed in MOFs,[23-28] as the emission of NIR ions ($Nd^{3+}$, $Yb^{3+}$, $Er^{3+}$) can be easily quenched due to a reduced energy gap between the ground state and the emitting state.[4]

Here, we judiciously targeted a novel materials platform based on a predetermined rare earth hexanuclear metal cluster, M=Eu, Nd, Yb, Y, Tb, as well as tuned compositions of Nd/Yb ($Nd_{0.67}/Yb_{0.33}$, $Nd_{0.46}/Yb_{0.54}$), coordinated by 2,5-dihydroxyterephthalic acid. It is important to note that one of the greatest challenges that preclude the rational synthesis of MOFs with built-in structural features is the lack of control over the coordination geometry of the metal ions. Recently, Eddaoudi et al. pioneered the development of polynuclear rare earth-based molecular building blocks and detailed prerequisites for the systematic access to these molecular building blocks in situ.[29-32]

The structure-function correlation in the materials reported here was investigated via in-depth characterization, including single crystal X-ray diffraction, powder X-ray synchrotron scattering and pair distribution function analyses, microscopy, thermal analyses, and photoluminescence measurements. Particular emphasis was placed on evaluating the relevance to bio-related applications by: (a) monitoring the stability under simulated physiological conditions, (b) evaluating the cytotoxicity to living cells, and (c) assessing the use as imaging agents via live cell imaging. Additional details follow.

Example 2: Experimental Details

All reactant materials were purchased from commercially available sources and used without further purification.

Synthesis of EuDOBDC, compound 1: The reaction mixture containing $EuCl_3 \cdot 6H_2O$ (0.0689 g, 0.087 mmol), 2,5-dihydroxyterephthalic acid (DOBDC, 0.0544 g, 0.087 mmol), 2-fluorobenzoic acid (2-FBA, 0.5760 g, 4.12 mmol), N,N'-dimethylformamide (DMF, 8 mL), $H_2O$ (2 mL), $HNO_3$ (0.6 mL, 3.5 M in DMF) was placed in a 20 mL scintillation vial and was heated to 115° C. for 60 h, at a rate of 1.5° C./minute and cooled to room temperature at a cooling rate of 1° C./minute.

Synthesis of NdDOBDC, compound 2: The reaction mixture containing $Nd(NO_3)_3 \cdot 6H_2O$ (0.0412 g, 0.0940 mmol), 2,5-dihydroxyterephthalic acid (DOBDC, 0.0272 g, 0.137 mmol), 2-fluorobenzoic acid (2-FBA, 0.2880 g, 2.06 mmol), N,N'-dimethylformamide (DMF, 4 mL), $H_2O$ (1 mL) was placed in a 20 mL scintillation vial and was heated to 115° C. for 60 h, at a rate of 1.5° C./minute and cooled to room temperature at a cooling rate of 1° C./minute.

Synthesis of YbDOBDC, compound 3: The reaction mixture containing $Yb(NO_3)_3 \cdot 5H_2O$ (0.0780 g, 0.174 mmol), 2,5-dihydroxyterephthalic acid (DOBDC, 0.0544 g, 0.275 mmol), 2-fluorobenzoic acid (2-FBA, 0.1948 g, 1.39 mmol), N,N'-dimethylformamide (DMF, 8.8 mL), $H_2O$ (2 mL), $HNO_3$ (0.4 mL, 3.5 M in DMF) was placed in a 20 mL scintillation vial and was heated to 115° C. for 60 h, at a rate of 1.5° C./minute and cooled to room temperature at a cooling rate of 1° C./minute.

Synthesis of YDOBDC, compound 4: The reaction mixture containing $Y(NO_3)_3 \cdot 6H_2O$ (0.1080 g, 0.311 mmol), 2,5-dihydroxyterephthalic acid (DOBDC, 0.0816 g, 0.412 mmol), 2-fluorobenzoic acid (2-FBA, 0.8640 g, 6.17 mmol), N,N'-dimethylformamide (DMF, 8 mL), $H_2O$ (2 mL), $HNO_3$ (0.6 mL, 3.5 M in DMF) was placed in a 20 mL scintillation vial and was heated to 115° C. for 60 h, at a rate of 1.5° C./minute and cooled to room temperature at a cooling rate of 1° C./minute.

Synthesis of TbDOBDC, compound 5: The reaction mixture containing $Tb(NO_3)_3 \cdot 5H_2O$ (0.1224 g, 0.281 mmol), 2,5-dihydroxyterephthalic acid (DOBDC, 0.0816 g, 0.412 mmol), 2-fluorobenzoic acid (2-FBA, 0.8640 g, 6.17 mmol), N,N'-dimethylformamide (DMF, 8 mL), $H_2O$ (2 mL), $HNO_3$ (0.6 mL, 3.5 M in DMF) was placed in a 20 mL scintillation vial and was heated to 115° C. for 60 h, at a rate of 1.5° C./minute and cooled to room temperature at a cooling rate of 1° C./minute.

Synthesis of $Nd_{0.67}Yb_{0.33}DOBDC$, compound 6: The reaction mixture containing $Nd(NO_3)_3 \cdot 6H_2O$ (0.0381 g, 0.087 mmol), $Yb(NO_3)_3 \cdot 5H_2O$ (0.0391 g, 0.087 mmol), 2,5-dihydroxyterephthalic acid (DOBDC, 0.0544 g, 0.275 mmol), 2-fluorobenzoic acid (2-FBA, 0.1948 g, 1.39 mmol), N,N'-dimethylformamide (DMF, 8.8 mL), $H_2O$ (2 mL), $HNO_3$ (0.4 mL, 3.5 M in DMF) was placed in a 20 mL scintillation vial and was heated to 115° C. for 60 h, at a rate of 1.5° C./minute and cooled to room temperature at a cooling rate of 1° C./minute.

Synthesis of $Nd_{0.46}Yb_{0.54}DOBDC$, compound 7: The reaction mixture containing $Nd(NO_3)_3 \cdot 6H_2O$ (0.0191 g, 0.0435 mmol), $Yb(NO_3)_3 \cdot 5H_2O$ (0.0588 g, 0.131 mmol), 2,5-dihydroxyterephthalic acid (DOBDC, 0.0544 g, 0.275 mmol), 2-fluorobenzoic acid (2-FBA, 0.1948 g, 1.39 mmol), N,N'-dimethylformamide (DMF, 8.8 mL), $H_2O$ (2 mL), $HNO_3$ (0.4 mL, 3.5 M) was placed in a 20 mL scintillation vial and was heated to 115° C. for 60 h, at a rate of 1.5° C./minute and cooled to room temperature at a cooling rate of 1° C./minute.

Synthesis of EuDOBDC-NP (nanoparticles), compound 1-NP: The reaction mixture containing $EuCl_3 \cdot 6H_2O$ (0.03445 g, 0.094 mmol), 2,5-dihydroxyterephthalic acid (DOBDC, 0.02720 g, 0.1375 mmol), 2-fluorobenzoic acid (2-FBA, 0.2880 g, 2.055 mmol), N,N'-dimethylformamide (DMF, 4 mL) was placed in a 10 mL microwave vial and was heated to 175° C. for 15 minutes. A CEM Discover SP microwave was used for this experiment.

X-ray single-crystal data collection and determination: The X-ray intensities were measured using a Bruker-D8 Venture dual-source diffractometer (Cu Kα, λ=1.5406 Å) and CMOS detector. Indexing and frame integration was performed using the APEX-III software suite.[12a] Absorption correction was performed using face-indexing (numerical method) also within the APEX-III software. The structures were solved using SHELXL-2014/7 and refined using SHELXTL XLMP version 2014/7.

Powder X-ray Diffraction (PXRD): Measurements were performed on a Siemens Kristalloflex D500 diffractometer, CuKα radiation (λ=1.54178 Å).

Variable temperature powder X-ray Diffraction (XRD): High temperature XRD experiments were performed using a Scintag PAD $X_1$ diffractometer (Thermo Electron Inc.; Waltham, Mass.) using (Cu Kα, λ=0.15418 nm), an incident-beam mirror optic, a Peltier-cooled Ge solid-state detector, and a Buehler hot-stage with Pt/Rh heating strip and surround heater. Temperature calibration was performed using thermal expansion behavior of Alumina. Samples were heated in a static air and scan parameters were 5-60° 2θ, 0.05° step, 3 s count-time.

Thermogravimetric Analyses-Differential Scanning calorimetry (TGA-DSC): Measurements were conducted on a SDTQ600 TA instrument, equipped with a mass-spectrometer gas analyzer MS-ThermoStar™ from Pfeiffer Vacuum. The samples were heated at 10° C./min to 800° C. under nitrogen flow.

High-energy Synchrotron Scattering and Pair Distribution Function (PDF) Analysis: X-ray scattering data suitable for diffraction and PDF analysis were collected at beamlines 11-ID-B at the Advanced Photon Source at Argonne National Laboratory.

For PDF analysis, high energy X-rays (11-ID-B, 58 keV, λ=0.2114 Å) were used, in combination with a large amorphous silicon-based area detector, to collect data to high values of momentum transfer, $Q_{max}$=22 Å$^{-1}$.[33,34] The two-dimensional images were reduced to one-dimensional scattering data within fit2d. The PDFs, G(r), were extracted within PDFgetX2, subtracting contributions from the background, Compton scattering, fluorescence, to the total scattering data as described previously. To separate the features in the PDF associated with the metal-coordination, differential PDFs (dPDFs) were calculated, subtracting the PDF measured for the bulk ligand from that of the MOF. The position and area of features of interest within the dPDF were quantified by fitting Gaussian functions within fityk.

For diffraction analysis, data were collected using a large amorphous silicon-based area detector placed a large distance (100 cm) from the sample to maximize angular resolution. The two-dimensional images were reduced to one-dimensional scattering data within fit2d.

Scanning Electron Microscopy (SEM)-Energy Dispersive Spectroscopy (EDS): SEM analyses were captured on a FEI NovaNano SEM 230, at various accelerating voltages between 1 and 20 kV. EDS analyses were collected on an EDAX Genesis Apex 2 with an Apollo SDD detector.

Transmission Electron Microscopy (TEM): TEM images were taken on JEOL 1200EX transmission electron microscope with a maximum acceleration voltage of 120 kV. Prior to TEM measurements, samples were dispersed in absolute ethanol and deposited on a carbon film coated copper grid.

Sample activation and gas adsorption measurements: Prior to measuring the gas adsorption isotherms, the samples were immersed in 15 mL of methanol for 3 days, with the solvent replenished every 24 hrs. Following this treatment, all samples were activated under vacuum on a Micromeritics ASAP 2020 surface area and porosity analyzer, at 120° C. for 16 hrs. Nitrogen gas adsorption isotherms were measured at 77 K using nitrogen of ultra-high purity (99.999%, obtained from Matheson Tri-Gas).

Photoluminescence (PL) measurements: The PL emission and excitation spectra of powder samples of compound 1 were collected using a Horiba Jobin-Yvon Fluorolog-3 double-grating/double-grating Fluorescence Spectrophotometer in front-face mode. The powder samples of the visible light-emitting MOFs were placed in 4-inch-long Pyrex NMR tubes for PLE and PL measurements. The NIR PL was collected from powder samples dispersed uniformly in a plastic Petri dish and placed under the objective.

Excitation spectra were collected by monitoring at the peak of the emission, and scanning over UV-visible wavelengths (320-550 nm). For the NIR PL measurements, powder samples of compounds 2, 6, and 7 were illuminated with an 808 nm diode laser using a long pass dichroic beam splitter as a reflector. The PL transmitted through the splitter was directed to an Acton 2500 spectrophotometer (0.5 m focal length, 300 g/mm grating) equipped with liquid nitrogen cooled InGaAs linear array detector. Both the excitation source and PL were focused through a common 0.65 NA objective.

Dynamic light scattering measurements (DLS): Hydrodynamic size was acquired on a Malvern Zetasizer Nano-ZS equipped with a He—Ne laser (633 nm) and non-invasive backscatter optics (NIBS). All samples for DLS measurements were suspended in various media (methanol, PBS, and DMEM+10% FBS) at 0.5 mg/mL. Measurements were acquired at 2° C. and the refractive index was set to that of Eu (0.625). DLS measurements for each sample were obtained in triplicate. The Z-average diameter was used for all reported hydrodynamic size measurements.

Cytotoxicity assessment: HeLa and RAW 264.7 cells (ATCC) were maintained in Dulbecco's Modified Eagle's Medium (DMEM) with 10% fetal bovine serum (FBS). For cytotoxicity assessment, 5,000 cells were plated per well in 100 μL in 96 well plates. Cells were allowed to adhere overnight. After cells had adhered, fresh media containing MOF samples at varied concentration (0-500 μg/mL) were prepared. The MOF samples were suspended in dimethyl sulfoxide (DMSO); DMSO can adversely affect cell viability, so the addition of DMSO was held to 5 μL per 1 mL sample. Cell exposure was performed by removing media on the adherent cells and replacing with freshly prepared media containing MOF samples. Cells were exposed to MOF samples for 24 or 48 hrs at standard cell culture conditions (37° C. and 5% $CO_2$). After exposure, cytotoxicity was assessed using CellTiter-Glo 2.0 Assay (Promega) with luminescence measured by a BioTek microplate reader. The cell viability was calculated as a percentage of mock (DMSO only) treated sample. Cytotoxicity measurements were performed in quadruplicate.

Hyperspectral confocal fluorescence microscopy (HCFM): Imaging of pristine EuDOBDC-NP was conducted with nanoparticles suspended in water, which were spread onto a glass slide and sealed with a coverslip then imaged as described below.

Cell incubation experiments: RAW 264.7 mouse macrophage and HeLa human cervical cancer tissue culture cells were seeded for 24 hrs on glass poly-L-lysine coated coverslips at a density of 150,000 cells/well in a 6-well tissue-culture treated plate. After 24 hrs, a 10 mg/mL nanoparticle solution in DMSO for 24 hrs were added to the cells to a final concentration of 20 µg/mL in the well. Coverslips were mounted onto glass slides using silicon spacers containing a pool of DMEM+10% FBS+1% Pen-Strep culture media and were immediately imaged. Samples were not kept under cover slip for more than 1 hour per sample.

Spectral images of live cells were obtained on a custom hyperspectral confocal fluorescence microscope (HCFM).[35] 488 nm laser excitation (Coherent, Inc.) was focused onto the cells using a 60× oil immersion objective (Nikon PlanApochromat, NA 1.4). Spectral data for each voxel of the image was dispersed using a prism spectrometer (500-800 nm) and collected with an electron-multiplied CCD camera (Andor Technologies, Inc.). During imaging, a combination of laser and stage scanning provided diffraction limited voxels with spatial resolution of 240 nm×240 nm×600 nm and an integration time of 240 µs/spectrum.

HCFM images were preprocessed and underlying component spectra were extracted using multivariate curve resolution (MCR) as described elsewhere.[36, 37] HCFM images of both the HeLa and RAW cells containing 20 µg/mL nanoparticles were compiled into a composite image set. Principal component analysis of the preprocessed data set indicated three underlying spectral factors were present. A three factor MCR model was developed, consisting of a flat baseline to describe detector offset and two fluorescence spectra: autofluorescence of the cells and the MOF nanoparticles. Concentration maps for each of the spectral components identified by MCR were predicted using classical least squares and represent the relative abundance and localization of each component within each image.

Example 3: Structural Characterization of Exemplary MOF Compositions

Figure 1A:
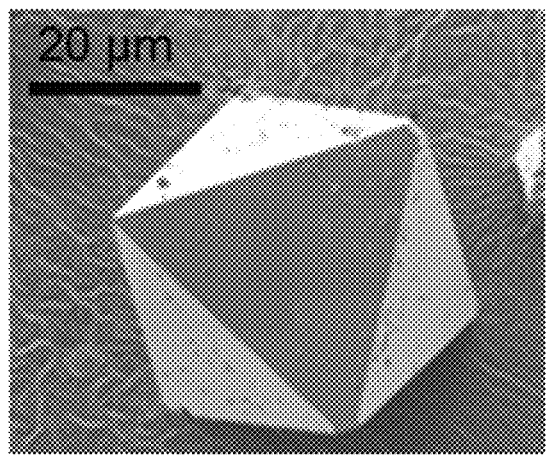
FIG. 1A-1D shows an exemplary MOF composition. Provided are a scanning electron microscopy (SEM) image of a single-crystal of compound 1 (FIG. 1A), a ball-and-stick depiction of a representative Eu hexanuclear cluster (FIG. 1B), a schematic view of the 3-periodic framework (FIG. 1C), and the octahedral cage (FIG. 1D). Hydrogen atoms and pore solvent molecules have been omitted for clarity; atom color scheme: M=light grey (Eu); C=medium grey, O=dark grey.
Figure 1B:
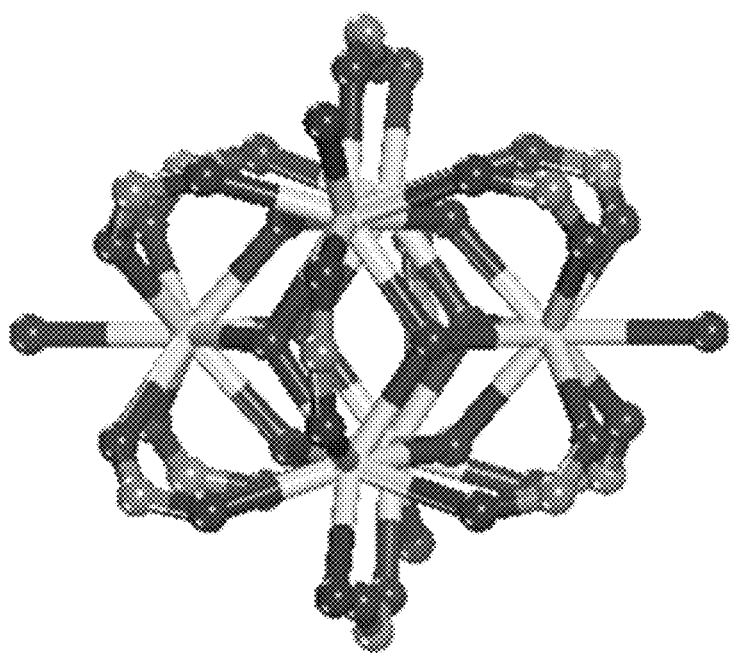
Figure 1C:
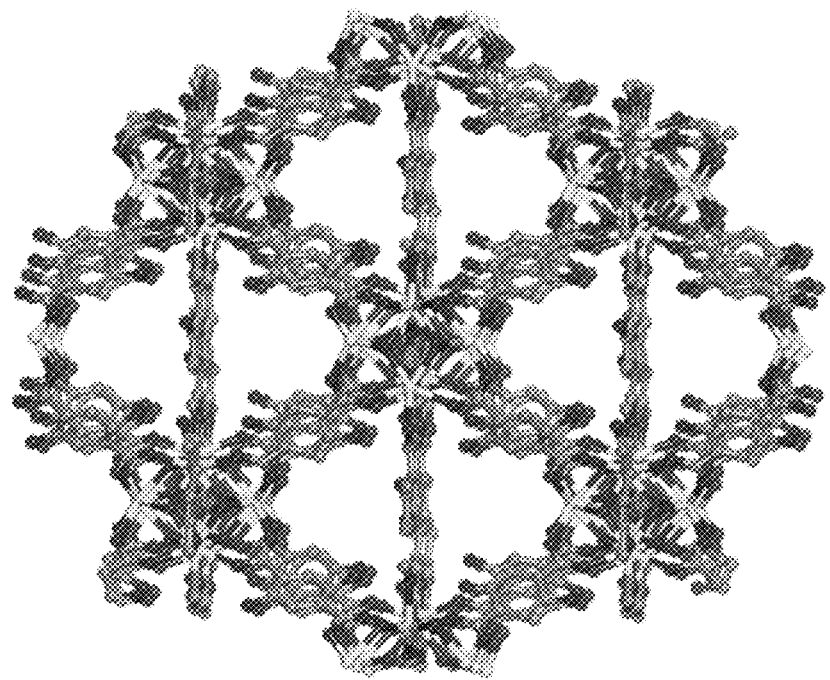
Figure 1D:
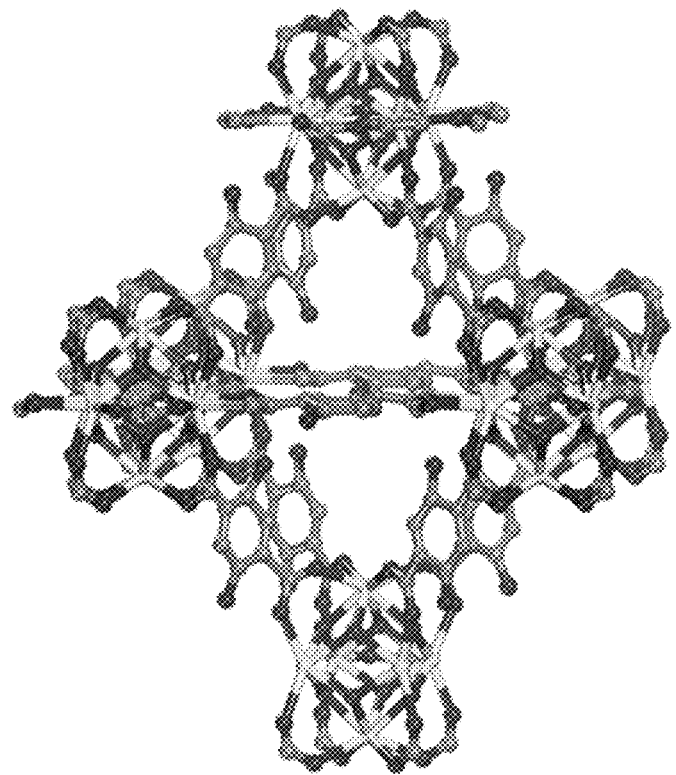

Initially, $EuCl_3.6H_2O$ was reacted with DOBDC and 2-FBA in a $DMF/H_2O$ system. This resulted in crystals with polyhedral morphology (FIG. 1A). To be noted, the addition of nitric acid was needed to improve the morphology of the crystalline phases reported herein, with the exception of Nd analog. Compound 1, EuDOBDC, was characterized and formulated by single crystal X-ray crystallography studies as $Eu_6(\mu_3\text{-}OH)_8(C_8H_4O_6)_5(C_8H_6O_6)_1(H_2O)_6 \cdot 24H_2O$. The material is defined by a three periodic framework with octahedral cages of ~10.4 Å diameter (FIG. 1C-1D). The structure is based on the pre-designed hydroxo-bridged cluster in which six metal atoms are coordinated by twelve DOBDC organic linkers, resulting in an overall 12-connected node (FIG. 1B). In the crystal structure of 1, the Eu metal ions adopt both 8- and 9-coordination geometries.

As compared to previous reports,[29,30] the metal cluster accessed here exhibits a unique ligand binding mode. Specifically, 10 out of the 12 dicarboxylate bridging linkers bind in an anticipated bis-bidentate way, while the remaining 2 ligands coordinate to the metal ions in a monodentate fashion. This distinct behavior is likely correlated with the presence of the hydroxyl groups in the close proximity of the carboxylates. The presence of the bridging disorder occurs in the a-b plane of the structure and serves as a true disorder of the DOBDC ligand where the ligand bonds in a bidentate fashion on one cluster, and bridges to the adjacent cluster to bond in a monodentate coordination. Each ligand residing in the a-b plane will bond in this manner with one side of the ligand as bidentate and the other side connecting as monodentate. This allows for two possible positions of the ligand between clusters, the same ligand lying side-by-side one another in the a-b plane, and only one of the two possible orientations is ever occupied at any given time. This slight alteration of the binding mode propagates a shift in the alignment of the clusters. As a result, there is a change in the symmetry from anticipated cubic crystal system to tetragonal.

The remaining coordination sites are occupied by a total of six water molecules per cluster. These water molecules can be removed by applying heat, in vacuum (120° C.), generating coordinatively unsaturated metal centers. Importantly, only a very limited set of MOFs are known to exhibit this desirable property, which is highly useful for a variety of applications that are pertinent to tuning guest-framework interactions.[38]

Further, additional analogs were successfully synthesized, including the Nd, Yb, Y, and TbDOBDC versions, as well two mixed metal systems, $Nd_{0.67}/Yb_{0.33}$, $Nd_{0.46}/Yb_{0.54}$ DOBDC.

Figure 3A:
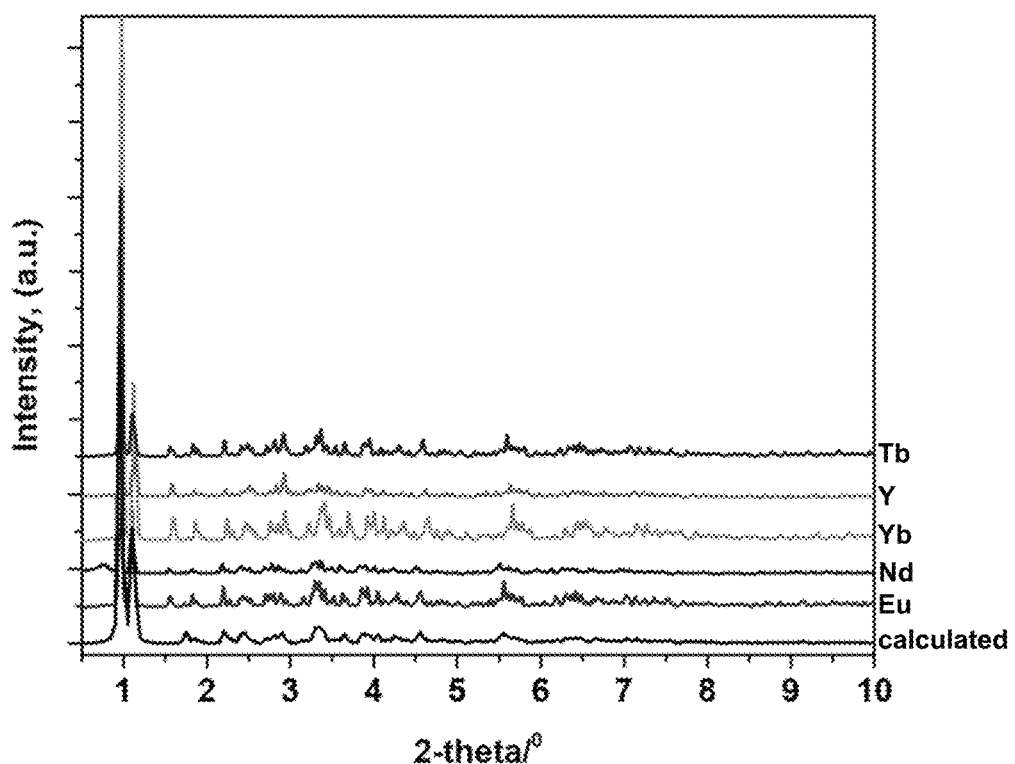
FIG. 3A-3B shows synchrotron X-ray diffraction data for compounds 1-5, as compared against a calculated pattern of compound 1, EuDOBDC (FIG. 3A) and high-energy synchrotron scattering and pair distribution function (PDF) analysis on compounds 1-5 (FIG. 3B).
Figure 3B:
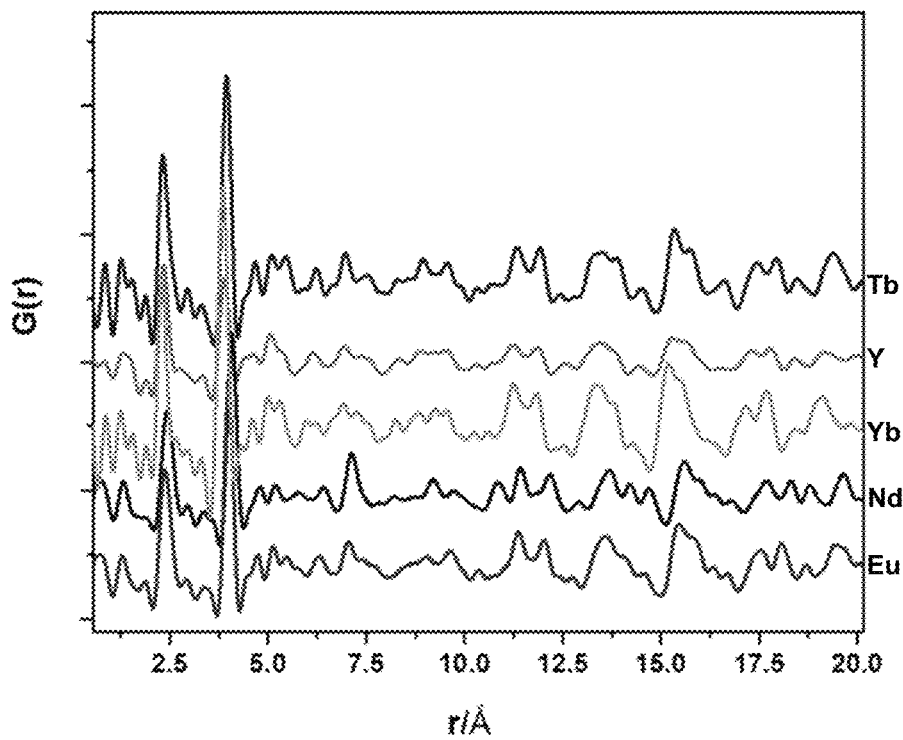
Figure 4A:
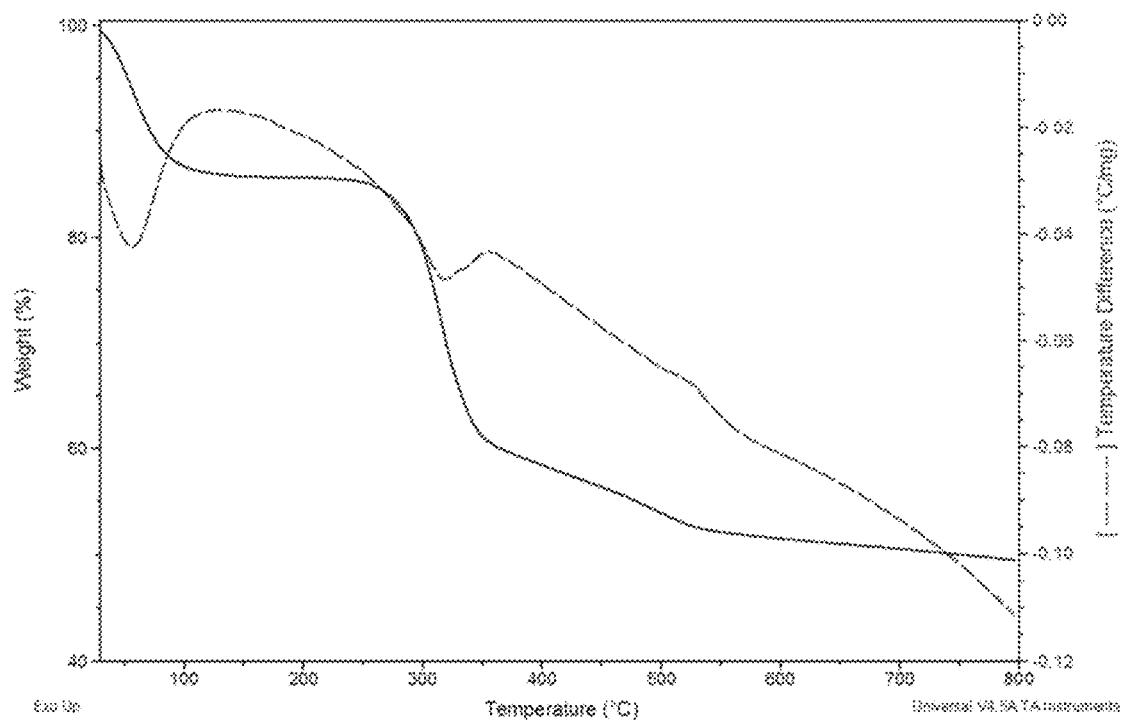
FIG. 4A-4E shows thermogravimetric analyses (TGA, solid line) and differential scanning calorimetry (DSC, dashed line) for compound 1, EuDOBC (FIG. 4A); compound 2, NdDOBDC (FIG. 4E); compound 3, YbDOBDC (FIG. 4E); compound 4, YDOBDC (FIG. 4E); and compound 5, TbDOBDC (FIG. 4E).
Figure 4B:
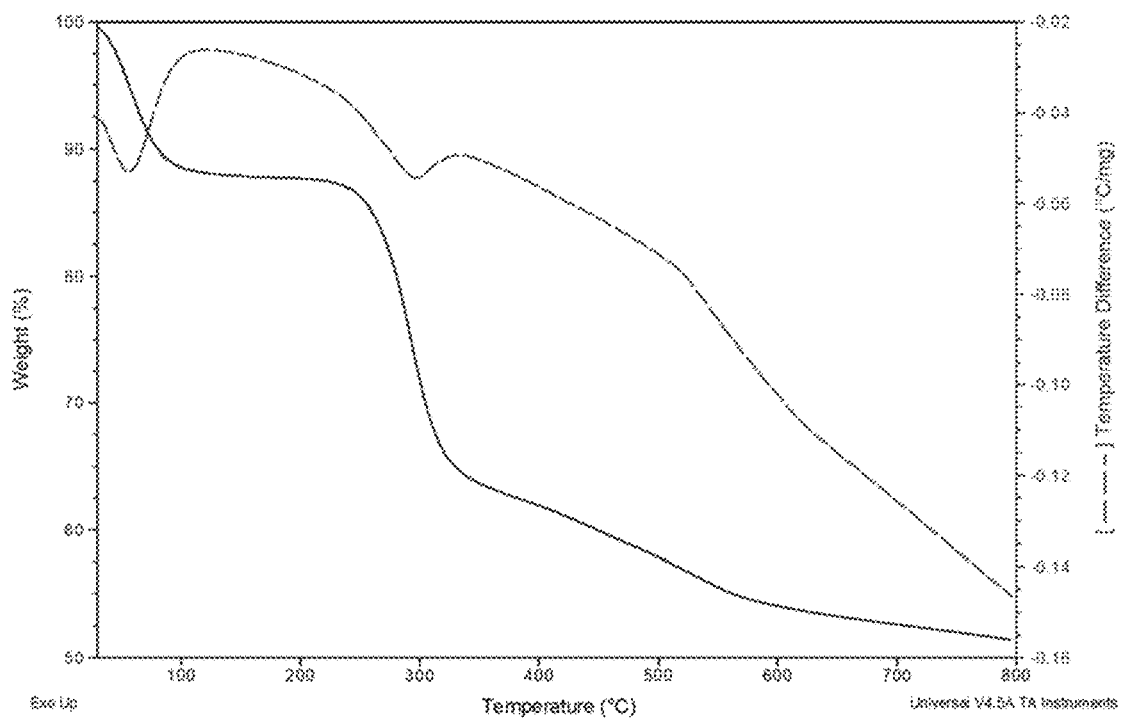
Figure 4C:
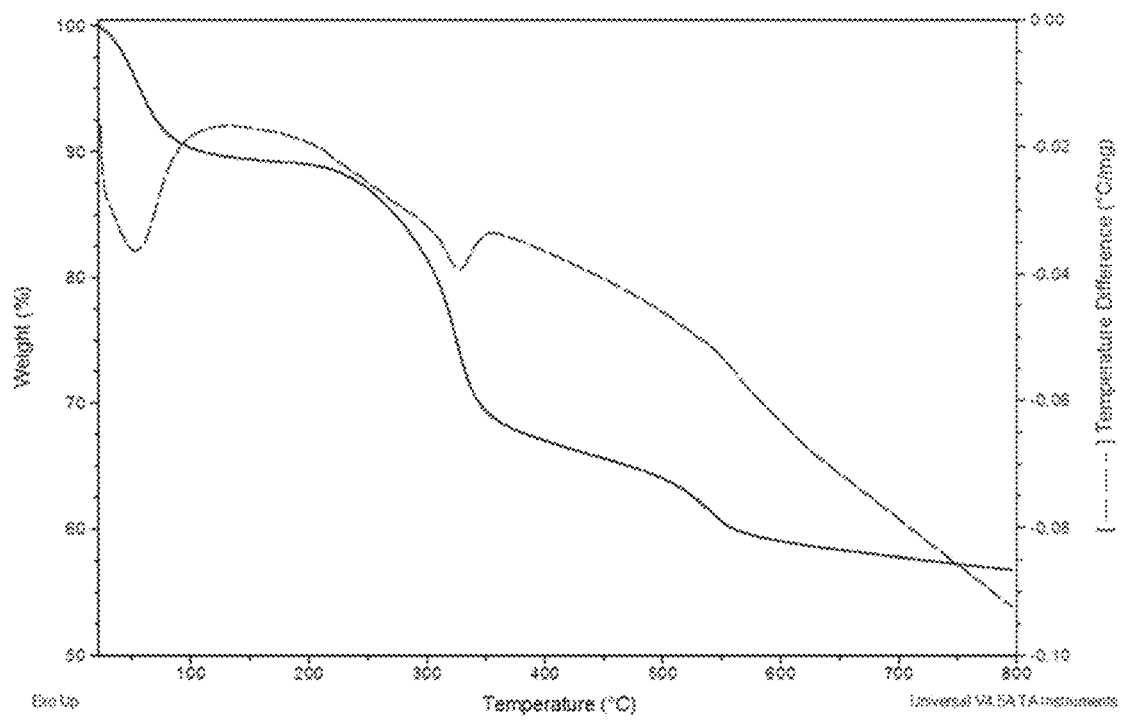
Figure 4D:
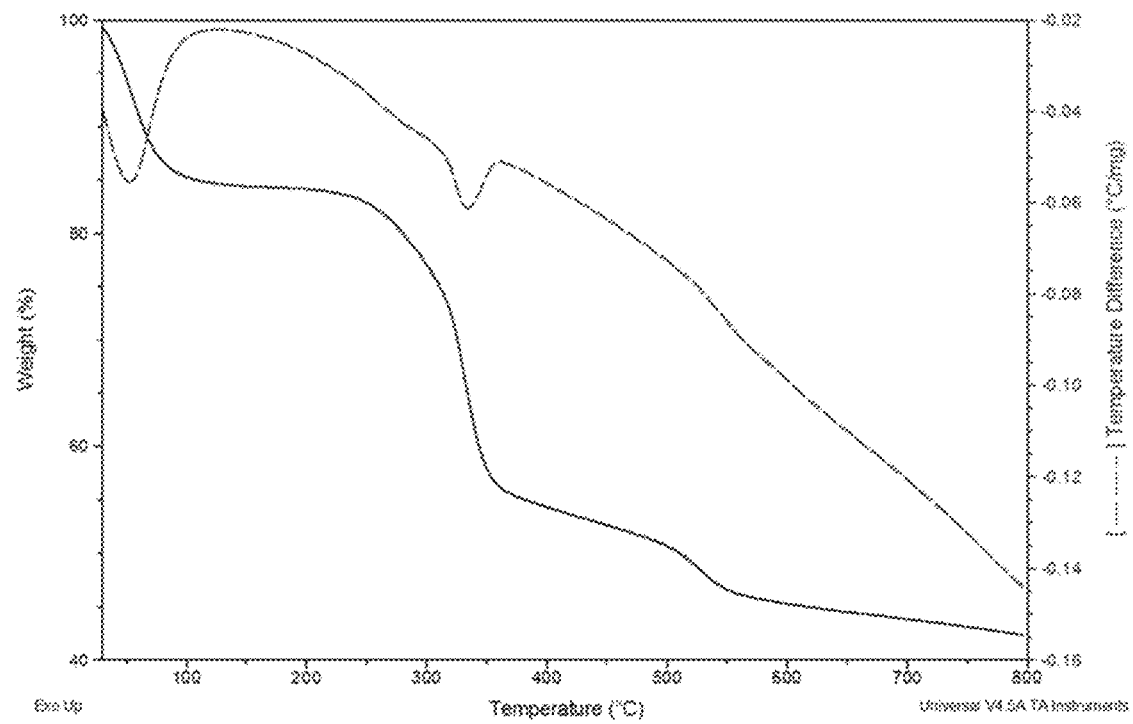
Figure 4E:
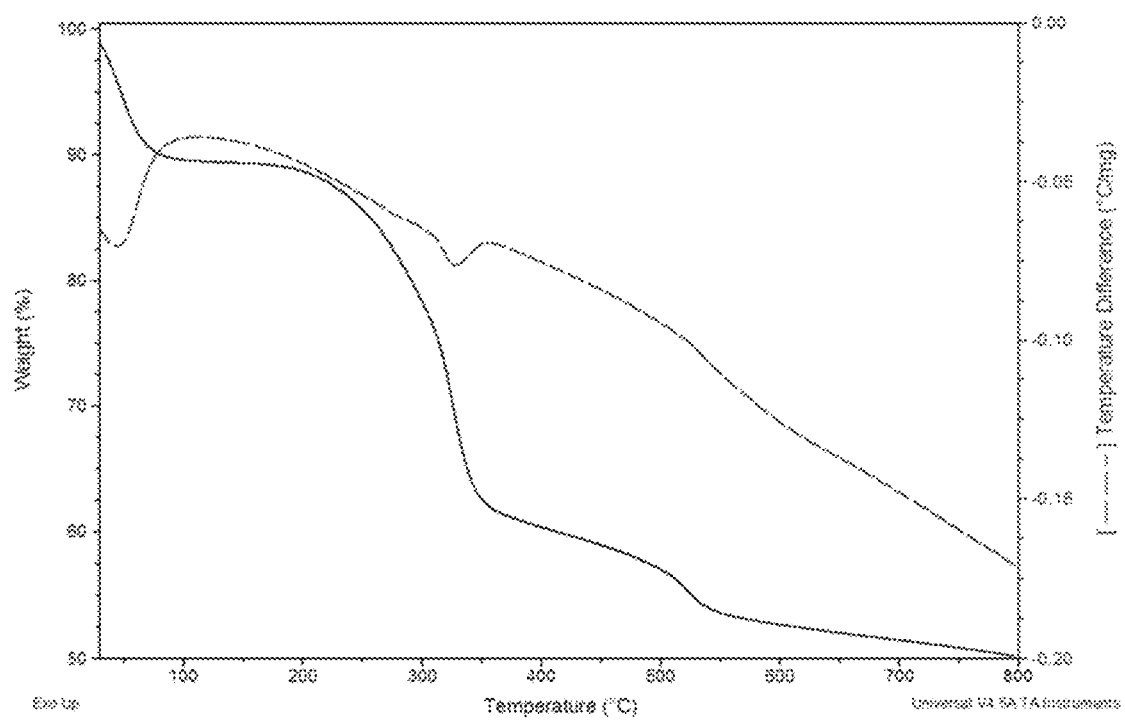

The isostructural nature in this materials platform was probed by a combination of synchrotron X-ray diffraction and Pair Distribution Function (PDF) analyses (FIG. 3A-3B). There is a very good correlation between the calculated and experimental synchrotron powder X-ray diffraction studies on all compounds (FIG. 3A). This finding illustrates both the phase purity and the structural similarities among the reported compounds.

Table 1 shows the unit cell lattice parameters for the analogs in this series, as refined from powder X-ray diffraction data. The X-ray single crystal data for the Eu structure was also included for comparison purposes. As expected, a gradual expansion of the unit cell volume is noted with the increase in the ionic radius for each of the M elements (e.g., rare earth metal elements) used here: Nd>Eu>Tb>Y>Yb.

TABLE 1

Refined unit cell lattice parameters for compounds 1-5; one sigma error bars are given in brackets

| Compound | a (Å) | c (Å) | Volume (Å³) |
| --- | --- | --- | --- |
| EuDOBDC, 1 | 15.36(1) | 21.76(2) | 5133(19) |
| EuDOBDC, 1 (single crystal) | 15.56 | 21.33 | 5163 |
| NdDOBDC, 2 | 15.50(1) | 21.89(1) | 5258(7) |
| YbDOBDC, 3 | 15.07(1) | 21.29(1) | 4834(7) |
| YDOBDC, 4 | 15.143(7) | 21.385(7) | 4904(6) |
| TbDOBDC, 5 | 15.23(2) | 21.51(1) | 4993(19) |

In addition, PDF analyses were conducted, in order to better interrogate the local structure in these systems (FIG. 3B). PDF is a powerful tool which provides detailed structural insights as a weighted histogram of atom-atom distances, independent of sample crystallinity.[39] Two main peaks in the lower r region are distinguishable, at ~2.5 Å and 4 Å, associated with the metal-O bond distance and metal-metal bond, respectively. These findings demonstrate that the coordination profile in these compounds is maintained at both long- and short-range, consistent with the expected isostructural nature.

Figure 5:
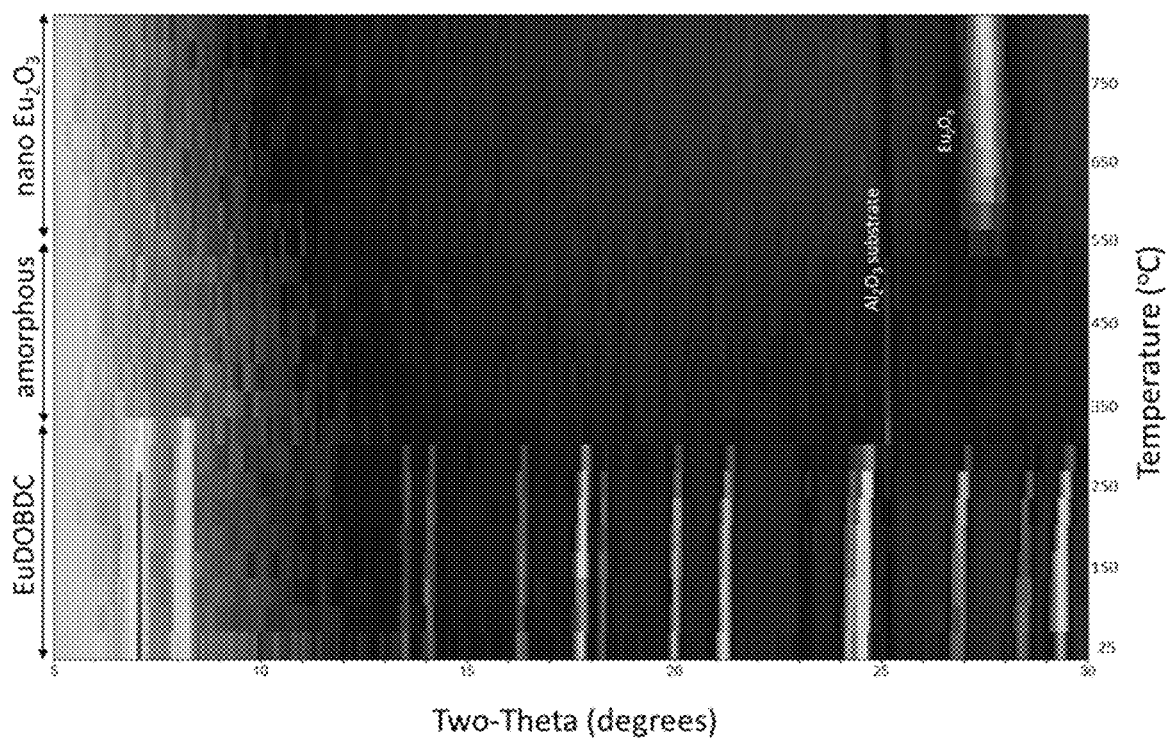
FIG. 5 shows variable temperature X-ray powder diffraction for compound 1.

Thermogravimetric analyses reveal that compounds 1-5 are stable until ~250° C. (FIG. 4A-4E). A gradual weight loss beyond this point is associated with slow framework decomposition. Additionally, this process was probed in detail via temperature controlled XRD for the EuDOBDC sample (FIG. 5). The in situ XRD analysis reveals a clear breakdown of the diffraction pattern above 250° C. with a complete loss of the EuDOBDC reflections and the formation of what appears to be an amorphous phase. Not until ~600° C. does the appearance of a new crystalline phase of $Eu_2O_3$ appear.

Figure 6:
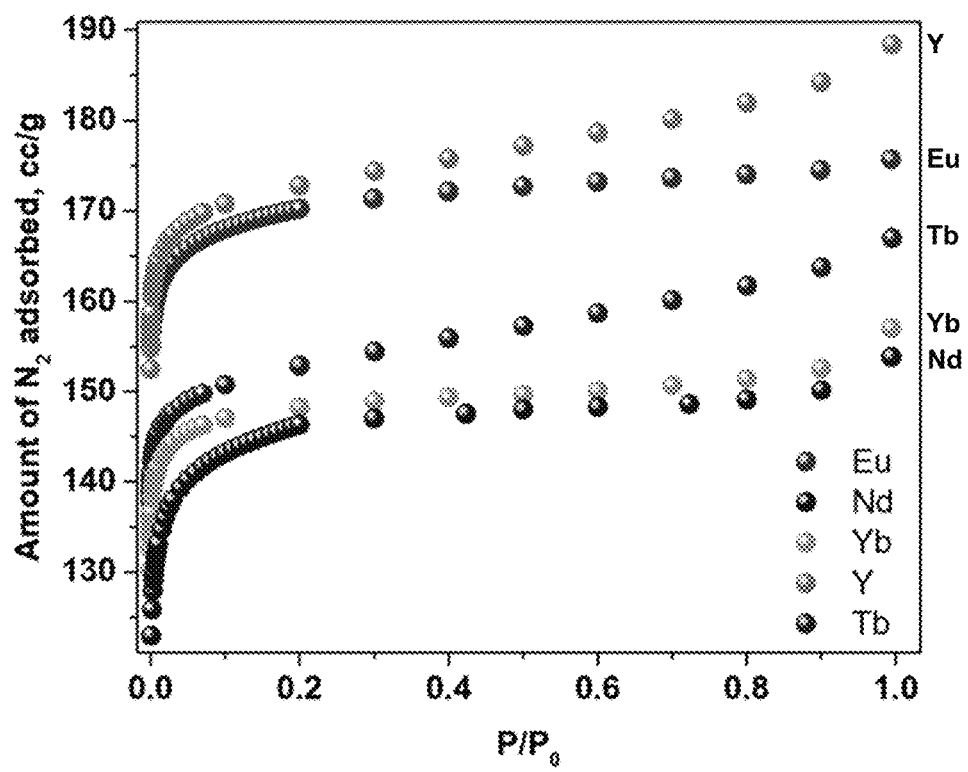
FIG. 6 shows nitrogen adsorption isotherms measured at 77K on compounds 1-5.

The crystal structure of 1 (FIG. 1C) reveals the potential for porous channels along X and Y directions. The permanent porosity was investigated by measuring the nitrogen adsorption isotherms at 77K on desolvated compounds 1-5 (FIG. 6). All five analogs adsorbed $N_2$ and exhibited a type I isotherm, characteristic to microporous materials. The surface areas were evaluated using the BET and Langmuir method, and were found to vary between 587 $m^2/g$ for the Nd sample to 710 $m^2/g$ for the Y sample (Table 2).

TABLE 2

Surface area analyses for compounds 1-5

| Compound | BET SA | Langmuir SA |
| --- | --- | --- |
| EuDOBDC, 1 | 700 $m^2/g$ | 730 $m^2/g$ |
| NdDOBDC, 2 | 587 $m^2/g$ | 620 $m^2/g$ |
| YbDOBDC, 3 | 613 $m^2/g$ | 630 $m^2/g$ |
| YDOBDC, 4 | 710 $m^2/g$ | 730 $m^2/g$ |
| TbDOBDC, 5 | 630 $m^2/g$ | 650 $m^2/g$ |

Figure 7:
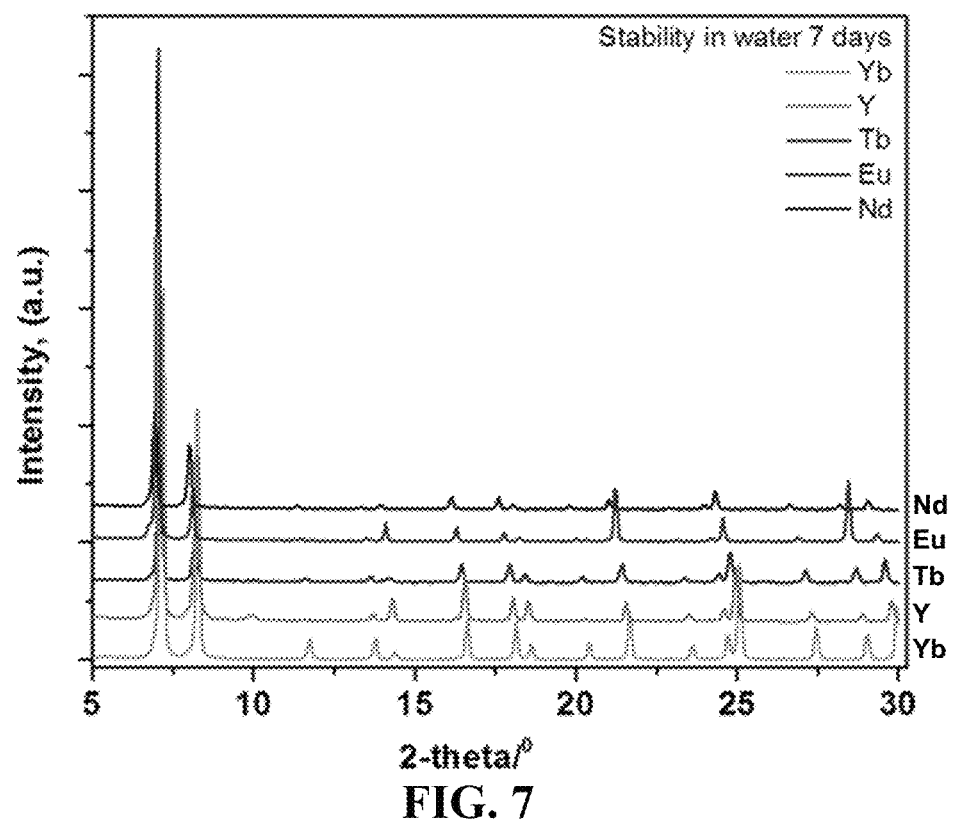
FIG. 7 shows powder X-ray diffraction (XRD) patterns of compounds 1-5 soaked in water for 7 days. Under these conditions, the compounds display stability and no change to the crystalline periodic network.
Figure 8:
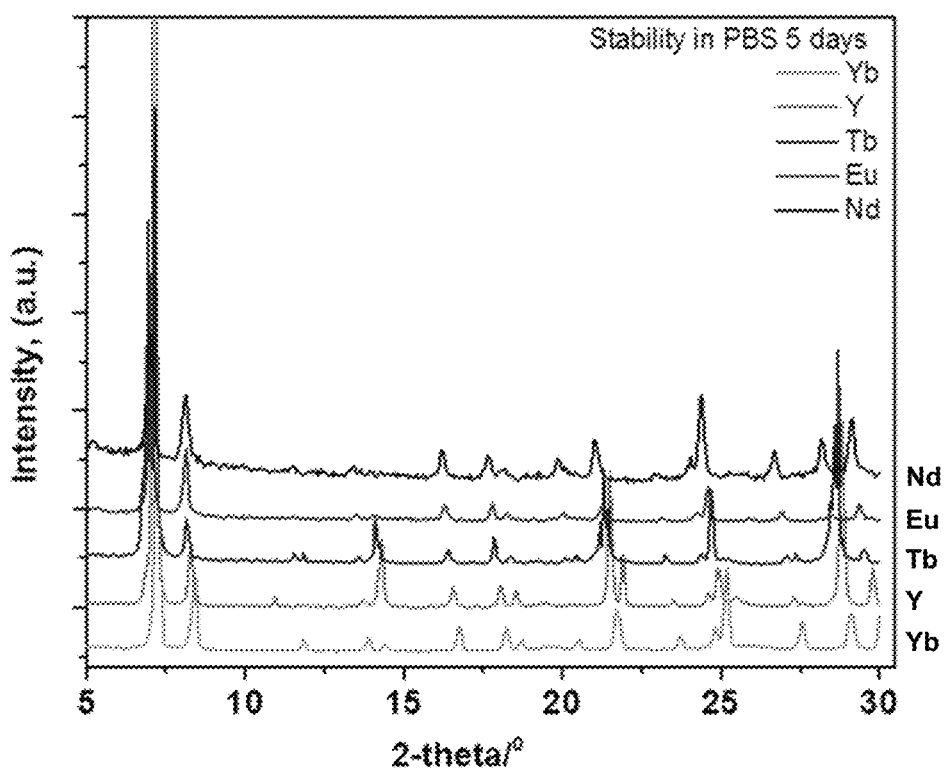
FIG. 8 shows PXRD patterns of compounds 1-5 soaked in phosphate-buffered saline (PBS) for 5 days. Under these conditions, the compounds display stability and no change to the crystalline periodic network.

In order to probe the relevance of using these materials as imaging agents, their chemical stability in water and phosphate buffered saline (PBS) was evaluated. X-ray diffraction patterns show no change to the original structure after immersion in water for 7 days (FIG. 7) and in PBS for 5 days (FIG. 8). These are unique attributes in the context of MOFs, which generally lack robustness under these conditions.

Example 4: X-Ray Single-Crystal Data Collection and Determination of Compound 1

The X-ray intensities were measured using a Bruker-D8 Venture dual-source diffractometer (Cu Kα, λ=1.5406 Å) and CMOS detector. Indexing and frame integration was performed using the APEX-III software suite. Absorption correction was performed using face-indexing (numerical method) also within the APEX-III software. The structures were solved using SHELXL-2014/7 and refined using SHELXTL XLMP version 2014/7. A minor-like disorder of the DOBDC ligand in the A-B plane of the structure was modeled with partial occupancy of either carbon or oxygen atoms. Due to the challenges of this disorder, isotropic atomic displacement parameters were used for oxygen and carbon atoms and hydrogens were not modeled in the structure. A significant solvent volume was detected and was modeled using PLATON/SQWEEZE to model the 48 solvent water molecules in the full unit cell (24 per formula unit). The water molecules and hydrogen atoms that were expected to be present on the DOBDC and OH molecules were accounted for in the final formula.

TABLE 3

Crystal data and structure refinement for compound 1.

| | |
| --- | --- |
| Empirical formula | C48 H94 Eu6 O74 |
| Formula weight | 2765.98 |
| Temperature | 102K |
| Wavelength | 1.54178 Å |
| Crystal system, space group | Tetragonal, P 4/m n c |
| Unit cell dimensions | a = 15.5567 Å |
| | b = 15.5567 Å |
| | c = 21.3340 Å |
| Volume | 5163.1 $Å^3$ |
| Z, Calculated density | 2, 1.779 $Mg/m^3$ |

TABLE 3-continued

Crystal data and structure refinement for compound 1.

| | |
| --- | --- |
| F(000) | 2702.0 |
| Crystal size | 0.048 × 0.060 × 0.125 mm |
| Theta range for data collection | 3.516 to 69.976° |
| Reflections collected/unique | 17835/2529 |
| R indices | R1 = 0.0434, wR2 = 0.1568 |
| Largest diff. peak and hole | −1.439 to 2.036 $eÅ^{-3}$ |

Example 5: Photoluminescence Properties of Exemplary MOF Compositions

Figure 9A:
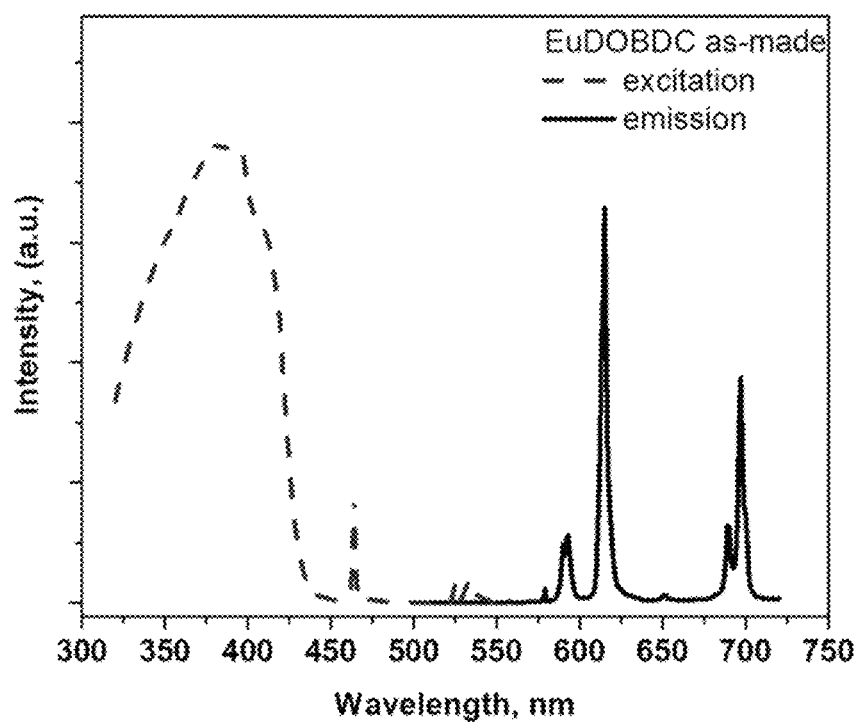
FIG. 9A-9B shows photoluminescence excitation (PLE) and emission (PL) spectra for the as-synthesized EuDOBDC sample, compound 1 (FIG. 9A) and the guest free (desolvated) EuDOBDC sample, compound 1 (FIG. 9B), in which the spectra are offset for clarity. The emission was monitored at 614 nm for the PLE measurements.
Figure 9B:
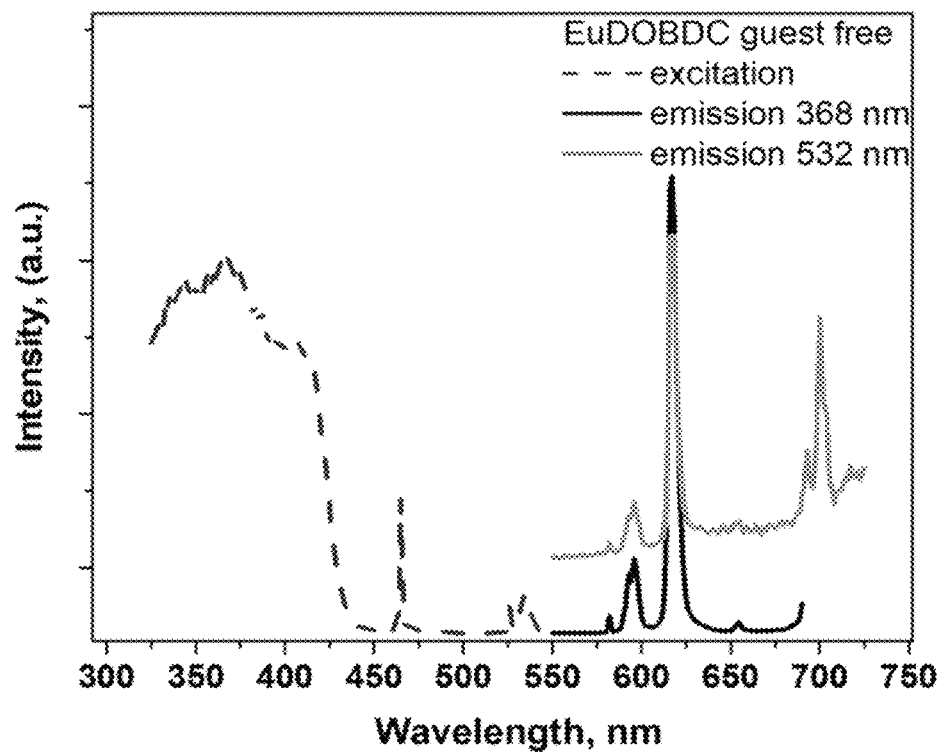

Trivalent lanthanides are known for their characteristic narrowband emission. The photoluminescence excitation (PLE) and emission (PL) spectra of compound 1 in the as-synthesized and desolvated state are shown in FIG. 9A and FIG. 9B, respectively. Although the environment within the pores is different in each of these samples, they both exhibit red emission, characterized by narrowband peaks between 590-725 nm. These are assigned to the $Eu^{3+}$ parity forbidden $^5D$-$^7F$ transitions at ~590 nm (magnetic dipole transition $^5D_0$-$^7F_1$), and electric dipole transitions at ~616 nm ($^5D_0$-$^7F_2$), 650 nm ($^5D_0$-$^7F_3$), and 700 nm ($^5D_0$-$^7F_4$).[11]

The PL emission of compound 1 does not depend on the excitation wavelength. FIG. 9B shows the PL spectra under 368 nm excitation, which sensitizes the $Eu^{3+}$ via the excited states of the ligand; and 532 nm which directly excites the 4f-4f transitions of $Eu^{3+}$. Direct excitation has lower efficiency due to the very low molar extinction coefficient of $Eu^{3+}$ at 532 nm.

Figure 10A:
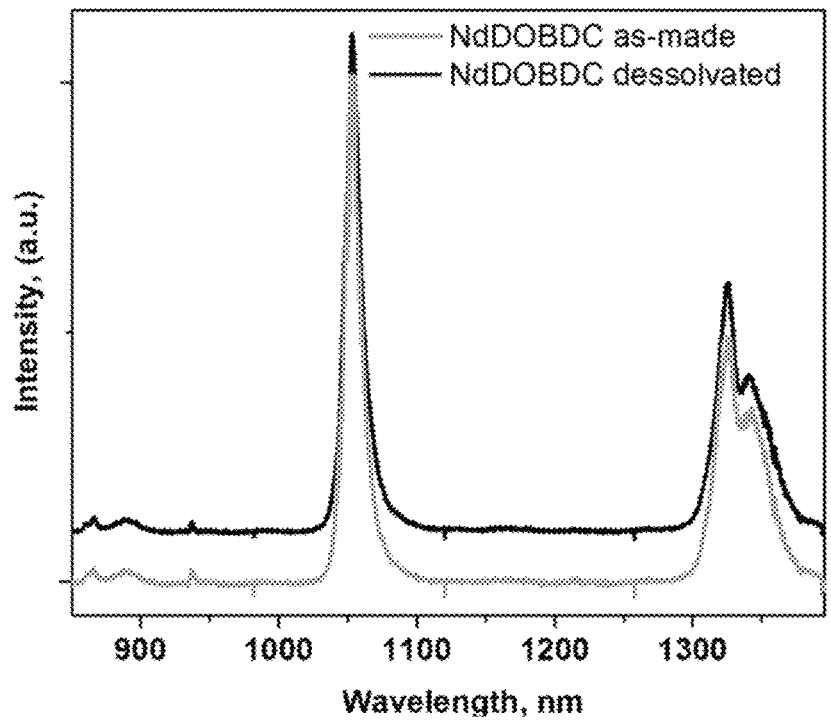
FIG. 10A-10B shows PL emission spectra at 808 nm excitation for the as-synthesized, and guest free (desolvated) NdDOBDC sample, compound 2 (FIG. 10A), in which the spectra are offset for clarity; and for the mixed metal $Nd_{0.67}Yb_{0.33}$ DOBDC, compound 6 and $Nd_{0.46}Yb_{0.54}$DOBDC samples, compound 7 (FIG. 10B).

Next, the NIR-emitting compounds 2, 6 and 7 containing $Nd^{3+}$ and $Nd^{3+}/Yb^{3+}$ were characterized. Under 808 nm excitation, the Nd-based framework (FIG. 10A, compound 2) displayed a sharp emission band at ~1060 nm, associated with $^4F_{3/2}$-$^4I_{11/2}$ transitions and a broader split band centered at 1325 nm, correlated with $^4F_{3/2}$-$^4I_{13/2}$ transitions. $Nd^{3+}$ also has very weak emission band at ~890 nm (not shown), and is attributed to the $^4F_{3/2}$-$^4I_{9/2}$ transitions.[28]

Figure 10B:
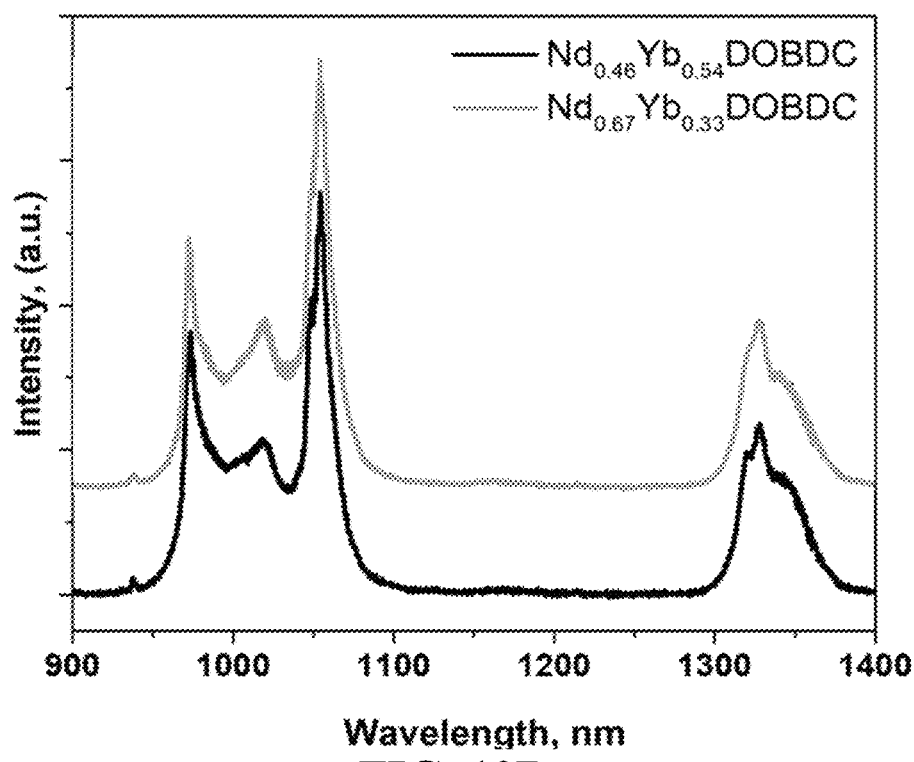
Figure 11:
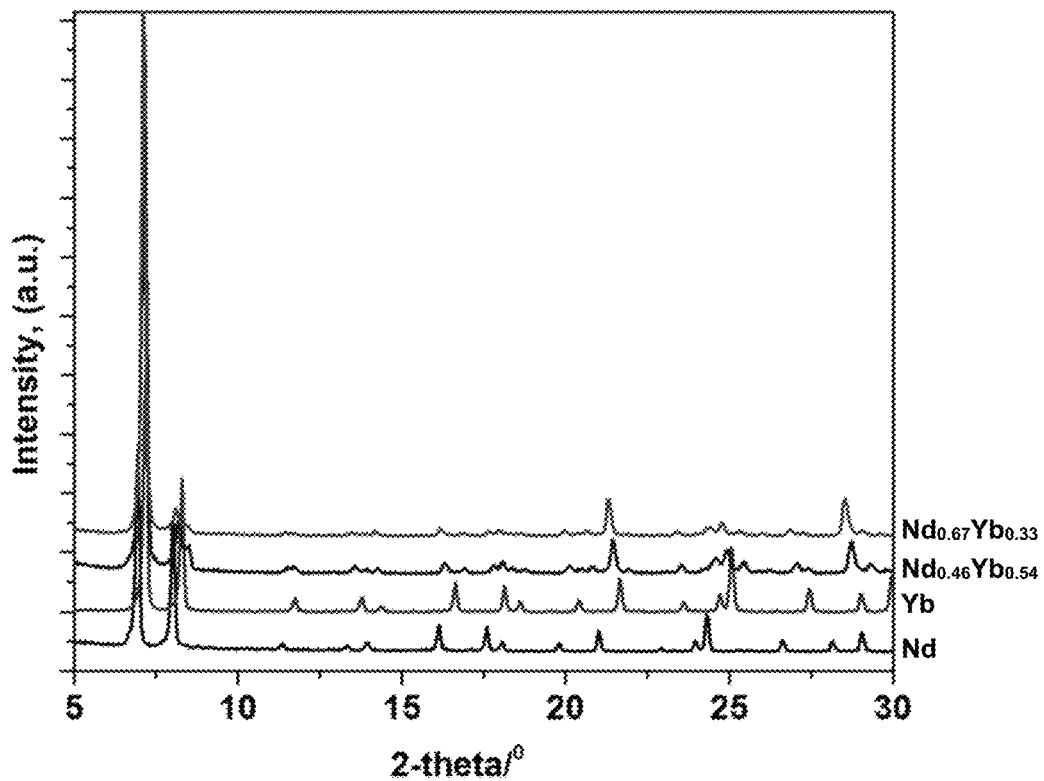
FIG. 11 shows PXRD patterns of Nd and YbDOBDC compounds and that of the tuned compositions of $Nd_{0.46}Yb_{0.54}$ and $Nd_{0.67}Yb_{0.33}$ DOBDC analogs, showing the anticipated direct structural correlation between all phases.
Figure 12A:
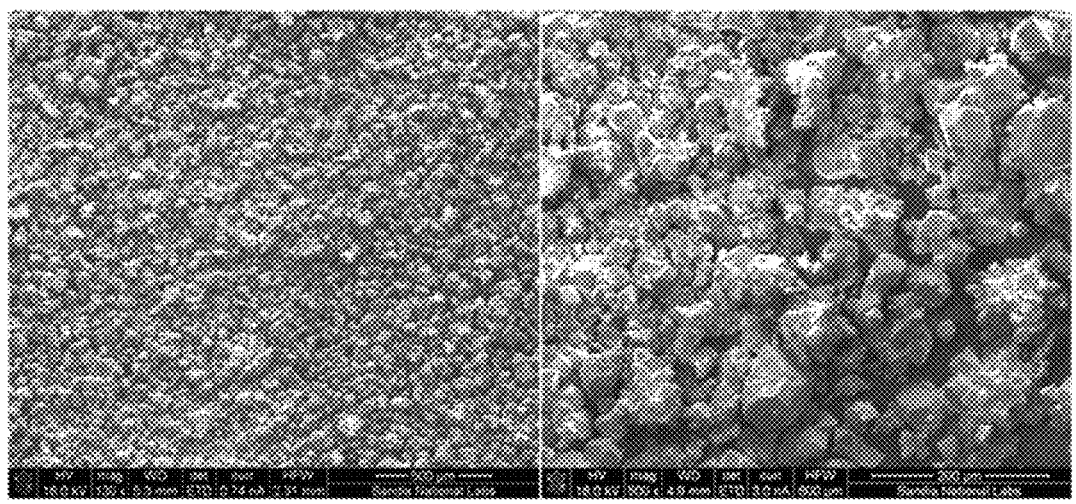
FIG. 12A-12B shows scanning electron microscopy (SEM)-energy dispersive spectroscopy (EDS) analyses of compound 6. Provided are SEM images (FIG. 12A) and EDS spectrum (FIG. 12B).
Figure 12B:
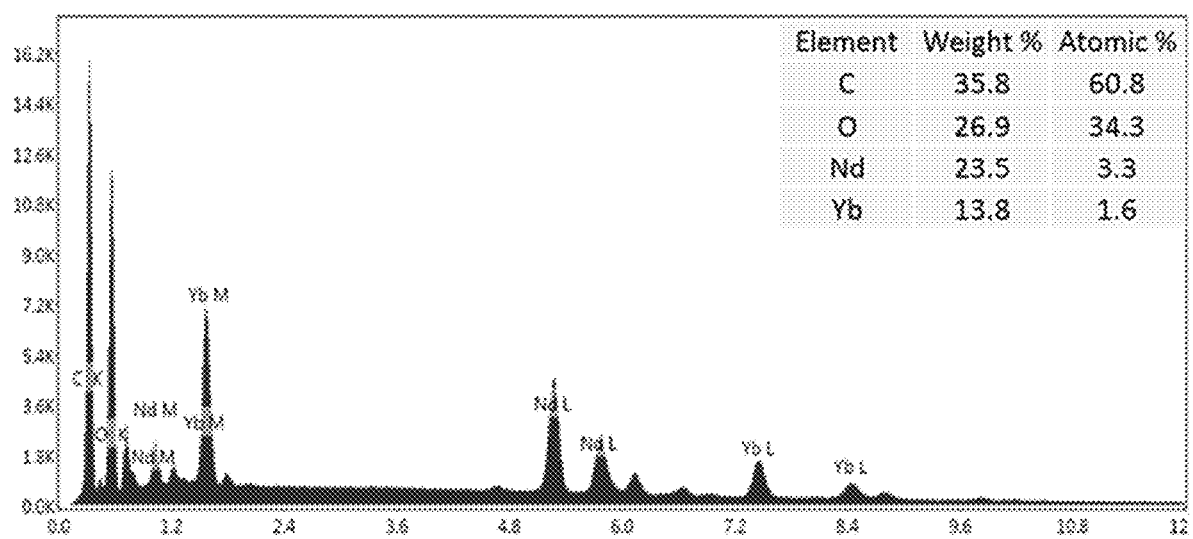
Figure 13A:
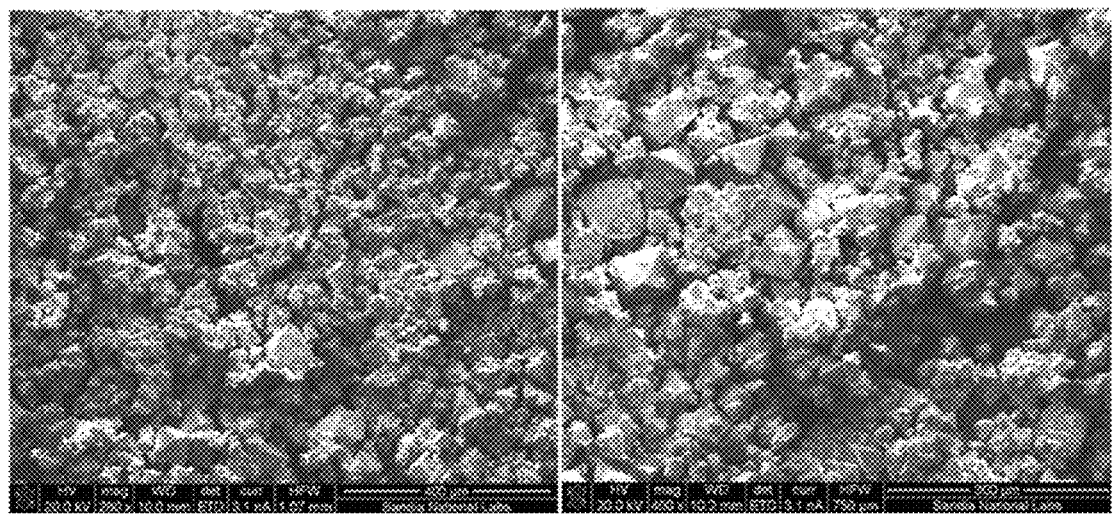
FIG. 13A-13B shows SEM-EDS analyses of compound 7. Provided are SEM images (FIG. 13A) and EDS spectrum (FIG. 13B).
Figure 13B:
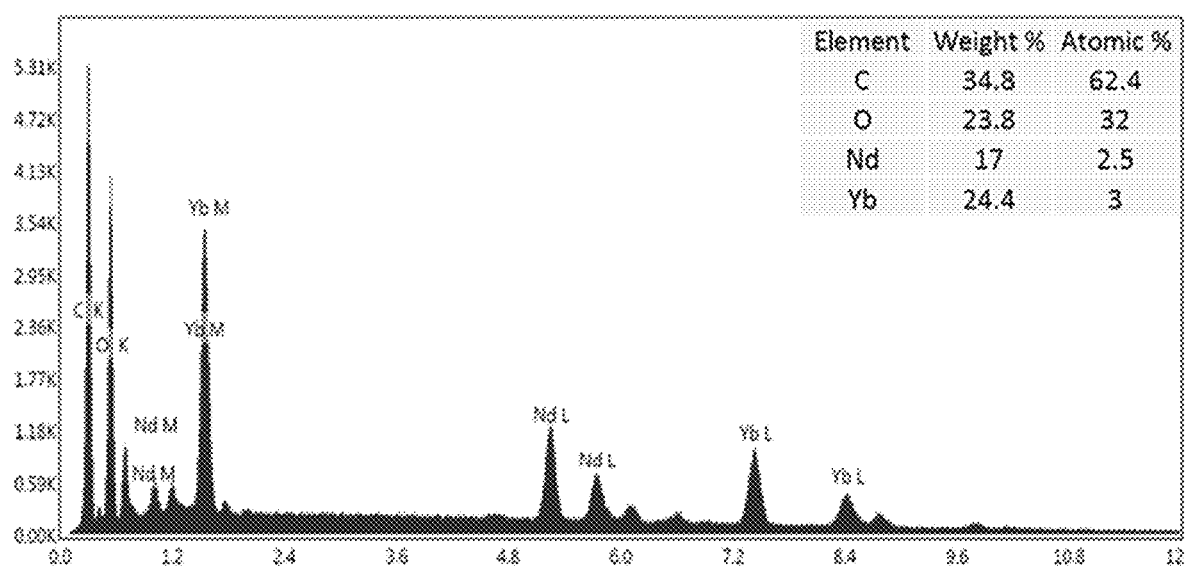

In order to exploit the tunability uniquely intrinsic to MOFs, we also designed mixed Nd/Yb samples, at two distinct compositions, $Nd_{0.67}Yb_{0.33}DOBDC$, 6 and $Nd_{0.46}Yb_{0.54}DOBDC$, 7. As expected, compounds 6 and 7 display NIR emission from both the Nd and Yb ions, when excited at 808 nm. This wavelength directly excites the Nd ions, upon which energy is transferred non-radiatively from the $^4F_{5/2}$ energy level of $Nd^{3+}$ to the $^5F_{5/2}$ energy level of $Yb^{3+}$, to allow the narrow emission band at 980 nm, characteristic of $Yb^{3+}$ (FIG. 10B). FIG. 11 also shows PXRD patterns of Nd and YbDOBDC compounds and that of the tuned compositions of $Nd_{0.46}Yb_{0.54}$ and $Nd_{0.67}Yb_{0.33}$ DOBDC analogs, showing the anticipated direct structural correlation between all phases. SEM-EDS analysis were also conducted for compound 6 (FIG. 12A-12B) and compound 7 (FIG. 13A-13B).

Example 6: MOF-Based Nanoparticles

Figure 14A:
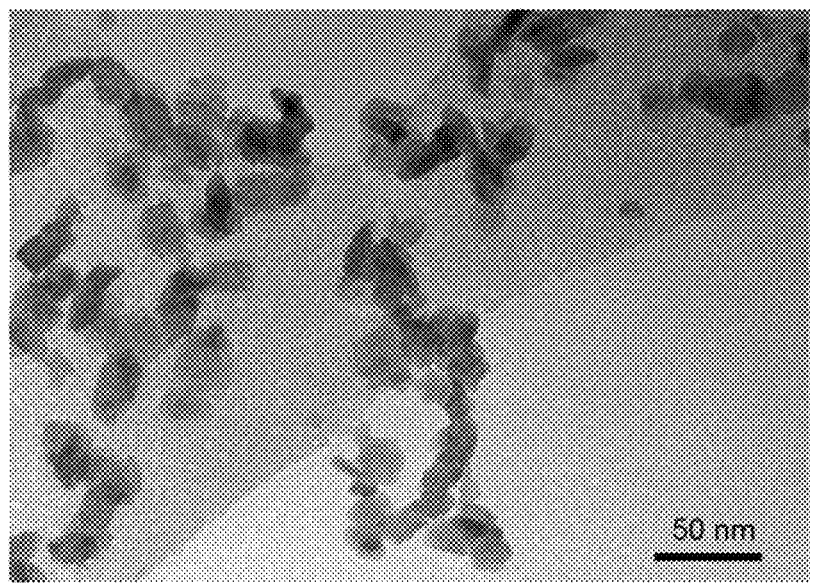
FIG. 14A-14C shows structural characterization of EuDOBDC-NP. Provided are transmission electron microscopy (TEM) microscopy images (FIG. 14A); $N_2$ sorption isotherm measured at 77 K (FIG. 14B); and emission spectra and red-emitting EuDOBDC-NP as characterized by hyperspectral confocal fluorescence microscopy (FIG. 14C).
Figure 14B:
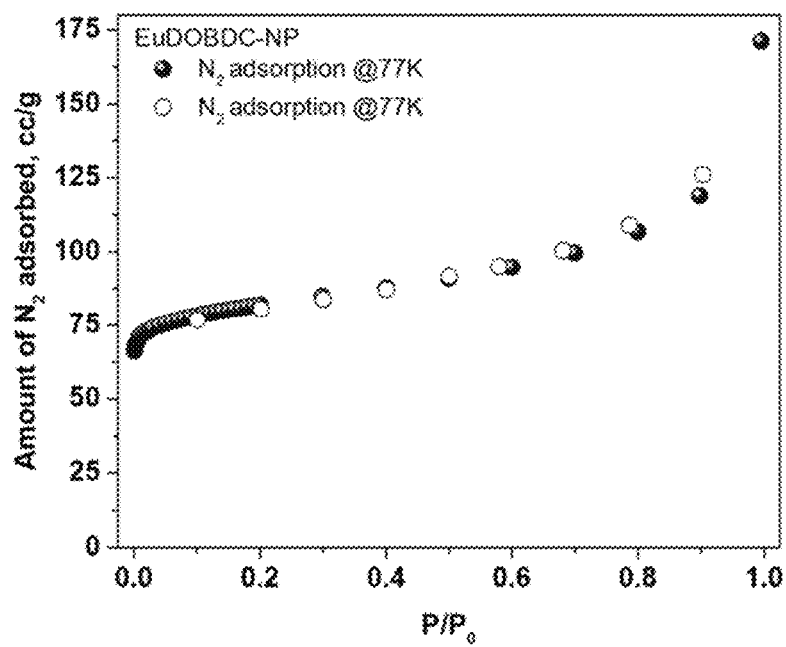
Figure 14C:
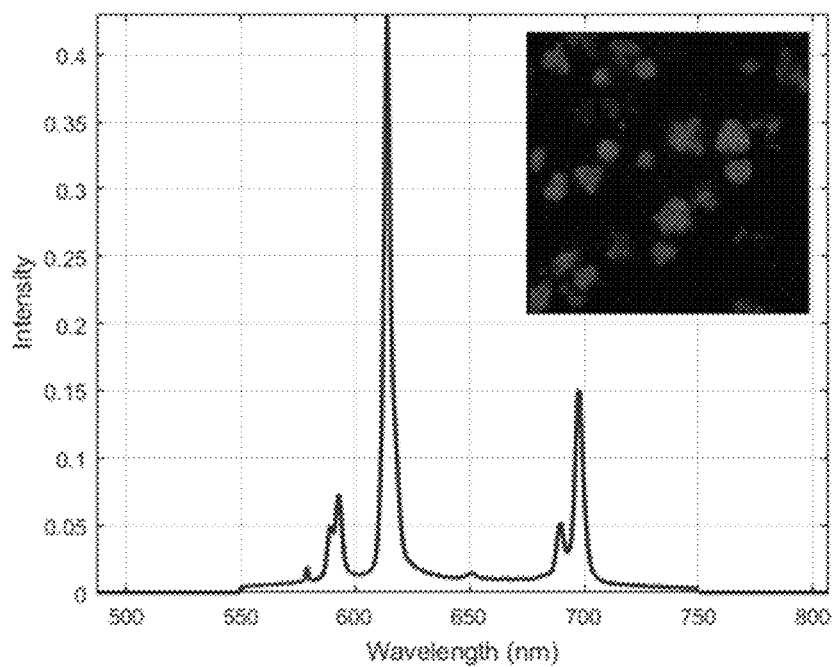
Figure 15:
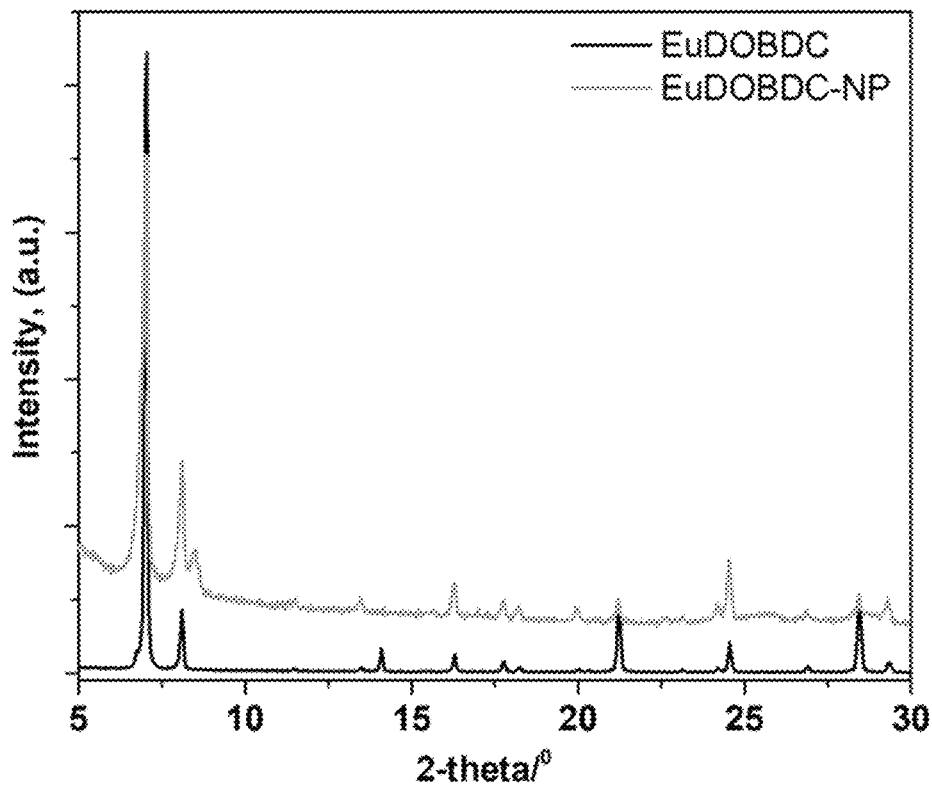
FIG. 15 shows PXRD patterns of EuDOBDC and that of the nanoscale analog, EuDOBDC-NP, showing the anticipated direct structural correlation between the two phases.

In an effort to probe the relevance of our newly designed materials platform to bio-imaging applications, we first attempted the synthesis of the nanoscale analog for the red-emitting Eu-based framework. This choice was primarily dictated by the availability of conventional single photon microscopy techniques associated with emission in the visible range. The development of nano-MOFs for biomedicine is still scarcely reported, and only in recent years, some progress has been made in this direction.[40] Here, we successfully synthesized the nanoscale analog of compound 1, EuDOBDC-NP, via a microwave-assisted approach (FIG. 14A-14C). FIG. 15 shows PXRD patterns of EuDOBDC and that of the nanoscale analog, EuDOBDC-NP, showing the anticipated direct structural correlation between the two phases.

The TEM images reveal a fairly homogeneous distribution of particles in the 20-50 nm range (FIG. 14A). Nitrogen adsorption studies were conducted on a desolvated sample, showing a BET surface area of 315 $m^2/g$ (FIG. 14B). A reduced amount of $N_2$ gas was adsorbed in EuDOBDC-NP, as compared to the original EuDOBDC micron sized particles. This phenomenon has been previously observed in other nanoparticle sized MOFs,[41] and it may be associated with incomplete removal of pore guest molecules during the activation procedure.

In order to investigate the dispersion of EuDOBDC-NP in various environments, dynamic light scattering measurements (DLS) measurements were conducted on samples in methanol, PBS, and DMEM media+FBS (Table 4).

TABLE 4

Particle size distribution via DLS measurements on the EuDOBDC-NP in various environments (PdI = polydispersity index)

| Solution | Hydrodynamic Size (nm) | Polydispersity index (PdI) |
|---|---|---|
| MeOH | 446.3 (+/−28.3) | 0.213 (+/−0.92) |
| PBS | 963.7 (+/−140.1) | 0.446 (+/−0.151) |
| DMEM media + FBS | 1021 (+/−254.0) | 0.784 (+/−0.36) |

The particle size measured by DLS was larger than that based on the TEM measurement, likely due both to agglomeration of the EuDOBDC-NP in solution and to the nature of the DLS measurement itself. Unlike TEM, DLS measures the hydrodynamic diameter of the particles in solution, which includes the hydration layer and any associated proteins or stabilizers absorbed from the solution, leading to larger particle sizes than dried imaging measurements like TEM.[42] Additionally, the DLS measurement is based on light scattering, which is proportional to the sixth power of the particle diameter, and in the case of a polydisperse particle or agglomeration, will result in the larger particles strongly influencing the final size measurement.[42]

A significant increase in size between DLS and TEM measurements of nanosized MOFs has also previously been reported.[43] As most, if not all, therapeutic and imaging based biological applications require dispersion in solution of some kind, measurement of the hydrodynamic size is important to understanding the behavior of the EuDOBDC-NP in biologically relevant environments. The particle size increase is accentuated in biologically relevant solutions, such as PBS and DMEM media with FBS. This size increase correlates with amplified aggregation, most likely due to the particle's interaction with complex components in both PBS and cell culture media, previously observed with MOFs.[44] This suggests that additional surface modifications might be needed in order to improve the dispersion of the particles in biologically relevant solutions for biological applications.

Example 7:—Cellular Toxicity Studies with MOF Compositions

Figure 16A:
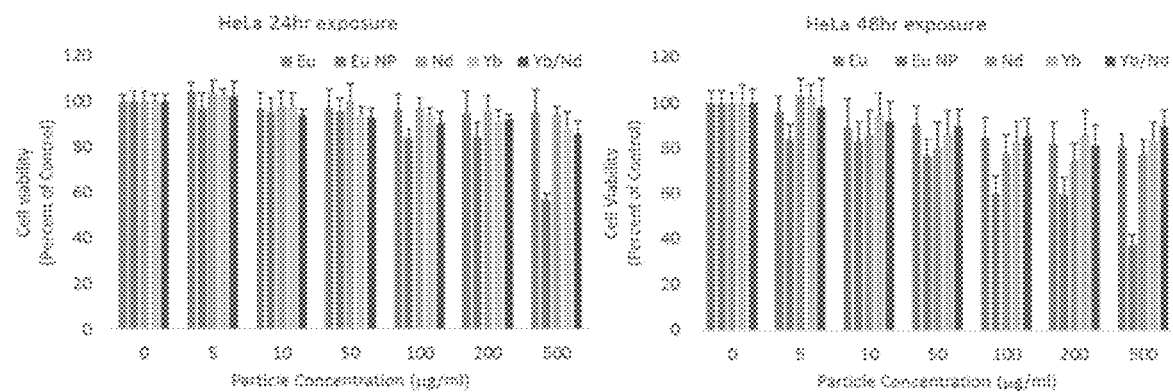
FIG. 16A-16B shows cellular viability employing HeLa cells (FIG. 16A) or RAW 264.7 mouse macrophage cells (FIG. 16B) after exposure with various MOF compositions. Data are provided after 24 hours of incubation (left panel) and 48 hour of incubation (right panel) for five different compositions: Eu, Eu NP, Nd, Yb, and Yb/Nd from left to right, respectively. These data show minimal toxicity to both studied cell lines, in which more than 80% of cells survive at both 24 hours and 48 hours with doses up to 200 µg/mL.
Figure 16B:
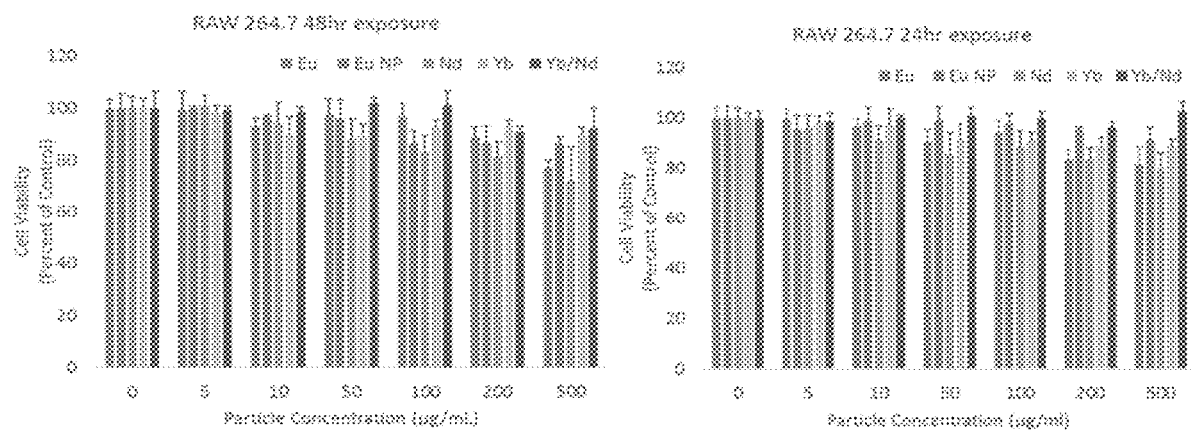

Prior to conducting live cell imaging, we assessed the toxicity to mammalian cells in compounds 1, 1-NP, 2, 3, and 6 at both 24 and 48 hrs, at various concentrations up to 500 µg/mL (FIG. 16A-16B). The micro-sized particles (compounds 1, 2, 3 and 6) demonstrated little to no cytotoxicity regardless of composition, with greater than 80% of cells surviving at both 24 and 48 hrs with doses up to 200 µg/mL.

The nanoscale Eu analog demonstrated increased toxicity compared to the micro-sized Eu particles. Enhanced toxicity on the nanoscale compared to the microscale has been documented for metal nanoparticles.[45] The particles displayed both a dose dependent and a time dependent toxicity, which was increased in human epithelial cells compared to the mouse macrophages. Differential toxicity between cell types has previously been observed with both other nanoparticles[46] and with other MOFs.[47] The mouse macrophages displayed greater than 80% cell viability at both 24 and 48 hrs, even with the 500 µg/mL dose for 1-NP. Although an increase in toxicity was seen with the human epithelial cells, decreased cell viability below 80% was only seen with very high dose (500 µg/mL) or 48-hour incubation times demonstrating very low toxicity of the Eu nanoparticle overall. The toxicity demonstrated by the EuDOBDC-NP is equal to or significantly lower than the toxicity of many other nanoscale MOF formulations currently being developed for biological imaging or drug delivery.[25,47,48]

Figure 17A:
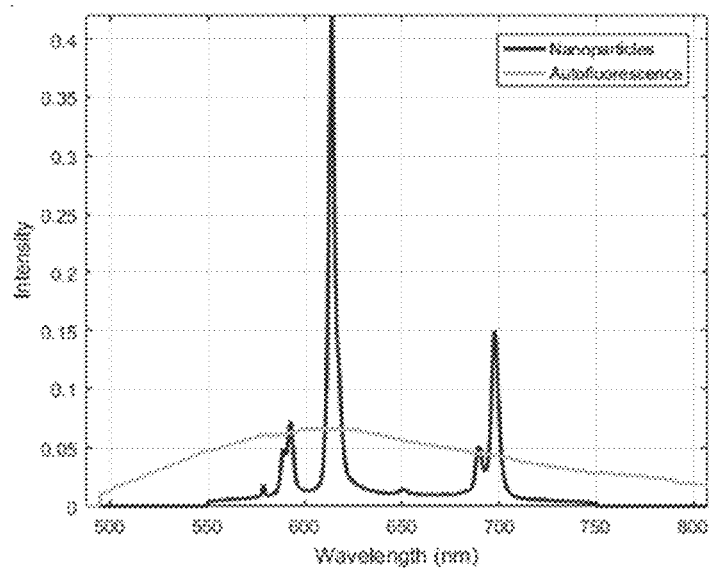
FIG. 17A-17B shows bioimaging characteristics of EuDOBC-NP. Provided are multivariate curve resolution (MCR) spectral components showing cell autofluorescence and the emission spectra of EuDOBC-NP (FIG. 17A); and hyperspectral confocal fluorescence microscopy images of HeLa human cervical cancer cells and RAW 264.7 mouse macrophage cells incubated with EuDOBDC-NP (20 µg/mL) for 2 hours (upper two panels) or 48 hours (lower two panels) (FIG. 17B).
Figure 17B:
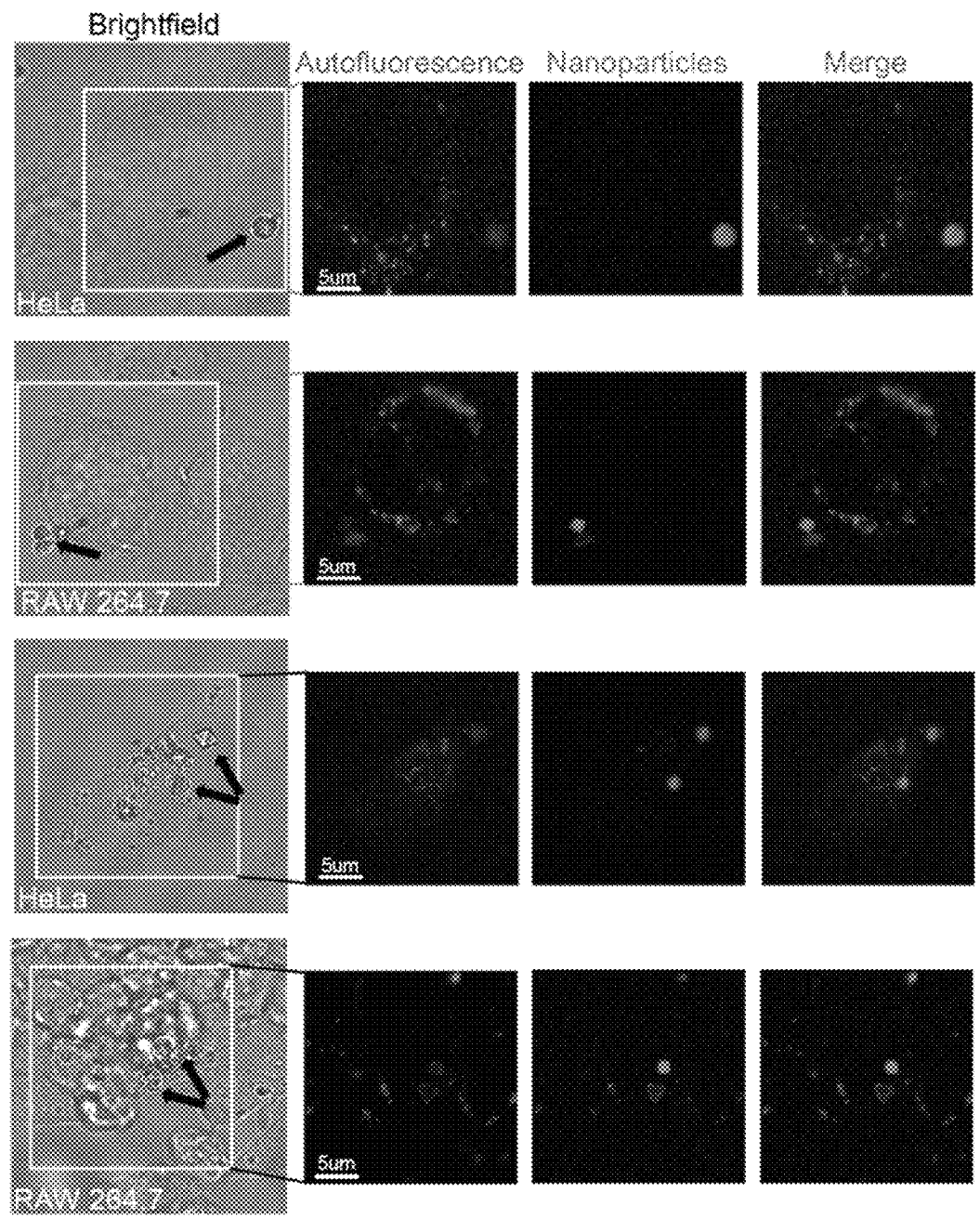
Figure 18:
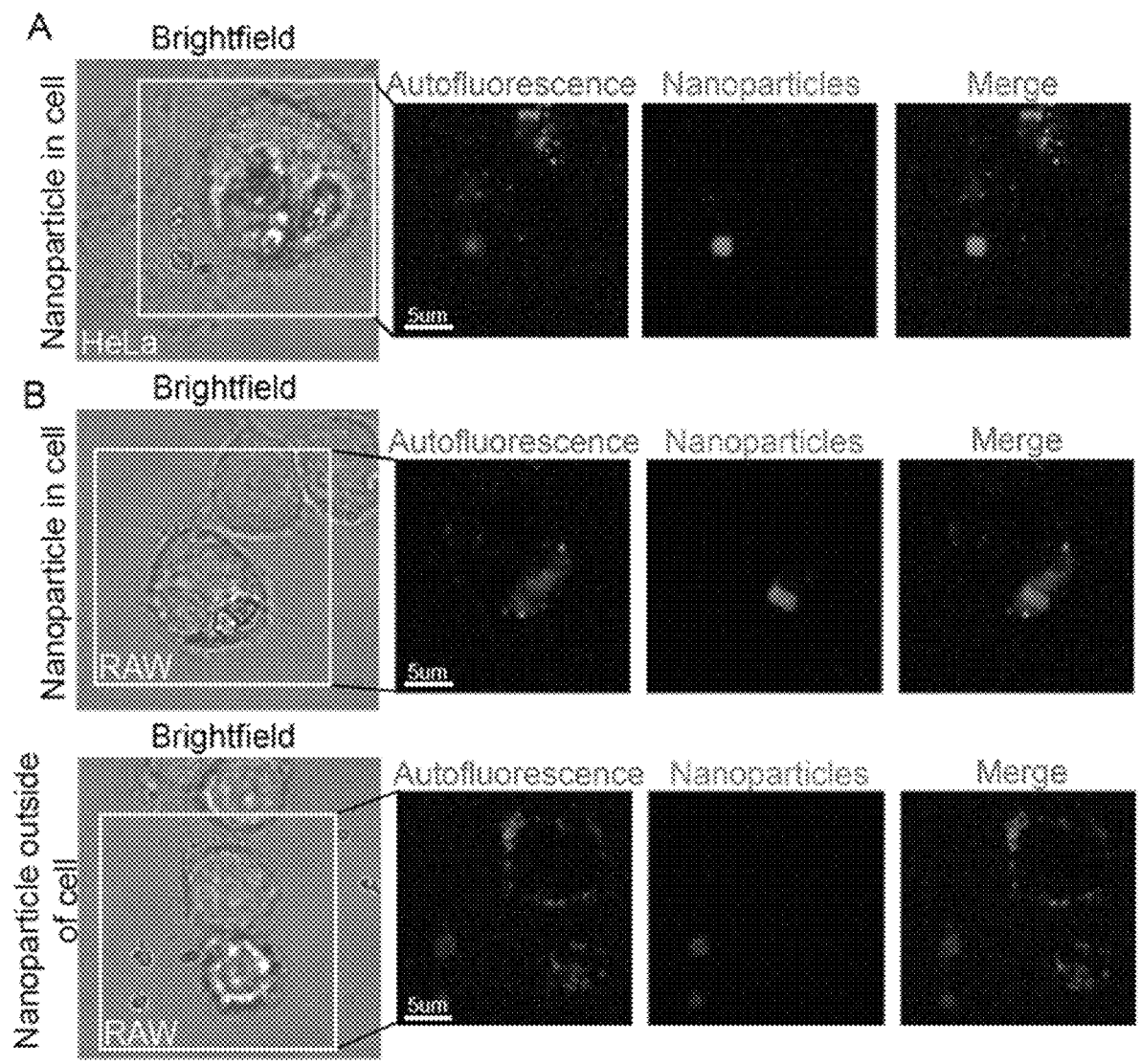
FIG. 18 shows hyperspectral confocal fluorescence microscopy images of HeLa human cervical cancer cells (panel A) and RAW 264.7 mouse macrophage cells (panel B) incubated with EuDOBDC-NP (20 µg/mL) for 2 hours. Images show the distribution of the EuDOBDC-NP within the cell, as well as outside of the cell.

Next, we undertook live cell imaging using a customized hyperspectral confocal fluorescence microscope (FIG. 17A-17B and FIG. 18). This technique is uniquely poised to characterize the interaction of nanoparticles with cells, as it provides a direct measurement of the emission spectrum from each image voxel. MCR analysis was further used to extract the independently varying emission components (FIG. 17A). This is the first time this technique has been used to characterize MOF nanoparticles, although it has been previously implemented to assess interactions of quantum dots with cells.[49]

Following an initial 2 hrs incubation period at a 20 µg/mL concentration, nanoparticle uptake was observed only in a small portion of cells (~10%) (FIG. 18). Given that HCFM is a confocal microscope with axial resolution of approximately 600 nm and the approximate cell thickness is 5-10 µm, particles that were in focus and inside the cell membrane's periphery were considered to be internalized. The majority of cells displayed nanoparticles stuck to the cell surface and decorating the coverslip around the cells, as seen in the two top panels in FIG. 17B.

Motivated by the interest to assess the relevance of these materials as long-term imaging agents, we further examined the particles following a 48 hrs incubation cycle, at the 20 µg/mL concentration. At this timepoint, 100% of HeLa cells and 74% of RAW cells had attached or incorporated nanoparticles, as seen in the bottom two panels in FIG. 17B. At 48 hrs, some of the cells appear to have taken up multiple particles, ranging from 2-11 particles per cell in HeLa and RAW cells. Importantly, the spectrum of the nanoparticles was the same in solution, in tissue culture media and regardless of incubation time indicating that the molecular composition remains unchanged in different environments. The intensity of the signal was markedly lower for the longer incubation time (48 hrs) indicating perhaps some loss or degradation of the material under these conditions. Correlating these findings with the cytotoxicity assays, this behavior can be associated to increased toxicity to the cell over time, possibly due to nanoparticle degradation in biological media. However, the red emission was still preserved in 25% of particles in HeLa cells and 39% in RAW 264.7 cells after 48 hrs in cell media.

This is an important finding, as this is the first example of a luminescent MOF that shows its emission preservation in live cells at this extended incubation time. Given the low cytotoxicity and the stable emission, the EuDOBDC-NP indicate suitability for long-term tracking experiments. However, the aggregation in biological media, shown in both the DLS and imaging studies suggest additional steps might be needed to further stabilize and/or disaggregate the particles.

Initial proof-of-concept in vitro studies using RAW 264.7 mouse macrophage and HeLa human cervical cancer tissue culture cells demonstrate the viability of using these materials as bio-imaging agents. Notably, the red emission is preserved even at 48 hrs in both cell lines studied here, which in combination with the low cytotoxicity qualifies these probes as promising candidates for long-term biodistribution and tracking experiments.

Ongoing work is focused on the synthesis of the nanoparticle analogs for the NIR emitting compounds, in order to evaluate their performance for in vivo small animal imaging. Additionally, we are exploiting their use as theranostic agents, as facilitated by the unique intrinsic luminescence-porosity combination in this tunable MOF materials platform. In some embodiments, the MOF compositions are permanently porous and display tunable emission properties over a wide range, from deep red into the second NIR window. Such materials can meet essential prerequisites as relevant to bio-related applications, such as minimally toxicity and/or long-term stability (e.g., long-term crystallinity under relevant physiological conditions).

REFERENCES FOR EXAMPLES

1. Pansare V J et al., "Review of long-wavelength optical and NIR imaging materials: contrast agents, fluorophores, and multifunctional nano carriers," *Chem. Mater.* 2012; 24:812-27.
2. Smith A M et al., "Bioimaging: second window for in vivo imaging," *Nat. Nanotechnol.* 2009; 4:710-1.
3. Hemmer E et al., "exploiting the biological windows: current perspectives on fluorescent bioprobes emitting above 1000 nm," *Nanoscale Horizons* 2016; 1:168-84.
4. Chen Z et al., "Near-infrared (NIR) luminescence from lanthanide(III) complexes," Chapter 12 in *Rare Earth Coordination Chemistry: Fundamentals and Applications* (C Huang, ed.), John Wiley & Sons Ltd. (Chichester, UK, 2010), pp. 473-527.
5. Kim D et al., "Recent advances in inorganic nanoparticle-based NIR luminescence imaging: semiconductor nanoparticles and lanthanide nanoparticles," *Bioconjugate Chem.* 2017; 28:115-23.
6. Antaris A L et al., "A small-molecule dye for NIR-II imaging," *Nat. Mater.* 2016; 15:235-42.
7. Zhang X D et al., "Traumatic brain injury imaging in the second near-infrared window with a molecular fluorophore," *Adv. Mater.* 2016; 28:6872-9.
8. Escobedo J O et al., "NIR dyes for bioimaging applications," *Curr. Opin. Chem. Biol.* 2010; 14:64-70.
9. Pichaandi J et al., "Near-infrared emitting quantum dots: recent progress on their synthesis and characterization," *Coord. Chem. Rev.* 2014; 263-264:138-50.
10. Welsher K et al., "A route to brightly fluorescent carbon nanotubes for near-infrared imaging in mice," *Nat. Nanotechnol.* 2009; 4:773-80.
11. Bünzli J C et al., "Taking advantage of luminescent lanthanide ions," *Chem. Soc. Rev.* 2005; 34:1048-77.
12. Moore E G et al., "From antenna to assay: lessons learned in lanthanide luminescence," *Acc. Chem. Res.* 2009; 42:542-52.
13. Nesmerak K, "Lanthanide/actinide toxicity," in *Encyclopedia of Metalloproteins* (R H Kretsinger, V N Uversky, E A Permyakov, eds.), Springer (New York, N.Y., 2013), pp. 1098-1103.
14. Ruiz-Medina A et al., "Lanthanide-sensitized luminescence as a promising tool in clinical analysis," *Appl. Spectrosc. Rev.* 2011; 46:561-80.
15. Xu L J et al., "Recent advances in lanthanide luminescence with metal-organic chromophores as sensitizers," *Coord. Chem. Rev.* 2014; 273-274:47-62.
16. Furukawa H et al., "The chemistry and applications of metal-organic frameworks," *Science* 2013; 341:1230444 (12 pp.).
17. Allendorf M D et al., "Luminescent metal-organic frameworks," *Chem. Soc. Rev.* 2009; 38:1330-52.
18. Cui Y et al., "Lanthanide metal-organic frameworks for luminescent sensing and light-emitting applications," *Coord. Chem. Rev.* 2014; 273-274:76-86.
19. Cui Y et al., "Luminescent functional metal-organic frameworks," *Chem. Rev.* 2012; 112:1126-62.
20. Sava D F et al., "Intrinsic broad-band white-light emission by a tuned, corrugated metal-organic framework," *J. Am. Chem. Soc.* 2012; 134:3983-6.
21. Sava Gallis D F et al., "Efficient photoluminescence via metal-ligand alteration in a new MOFs family," *Chem. Mater.* 2014; 26:2943-51.
22. He C et al., "Nanomedicine applications of hybrid nanomaterials built from metal-ligand coordination bonds: nanoscale metal-organic frameworks and nanoscale coordination polymers," *Chem. Rev.* 2015; 115:11079-108.
23. Guo Z et al., "A robust near infrared luminescent ytterbium metal-organic framework for sensing of small molecules," *Chem. Commun.* 2011; 47:5551-3.
24. White K A et al., "Near-infrared luminescent lanthanide MOF barcodes," *J. Am. Chem. Soc.* 2009; 131:18069-71.
25. Foucault-Collet A et al., "*Lanthanide near infrared imaging in living cells with* Yb3+ *nano metal organic frameworks*," *Proc. Nat'l Acad. Sci. USA* 2013; 110:17199-204.
26. Zhao D et al., "A highly sensitive near-infrared luminescent metal-organic framework thermometer in the physiological range." *Chem. Commun.* 2016; 52:8259-62.
27. White K A et al., "Near-infrared emitting ytterbium metal-organic frameworks with tunable excitation properties," *Chem. Commun.* 2009; 30:4506-8.
28. Yang J et al., "Structures, photoluminescence, up-conversion, and magnetism of 2d and 3d rare-earth coordination polymers with multicarboxylate linkages," *Inorg. Chem.* 2006; 45:2857-65.
29. Xue D X et al., "Tunable rare-earth fcu-MOFs: a platform for systematic enhancement of $CO_2$ adsorption energetics and uptake," *J. Am. Chem. Soc.* 2013; 135:7660-7.
30. Luebke R et al., "Versatile rare earth hexanuclear clusters for the design and synthesis of highly-connected ftw-MOFs," *Chem. Sci.* 2015; 6:4095-102.
31. Guillerm V et al., "Discovery and introduction of a (3,18)-connected net as an ideal blueprint for the design of metal-organic frameworks," *Nat. Chem.* 2014; 6:673-80.

32. Alezi D et al., "Quest for highly connected metal-organic framework platforms: rare-earth polynuclear clusters versatility meets net topology needs," *J. Am. Chem. Soc.* 2015; 137:5421-30.

33. Chupas P J et al., "Rapid-acquisition pair distribution function (RA-PDF) analysis," *J. Appl. Crystallogr.* 2003; 36:1342-7.

34. Chupas P J et al., "Applications of an amorphous silicon-based area detector for high-resolution, high-sensitivity and fast time-resolved pair distribution function measurements," *J. Appl. Crystallogr.* 2007; 40:463-70.

35. Sinclair M B et al., "Hyperspectral confocal microscope," *Appl. Opt.* 2006; 45:6283-91.

36. Jones H D T et al., "preprocessing strategies to improve MCR analyses of hyperspectral images," *Chemometrics Intell. Lab. Syst.* 2012; 117:149-58.

37. Haaland D M et al., "Chapter 12—Experimental and Data Analytical Approaches to Automating Multivariate Curve Resolution in the Analysis of Hyperspectral Images," in *Data Handling in Science and Technology* (C Ruckebusch, ed.), Elsevier (Amsterdam, The Netherlands, 2016), vol. 30, pp. 381-408.

38. Chen B et al., "Metal-organic frameworks with functional pores for recognition of small molecules," *Acc. Chem. Res.* 2010; 43:1115-24.

39. Chapman K W, "Emerging operando and x-ray pair distribution function methods for energy materials development," *MRS Bull.* 2016; 41:231-40.

40. Giménez-Marques M et al., "Nanostructured metal-organic frameworks and their bio-related applications," *Coord. Chem. Rev.* 2016; 307, Part 2:342-60.

41. Cravillon J et al., "Rapid room-temperature synthesis and characterization of nanocrystals of a prototypical zeolitic imidazolate framework," *Chem. Mater.* 2009; 21:1410-2.

42. Fissan H et al., "Comparison of different characterization methods for nanoparticle dispersions before and after aerosolization," *Anal. Methods* 2014; 6:7324-34.

43. Hirschle P et al., "Exploration of MOF nanoparticle sizes using various physical characterization methods—is what you measure what you get?," *Cryst. Eng. Comm.* 2016; 18:4359-68.

44. Orellana-Tavra C et al., "Drug delivery and controlled release from biocompatible metal-organic frameworks using mechanical amorphization," *J. Mater. Chem. B* 2016; 4:7697-707.

45. Semisch A et al., "Copper ions interfere with the reduction of the water-soluble tetrazolium salt-8," *Chem. Res. Toxicol.* 2014; 27:169-71.

46. Sohaebuddin S K et al., "nanomaterial cytotoxicity is composition, size, and cell type dependent," *Part. Fibre Toxicol.* 2010; 7:22 (17 pp.).

47. Tamames-Tabar C et al., "Cytotoxicity of nanoscaled metal-organic frameworksm," *J. Mater. Chem. B* 2014; 2:262-71.

48. Hu Q et al., "A low cytotoxic cationic metal-organic framework carrier for controllable drug release," *J. Med. Chem.* 2014; 57:5679-85.

49. Aaron J S et al., "Advanced optical imaging reveals the dependence of particle geometry on interactions between CdSe quantum dots and immune cells," *Small* 2011; 7:334-41.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A metal-organic framework composition comprising a plurality of metal clusters and a plurality of ligands coordinating with the plurality of metal clusters, wherein at least one metal cluster comprises a metal ion, at least one ligand is a monodentate ligand, and at least one ligand is a bidentate ligand, wherein the plurality of metal clusters and plurality of ligands are characterized by a tetragonal crystal structure, wherein the at least one metal cluster comprises a hexanuclear cluster, wherein the metal ion is a rare earth metal ion selected from the group consisting of Eu, Nd, Yb, Y, Tb, La, Ce, Pr, Sm, Gd, Dy, Ho, Er, Tm, and Lu, and wherein each of the plurality of ligands, independently, comprises a structure of $L^1$-$R^L$-$L^2$, wherein each of $L^1$ and $L^2$ is, independently, a reactive group, and wherein $R^L$ is a linker comprising an optionally substituted aryl or an optionally substituted heteroaryl.

2. The composition of claim 1, wherein each of the plurality of metal clusters comprises a hexanuclear cluster.

3. The composition of claim 1, wherein the metal ion is selected from the group consisting of Eu, Nd, Yb, Y, and Tb.

4. The composition of claim 1, wherein the plurality of metal clusters comprises a first metal ion and a second metal ion that is different than the first metal ion, and wherein the plurality of metal clusters comprises a first metal ion having a first coordination geometry and a second metal ion having a second coordination geometry that is different than the first coordinate geometry.

5. The composition of claim 1, comprising a plurality of monodentate ligands and a plurality of bidentate ligands.

6. The composition of claim 5, wherein each of the monodentate ligands and the each of the bidentate ligands comprises a structure of $L^1$-$R^L$-$L^2$, wherein each of $L^1$ and $L^2$ is, independently, a reactive group, and wherein $R^L$ is a linker.

7. The composition of claim 6, wherein $R^L$ comprises an optionally substituted aryl or an optionally substituted heteroaryl; and wherein each of $L^1$ and $L^2$ comprises, independently, carboxyl, heterocyclyl, hydroxyl, an anion thereof, a salt thereof, or an ester thereof.

8. The composition of claim 1, wherein each of $L^1$ and $L^2$ comprises, independently, carboxyl, heterocyclyl, hydroxyl, an anion thereof, a salt thereof, or an ester thereof.

9. A construct comprising:
a metal-organic framework (MOF) composition comprising a plurality of metal clusters and a plurality of ligands coordinating with the plurality of metal clusters, wherein at least one metal cluster comprises a metal ion, at least one ligand is a monodentate ligand, and at least one ligand is a bidentate ligand; and an outer layer comprising a polymer, a lipid, a lipid layer, an organic matrix, an inorganic matrix, and/or a shell, wherein the outer layer is disposed directly or indirectly on a surface of the MOF composition, wherein the at least one metal cluster comprises a hexanuclear cluster, wherein the metal ion is a rare earth metal ion selected from the group consisting of Eu, Nd, Yb, Y, Tb, La, Ce, Pr, Sm, Gd, Dy, Ho, Er, Tm, and Lu, and wherein each of the plurality of ligands, independently, comprises a structure of $L^1$-$R^L$-$L^2$, wherein each of $L^1$ and $L^2$ is, independently, a reactive group, and wherein $R^L$ is a linker comprising an optionally substituted aryl or an optionally substituted heteroaryl.

10. The construct of claim 9, further comprising:
one or more cargos disposed in proximity to and/or within the MOF composition and/or the outer layer.

11. The construct of claim 9, wherein the MOF composition is provided as one or more cores, and wherein the outer layer is disposed on an external surface, or a portion thereof, of the one or more cores.

12. A formulation comprising a construct of claim 9, or a salt or an anhydrate or a solvate thereof, and a pharmaceutically acceptable excipient.

13. The construct of claim 9, wherein each of the plurality of metal clusters comprises a hexanuclear cluster.

14. The construct of claim 9, wherein the metal ion is selected from the group consisting of Eu, Nd, Yb, Y, and Tb.

15. The construct of claim 9, wherein the plurality of metal clusters comprises a first metal ion and a second metal ion that is different than the first metal ion, and wherein the plurality of metal clusters comprises a first metal ion having a first coordination geometry and a second metal ion having a second coordination geometry that is different than the first coordinate geometry.

16. The construct of claim 9, comprising a plurality of monodentate ligands and a plurality of bidentate ligands.

17. The construct of claim 16, wherein each of the monodentate ligands and the each of the bidentate ligands comprises the structure of $L^1$-$R^L$-$L^2$.

18. The construct of claim 9, wherein each of $L^1$ and $L^2$ comprises, independently, carboxyl, heterocyclyl, hydroxyl, an anion thereof, a salt thereof, or an ester thereof.

19. The construct of claim 9, wherein the plurality of metal clusters and plurality of ligands are characterized by a tetragonal crystal structure.

20. A formulation comprising a metal-organic framework composition comprising a plurality of metal clusters and a plurality of ligands coordinating with the plurality of metal clusters, wherein at least one metal cluster comprises a metal ion, at least one ligand is a monodentate ligand, and at least one ligand is a bidentate ligand, wherein the plurality of metal clusters and plurality of ligands are characterized by a tetragonal crystal structure, wherein the at least one metal cluster comprises a hexanuclear cluster, wherein the metal ion is a rare earth metal ion selected from the group consisting of Eu, Nd, Yb, Y, Tb, La, Ce, Pr, Sm, Gd, Dy, Ho, Er, Tm, and Lu, and wherein each of the plurality of ligands, independently, comprises a structure of $L^1$-$R^L$-$L^2$, wherein each of $L^1$ and $L^2$ is, independently, a reactive group, and wherein $R^L$ is a linker comprising an optionally substituted aryl or an optionally substituted heteroaryl; or a salt or an anhydrate or a solvate thereof, and a pharmaceutically acceptable excipient.

\* \* \* \* \*